United States Patent
Wu et al.

(10) Patent No.: US 10,745,389 B2
(45) Date of Patent: Aug. 18, 2020

(54) HDAC6 SELECTIVE INHIBITORS, PREPARATION METHOD THEREFOR, AND APPLICATION THEREOF

(71) Applicants: CSTONE PHARMACEUTICALS (SUZHOU) CO., LTD., Jiangsu (CN); CSTONE PHARMACEUTICALS (SHANGHAI) CO., LTD, Shanghai (CN); CSTONE PHARMACEUTICALS, Grand Cayman (KY)

(72) Inventors: Hao Wu, Shanghai (CN); Changqing Wei, Shanghai (CN); Qiang Guo, Shanghai (CN); Guifen Zhang, Shanghai (CN); Bin Liu, Shanghai (CN); Yonggang Liao, Shanghai (CN); Yao Xiao, Shanghai (CN); Shuhui Chen, Shanghai (CN)

(73) Assignees: CSTONE PHARMACEUTICALS (SUZHOU) CO., LTD., Jiangsu (CN); CSTONE PHARMACEUTICALS (SHANGHAI) CO., LTD, Shanghai (CN); CSTONE PHARMACEUTICALS, Grand Cayman (KY)

( * ) Notice: Subject to any disclaimer, the term of this patent is extended or adjusted under 35 U.S.C. 154(b) by 0 days.

(21) Appl. No.: 16/476,660

(22) PCT Filed: Jan. 10, 2018

(86) PCT No.: PCT/CN2018/072088
§ 371 (c)(1),
(2) Date: Jul. 9, 2019

(87) PCT Pub. No.: WO2018/130155
PCT Pub. Date: Jul. 19, 2018

(65) Prior Publication Data
US 2019/0375735 A1    Dec. 12, 2019

(30) Foreign Application Priority Data

Jan. 10, 2017  (CN) .......................... 2017 1 0017287

(51) Int. Cl.
| | | |
|---|---|---|
| C07D 405/14 | (2006.01) |
| C07D 405/04 | (2006.01) |
| C07D 307/06 | (2006.01) |
| A61K 9/00 | (2006.01) |
| A61K 31/69 | (2006.01) |
| A61P 35/00 | (2006.01) |

(52) U.S. Cl.
CPC .......... C07D 405/14 (2013.01); A61K 9/0053 (2013.01); A61K 31/69 (2013.01); A61P 35/00 (2018.01); C07D 307/06 (2013.01); C07D 405/04 (2013.01)

(58) Field of Classification Search
CPC .. C07D 405/14; C07D 405/04; C07D 307/06; A61K 31/69; A61K 9/00
USPC ....................................................... 546/283.4
See application file for complete search history.

(56) References Cited

U.S. PATENT DOCUMENTS

2006/0058553 A1* 3/2006 Leahy .................. C07C 259/10
562/622

FOREIGN PATENT DOCUMENTS

| CN | 101641338 A | 2/2010 |
| CN | 103429574 A | 12/2013 |
| WO | 2011106632 A | 9/2011 |
| WO | 2012068109 A | 5/2012 |
| WO | 2015007870 A | 1/2015 |
| WO | 2015100363 A | 7/2015 |

OTHER PUBLICATIONS

International Search Report and Written Opinion of PCT/CN2018/072088 dated Apr. 17, 2018.
Barbara Muz et al., "Spotlight on ixazomib: potential in the treatment of multiple myeloma", Drug Design, Development and Therapy, 2016, vol. 10, p. 217-226.

* cited by examiner

*Primary Examiner* — Niloofar Rahmani
(74) *Attorney, Agent, or Firm* — Banner & Witcoff, Ltd.

(57) ABSTRACT

Compounds serving as histone deacetylase 6 (HDAC6) selective inhibitors, and applications thereof in the preparation of drugs for treating HDAC6-related diseases. Specifically disclosed are a compound as represented by formula (I) and a pharmaceutically acceptable salt thereof.

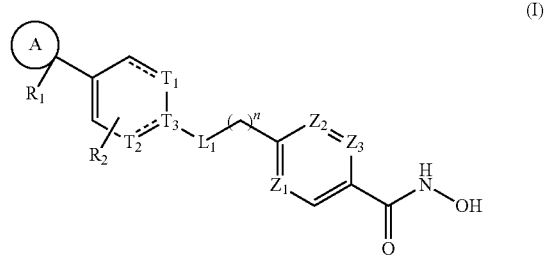

(I)

17 Claims, No Drawings

HDAC6 SELECTIVE INHIBITORS, PREPARATION METHOD THEREFOR, AND APPLICATION THEREOF

RELATED APPLICATION DATA

This application is a National Stage Application under 35 U.S.C. 371 of co-pending PCT application number PCT/CN2018/072088 filed Jan. 10, 2018; which claims the benefit of Chinese Patent Application number CN201710017287.2 filed Jan. 10, 2017, each of which are hereby incorporated by reference in their entireties.

FIELD OF INVENTION

The present invention relates to a class of compounds serving as histone deacetylase 6 (HDAC6) selective inhibitors, and applications thereof in the preparation of drugs for treating HDAC6-related diseases. Specifically, related to a compound as represented by formula (I) and a pharmaceutically acceptable salt thereof.

PRIOR ARTS

WHO experts predict that the global population will reach 8 billion in 2020, the incidence of cancer will reach 20 million, and the death rate will reach 12 million. Cancer will become the first killer of human beings in the new century and pose the most serious threat to human survival. China is in its process of industrialization, and has become the world's second-highest cancer-prone country right after the United States, the cancer incidence and mortality in China have shown a clear upward trend. In urban regions, cancer accounts first for the overall cause of death, while in rural regions, cancer accounts second for the overall cause of death. With the rapid increase in cancer morbidity and mortality in China, the annual medical expenses for cancer in the country has exceeded 150 billion yuan.

HDAC inhibitors are widely used in a variety of cancers and can be combined with a variety of drugs to enhance its therapeutic effect, it is a well-recognized anti-tumor target. In the nucleus, histone deacetylase (HDAC) and histone acetyltrans-ferase (HAT) jointly regulate gene transcription. In cancer cells, overexpression of HDAC leads to an increase in deacetylation, thereby increasing the attraction between DNA and histones, making the nucleosomes very tight, which is detrimental to the expression of tumor suppressor genes. By increasing histone acetylation, the inhibitor (HDACi) can regulate the apoptosis and differentiate the expression of related proteins, and induce apoptosis and differentiation, therefore become a new class of anti-tumor drugs. Besides, HDAC is also involved in the regulation of many metabolic diseases, such as Alzheimer's disease, Parkinson's disease (Parkinson's disease) and other diseases, HDACi inhibitors have shown good results in animal and human experiments.

Among the total of 18 deacetylase hypotypes, HDAC6 is the only deacetylase hypotype in the cytoplasm, while the other 17 HDACs are present in the nucleus. HDAC6 does not directly catalyze histones, but uses tubulin andHsp90 as substrates, through which cell trafficking, adhesion and movement (ie, no gene regulation) are regulated. Therefore, it is believed that it would less affectgene-related physiological functions and thus have fewer side effects. Current clinical trial results have confirmed that HDAC6 selective inhibitors are safe and effective (POC). Clinical studies of the first HDAC6 selective inhibitor, ACY-1215 (Acetylon), have demonstrated that selective HDAC6 inhibitors have better safety and therefore have better commercial prospects.

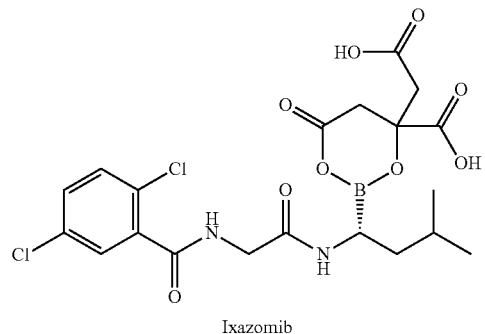 [SMILES: CC(C)C[C@H](NC(=O)CNC(=O)c1cc(Cl)ccc1Cl)B1OC(=O)CC(CC(=O)O)(C(=O)O)O1]

Ixazomib

Proteasome inhibitors (Drug Design, Development and Therapy 2016: 10 217-226) can block a large amount of regulatory proteins from degrating, causing disturbances and overloads in the intracellular signaling system, leading to inhibition of cell growth and ultimately delaying, or even stop, tumor progression. HDAC inhibitors are widely used in a variety of cancers, and can be combined with a variety of drugs to enhance its therapeutic effect, for example, the HDAC inhibitor panobinostat combining with the proteasome inhibitor bortezomib can enhance the therapeutic effect against multiple myeloma and significantly reduce its toxicity.

CONTENT OF THE PRESENT INVENTION

The present invention provides a compound represented by formula (I), a pharmaceutically acceptable salt thereof or a isomer thereof,

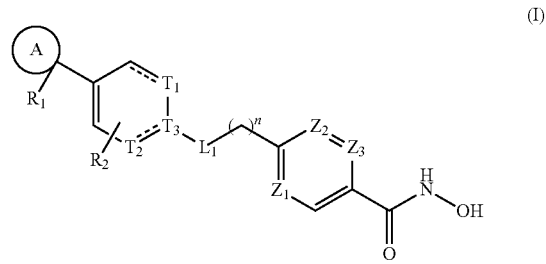

(I)

is selected from a single bond or a double bond;
n is 0 or 1;
each of $T_1$, $T_2$ is independently selected from the group consisting of CH, $CH_2$, —C(=O)— and N;
$T_3$ is C or N;
each of $Z_1$, $Z_2$, $Z_3$ is independently CH or N;
$L_1$ is selected from the group consisting of a single bond, —NH— and —C(=O)—NH—;
$R_1$ is selected from the group consisting of $C_{1-3}$ alkyl, phenyl and 6-membered heteroaryl, each of which is optionally substituted by 1, 2 or 3 R;
$R_2$ is H, F, Cl, Br or I;
ring A is 4 to 7-membered heterocycloalkyl;
R is F, Cl, Br or I;
the "hetero" in 6-membered heteroaryl, 4 to 7-membered heterocycloalkyl is independently selected from the group consisting of —NH—, N and —O—;

in any of the cases above, the number of heteroatom or heteroatom group is independently selected from 1, 2 or 3, respectively.

In some embodiments of the present invention, R₁ is selected from the group consisting of methyl, ethyl, isopropyl, phenyl and pyridyl, each of which is optionally substituted by 1, 2 or 3 R.

In some embodiments of the present invention, R₁ is selected from the group consisting of CH₃,

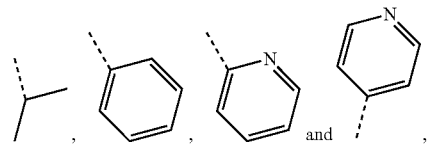

and each of which is optionally substituted by 1, 2 or 3 R.

In some embodiments of the present invention R is selected from the group consisting of CH₃,

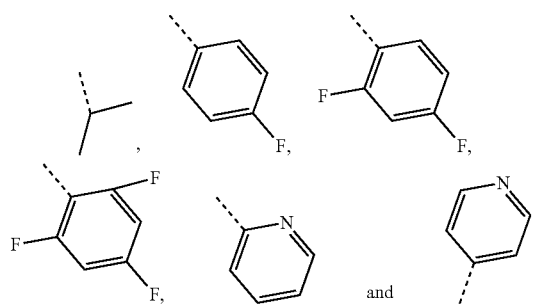

In some embodiments of the present invention, the ring A is selected from the group consisting of oxetanyl, tetrahydrofuranyl, tetrahydropyranyl, 1,3-dioxolanyl, 1,4-dioxepinyl, 1,4-dioxanyl, 1,4-oxazacycloheptyl and morpholinyl.

In some embodiments of the present invention, the ring A is selected from the group consisting of

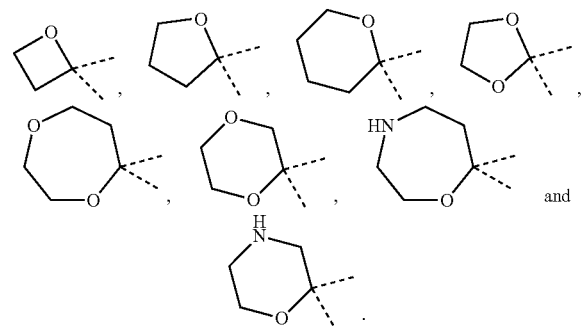

In some embodiments of the present invention, the structural unit

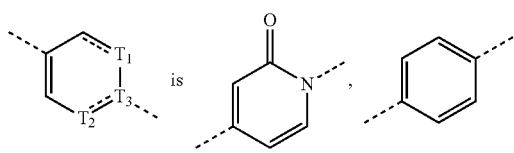

-continued

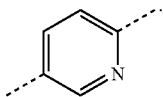

In some embodiments of the present invention, the structural unit

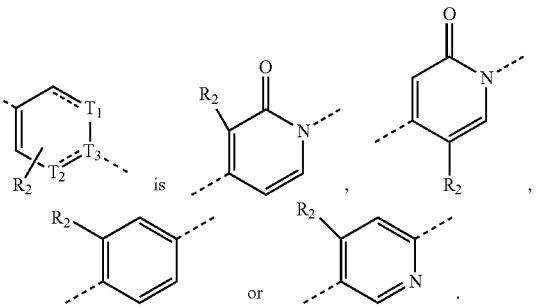

In some embodiments of the present invention, the structural unit

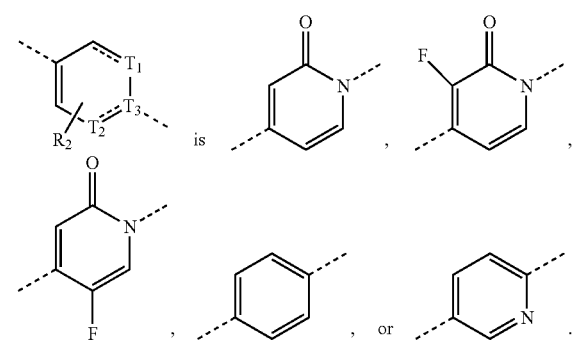

In some embodiments of the present invention, the structural unit

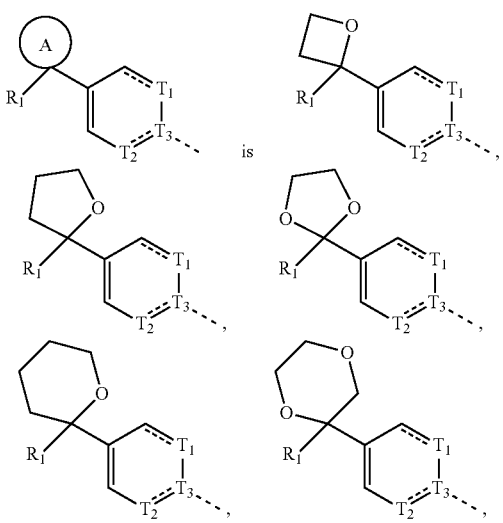

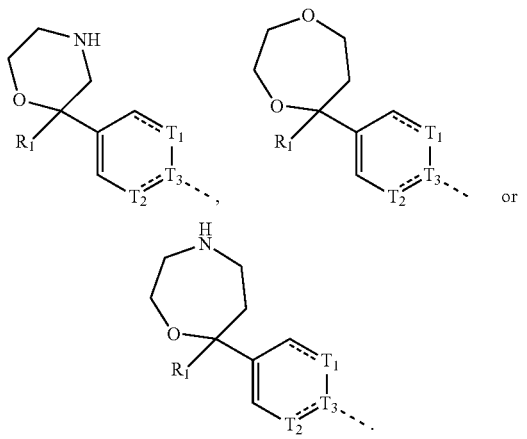
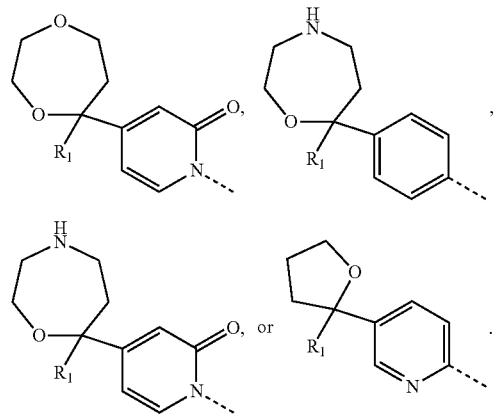
In some embodiments of the present invention, the structural unit
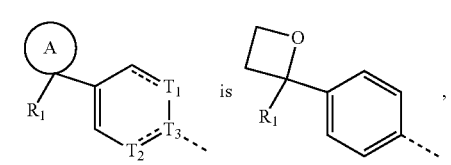 is
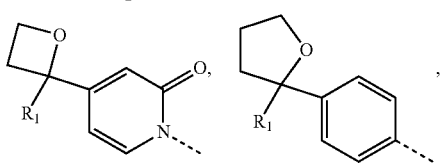,
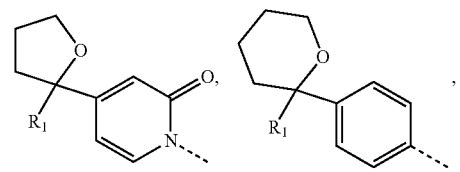,
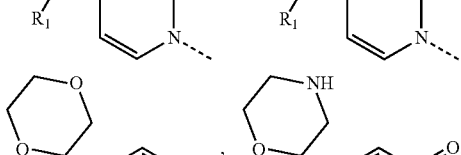,
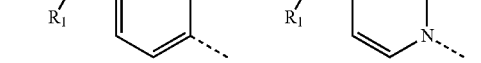,
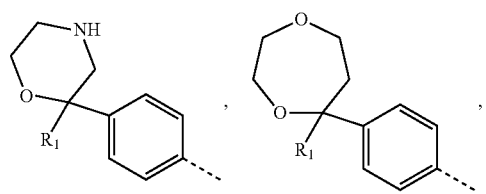,
In some embodiments of the present invention, the structural unit
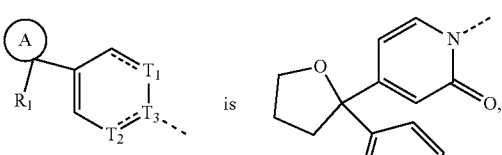 is
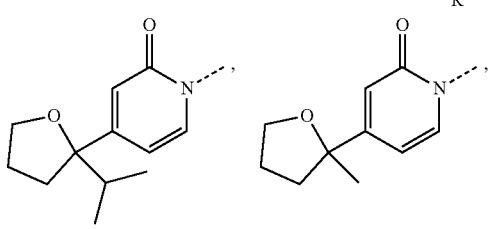,
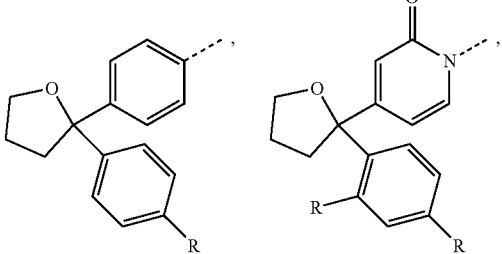,
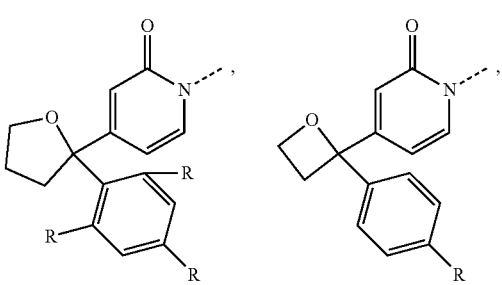

-continued
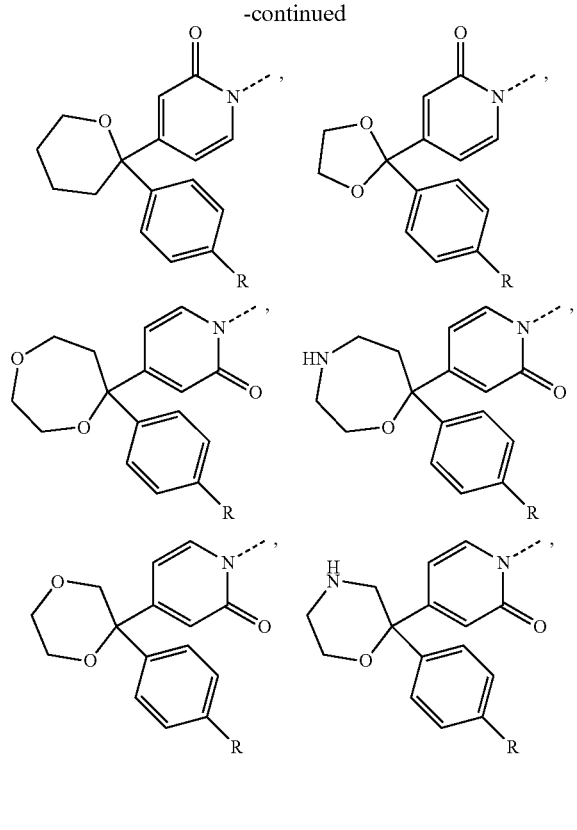
In some embodiments of the present invention, the structural unit
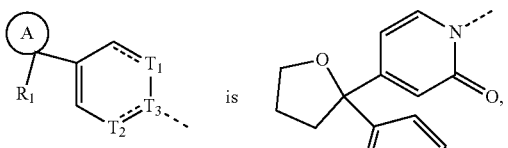
is
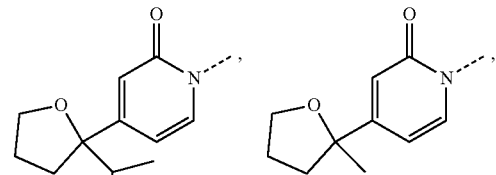
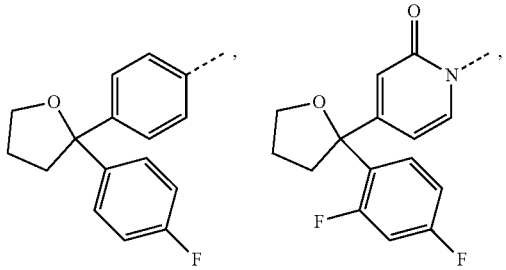
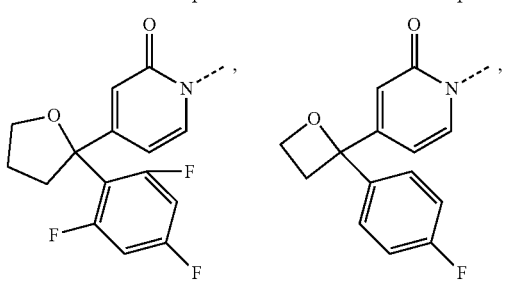
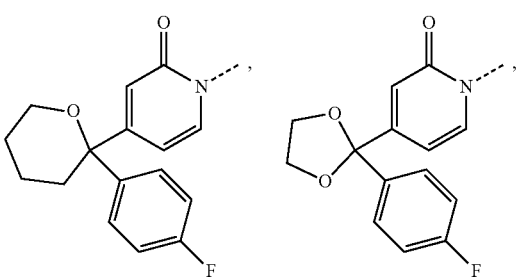
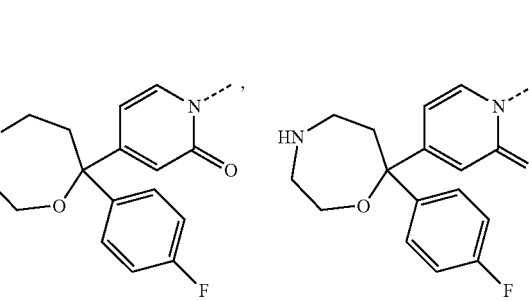

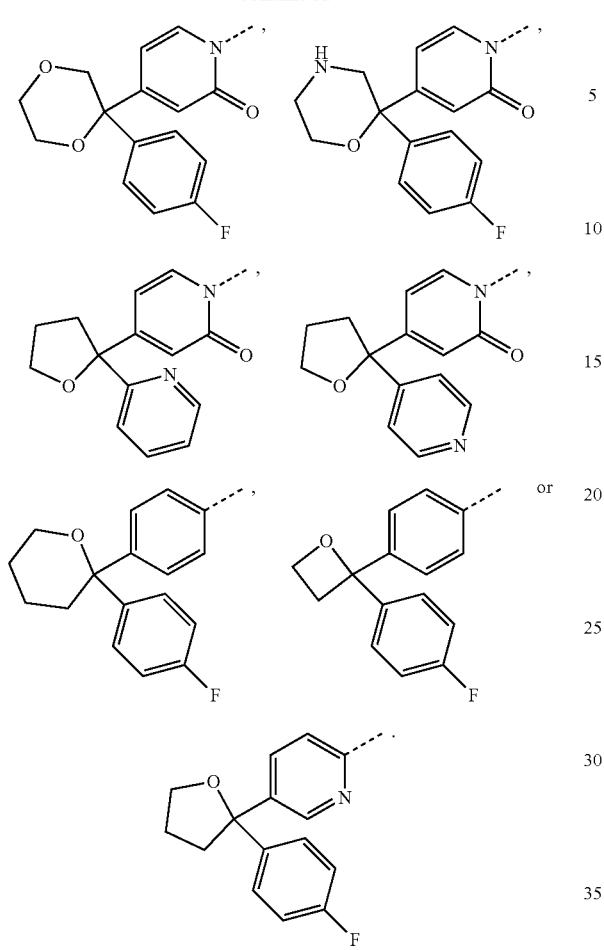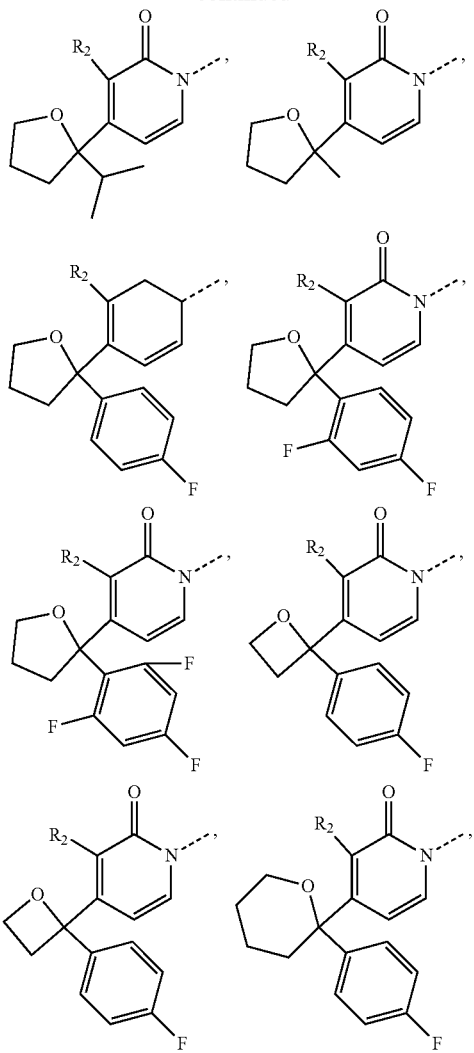
In some embodiments of the present invention, the structural unit
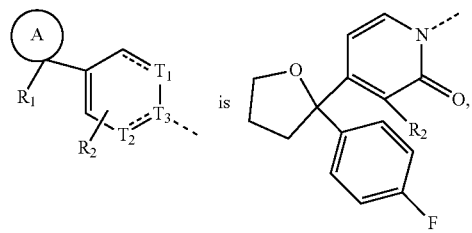 is 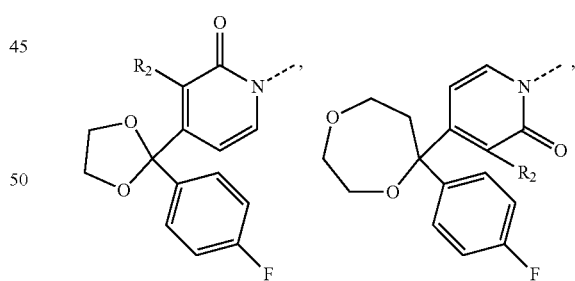
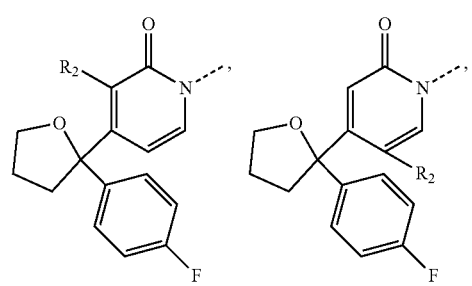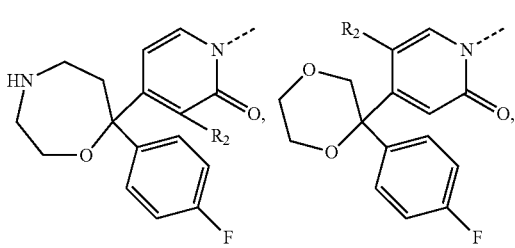

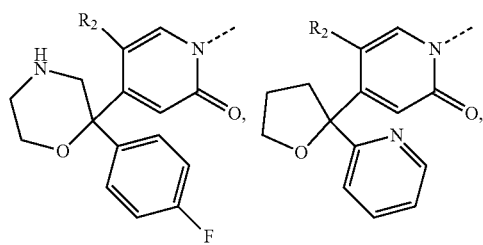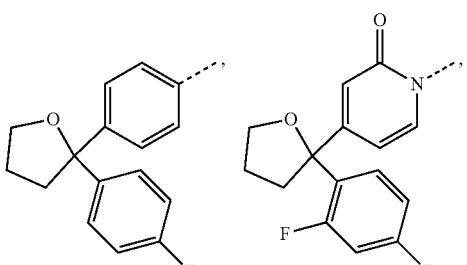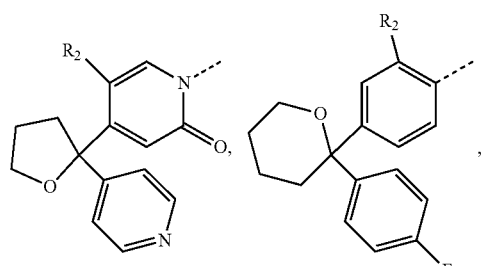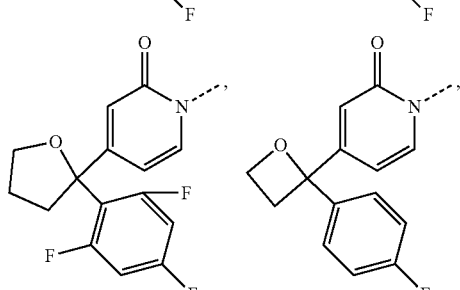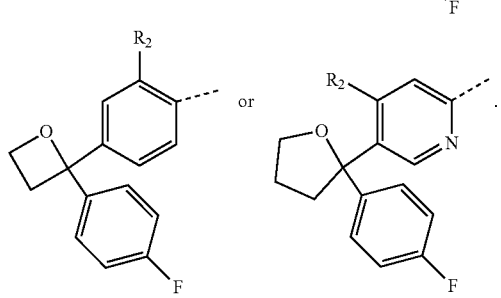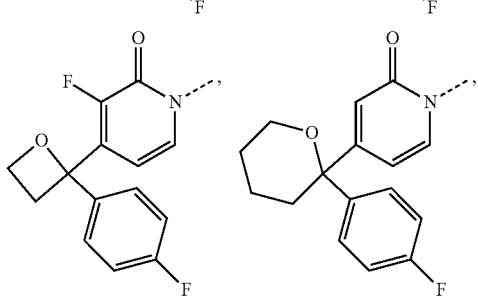
In some embodiments of the present invention, the structural unit
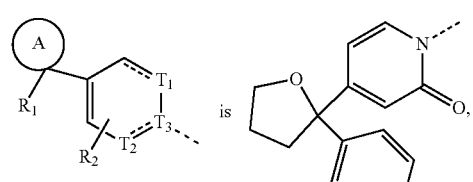 is 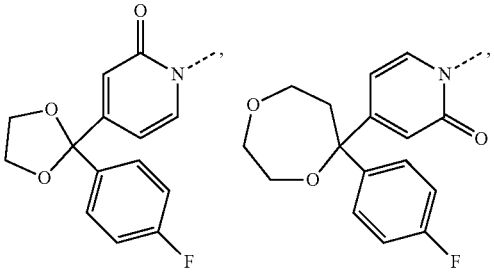
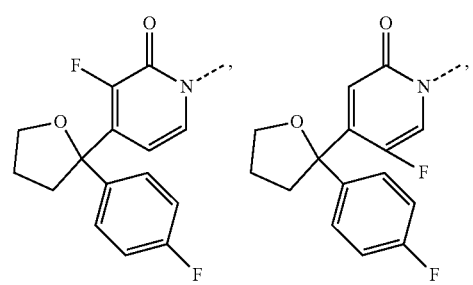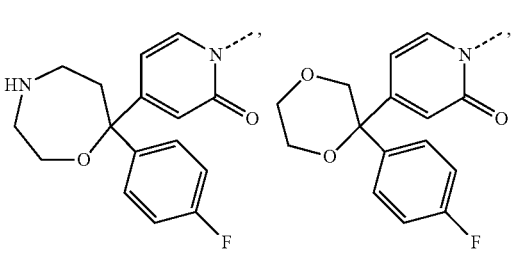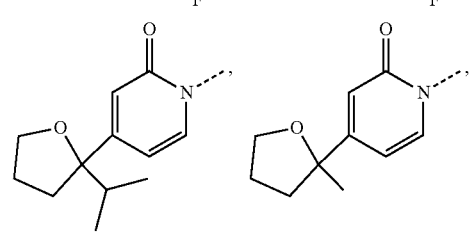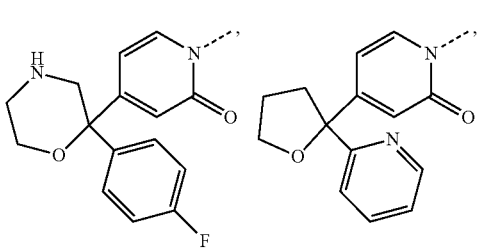

-continued

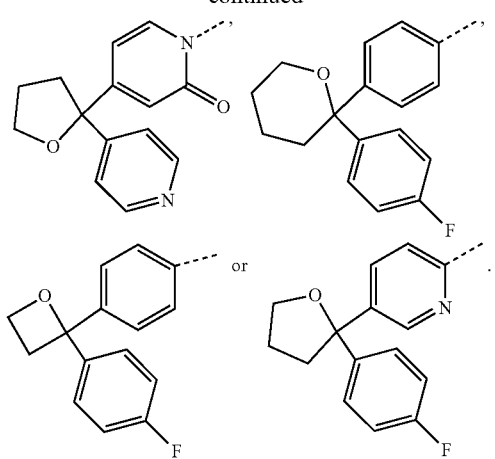

In some embodiments of the present invention, the structural unit

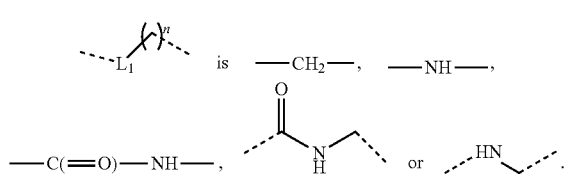

is —CH₂—, —NH—, —C(=O)—NH—,

In some embodiments of the present invention, the structural unit is

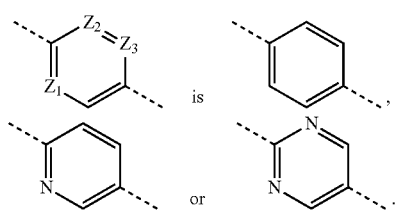

In some embodiments of the present invention, the structural unit

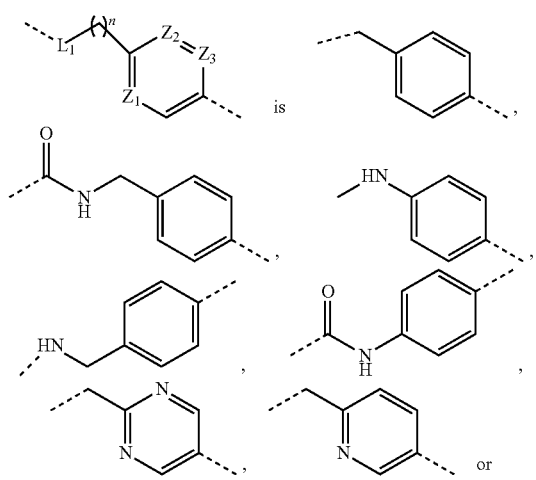

-continued

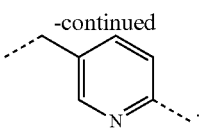

In some embodiments of the present invention, R₁ is selected from the group consisting of methyl, ethyl, phenyl and pyridyl, each of which is optionally substituted by 1, 2 or 3 R, while the other variants are as defined in the present invention.

In some embodiments of the present invention, R₁ is selected from the group consisting of CH₃,

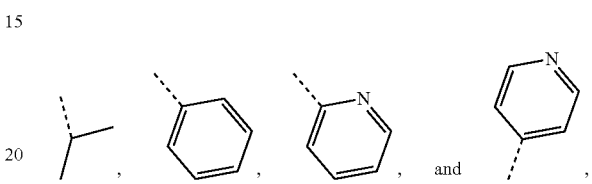

each of which is optionally substituted by 1, 2 or 3 R, while the other variants are as defined in the present invention.

In some embodiments of the present invention, R₁ is selected from the group consisting of CH₃,

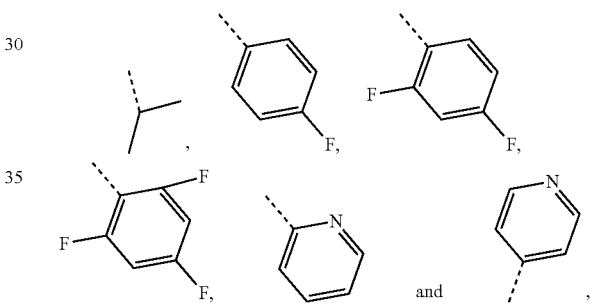

while the other variants are as defined in the present invention.

In some embodiments of the present invention, the ring A is selected from the group consisting of oxetanyl, tetrahydrofuranyl, tetrahydropyranyl, 1,3-dioxolanyl, 1,4-dioxepinyl, 1,4-dioxanyl, 1,4-oxazacycloheptyl and morpholinyl, while the other variants are as defined in the present invention.

In some embodiments of the present invention, the ring A is selected from the group consisting of

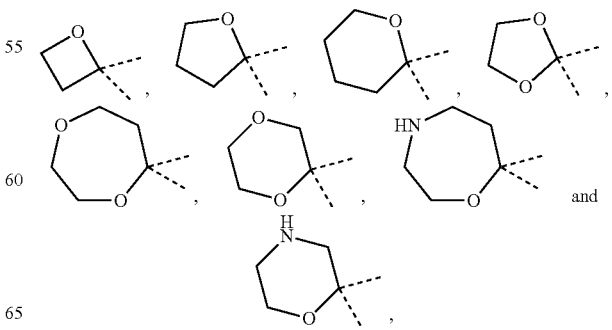

while the other variants are as defined in the present invention.

In some embodiments of the present invention, the structural unit

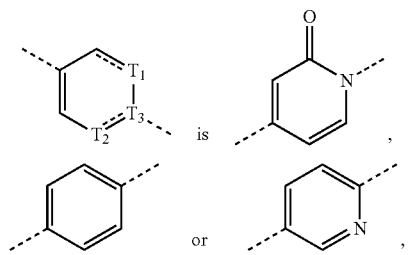

while the other variants are as defined in the present invention.

In some embodiments of the present invention, the structural unit

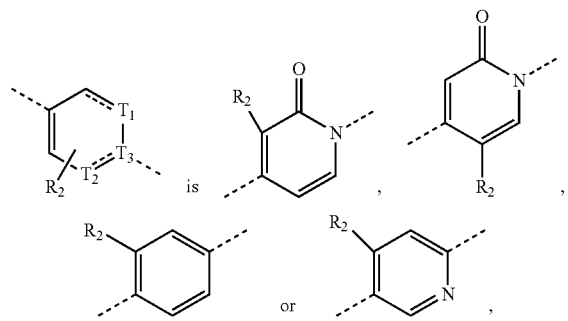

while the other variants are as defined in the present invention.

In some embodiments of the present invention, the structural unit

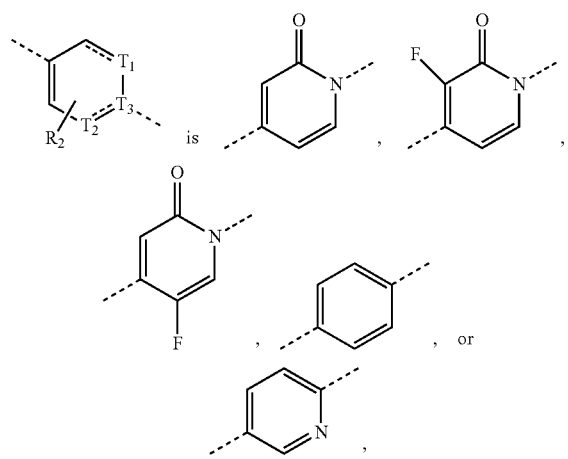

while the other variants are as defined in the present invention.

In some embodiments of the present invention, the structural unit

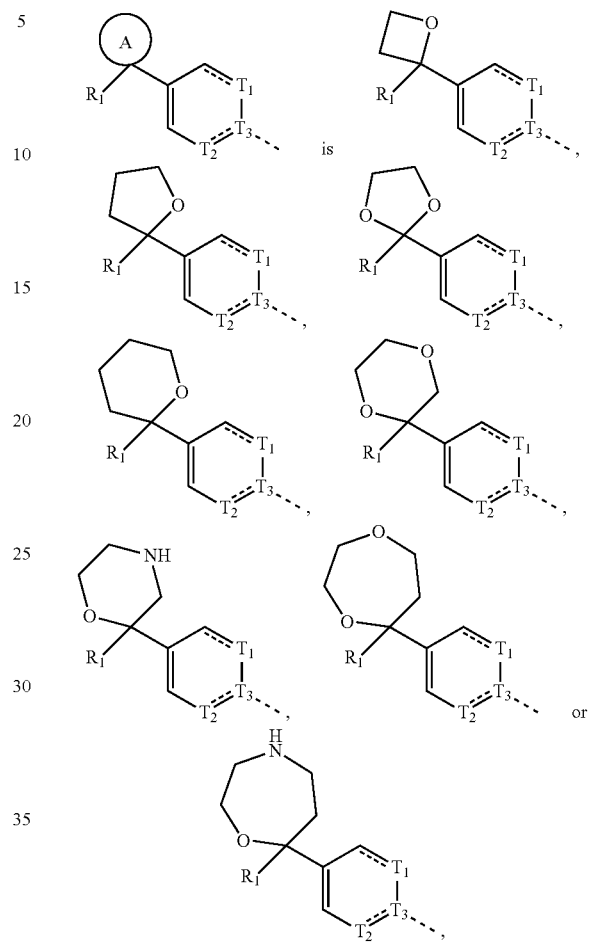

while the other variants are as defined in the present invention.

In some embodiments of the present invention, the structural unit

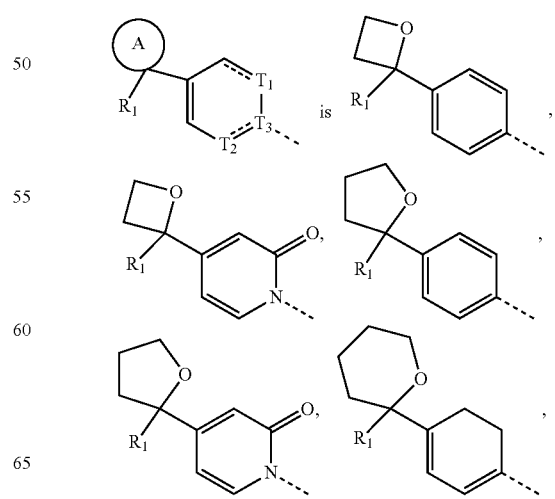

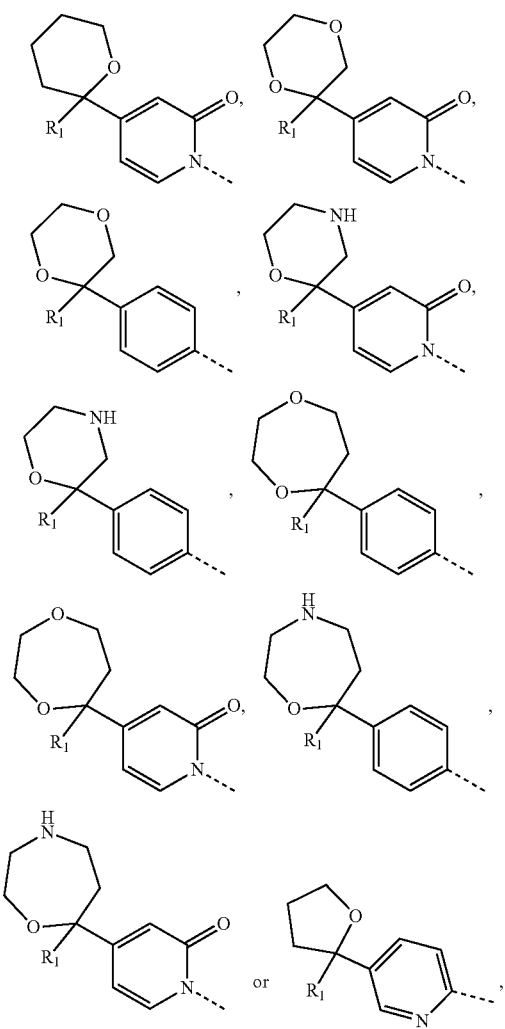
while the other variants are as defined in the present invention.
In some embodiments of the present invention, the structural unit
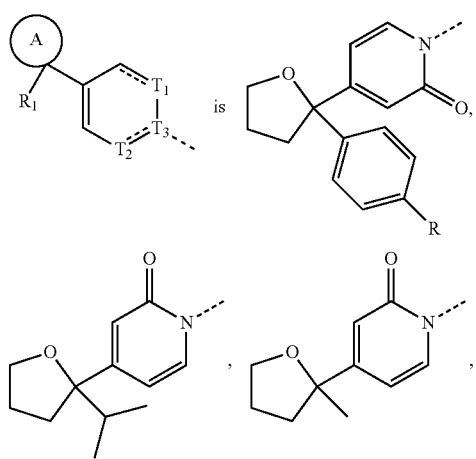 is
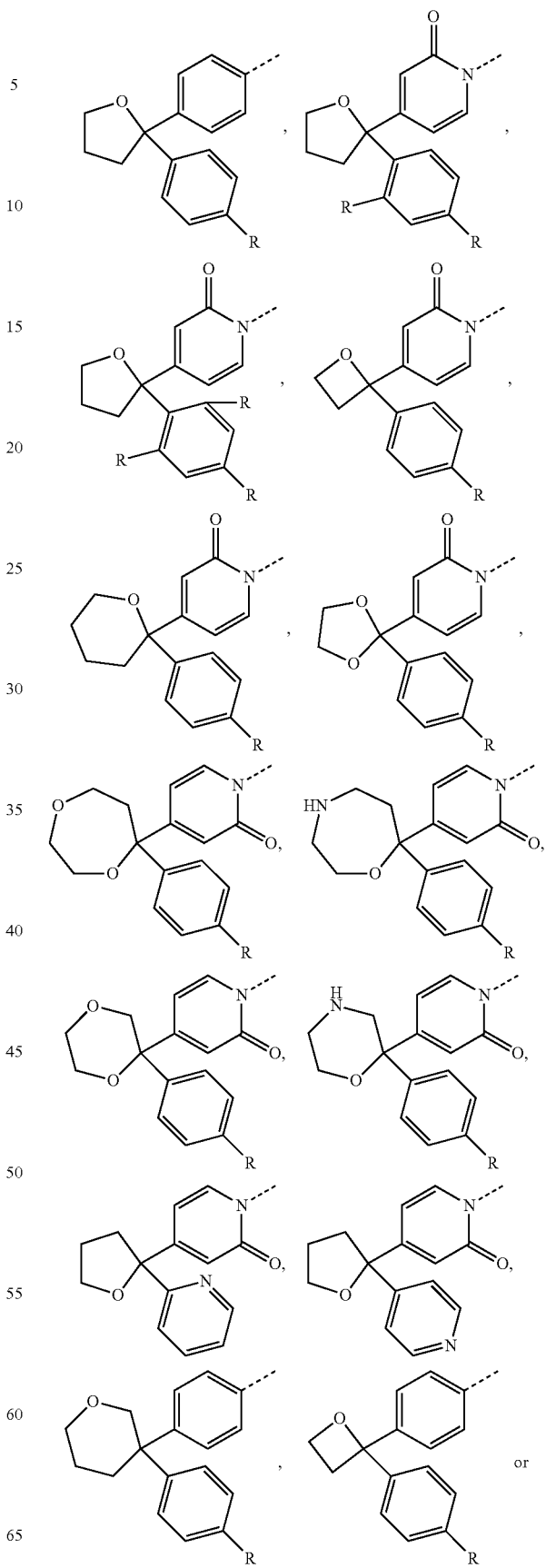

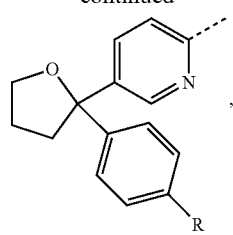
while the other variants are as defined in the present invention.
In some embodiments of the present invention, the structural unit
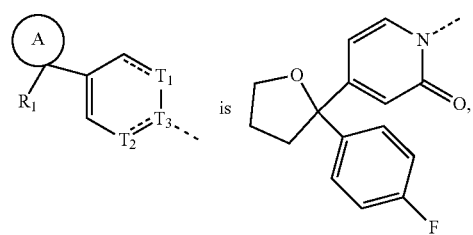 is 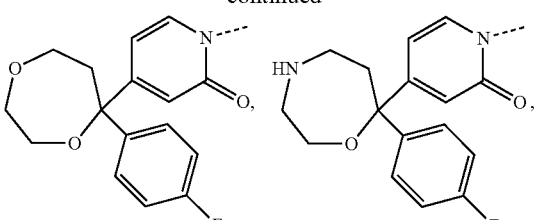
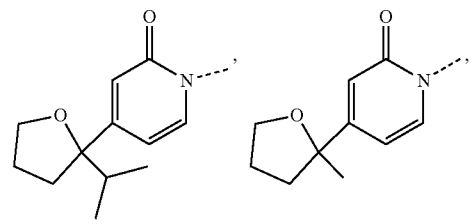
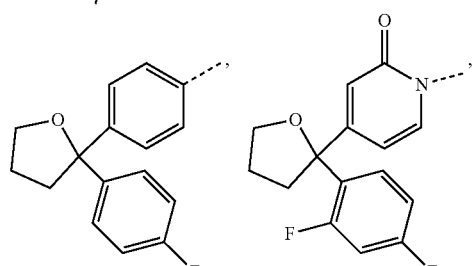
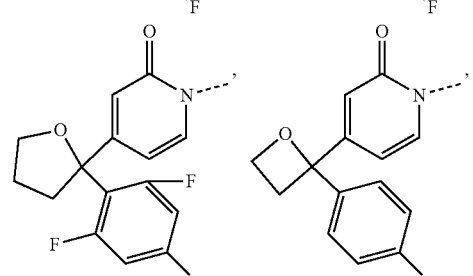
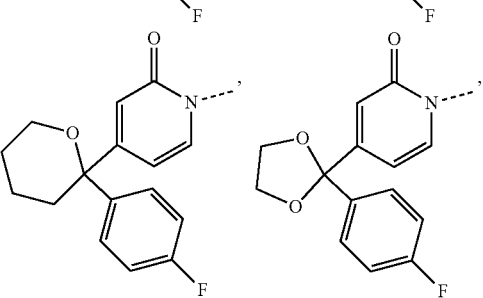
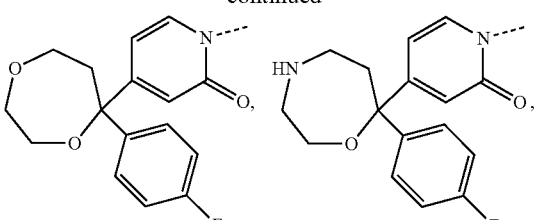
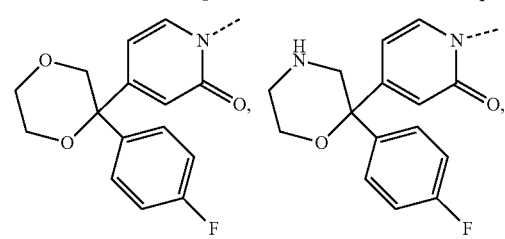
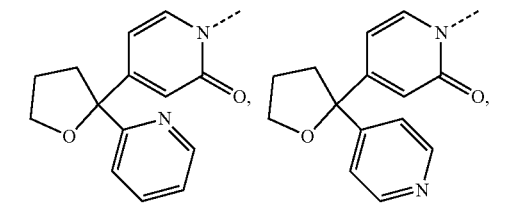
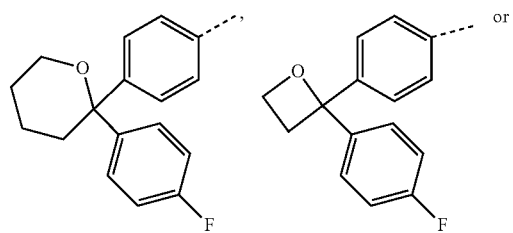
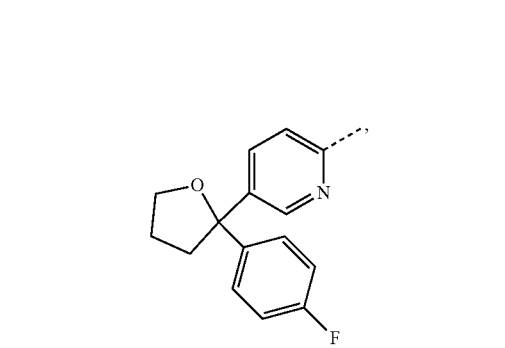
while the other variants are as defined in the present invention.
In some embodiments of the present invention, the structural unit
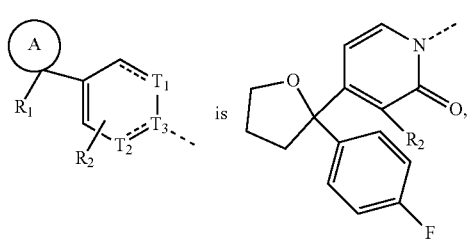

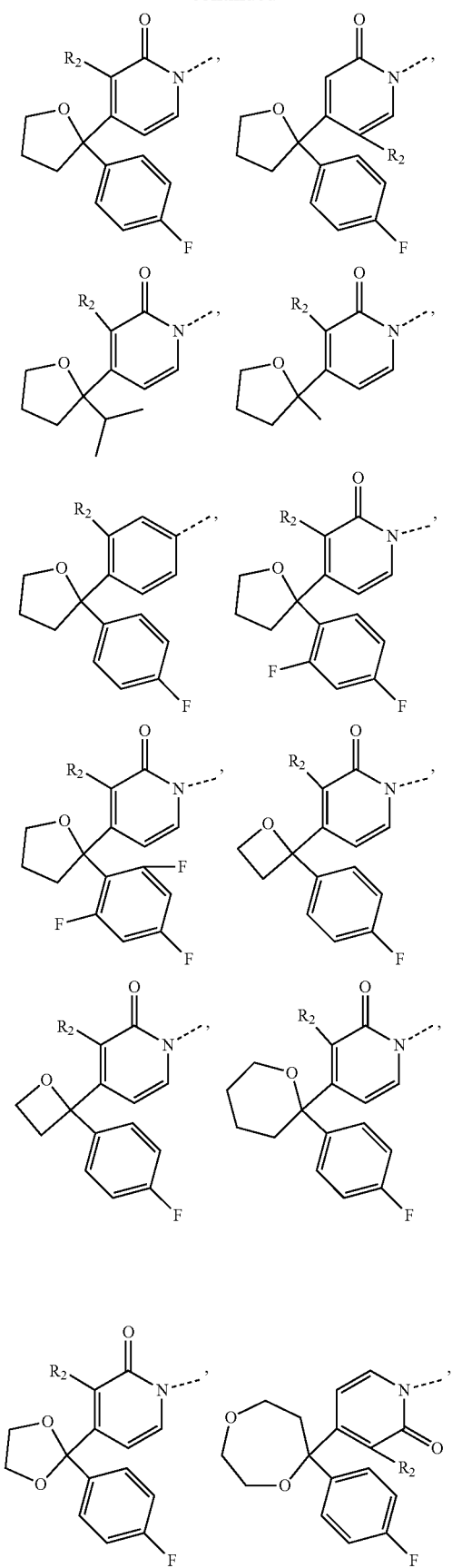
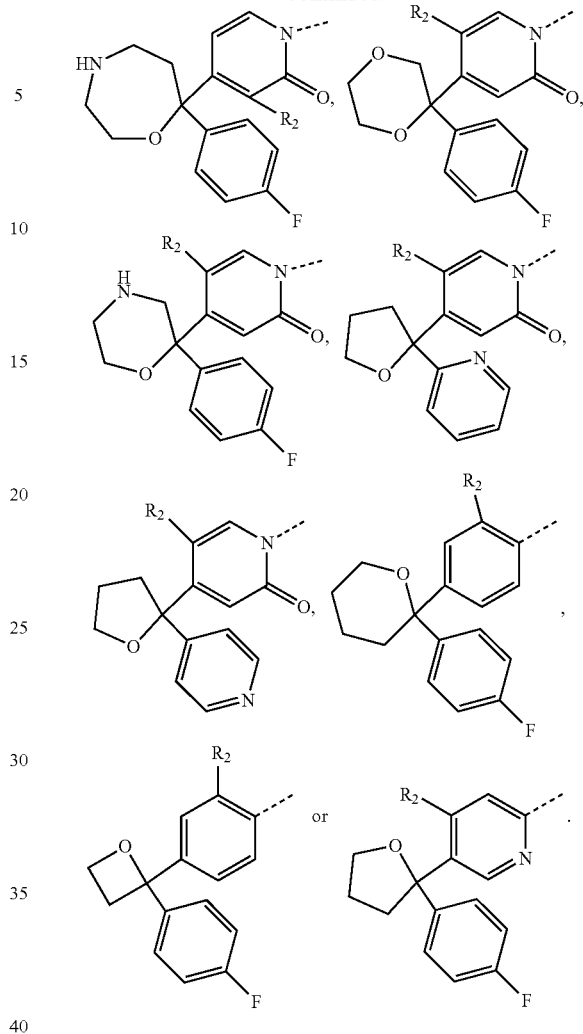
while the other variants are as defined in the present invention.
In some embodiments of the present invention, the structural unit
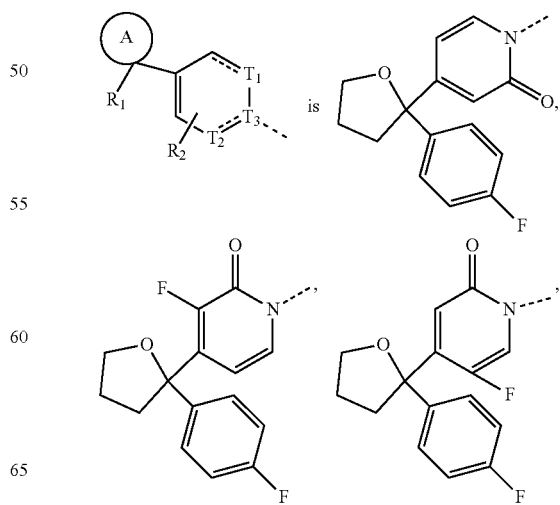

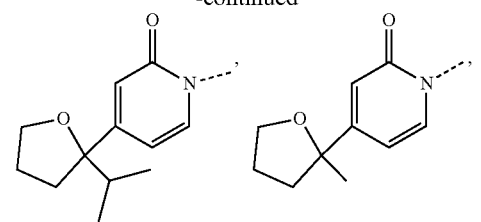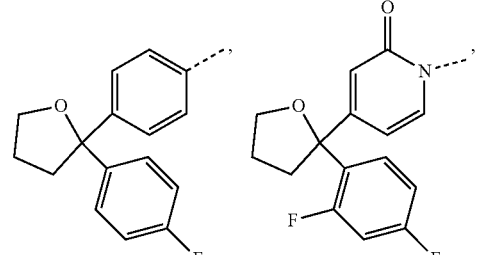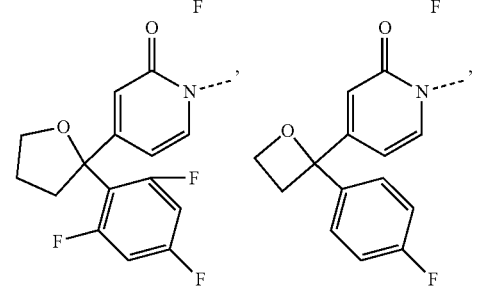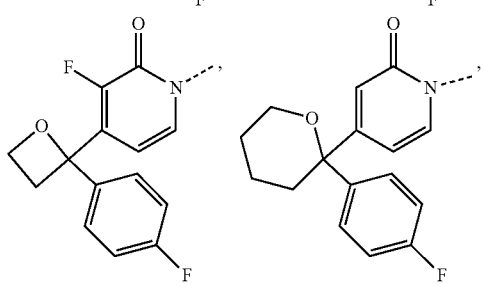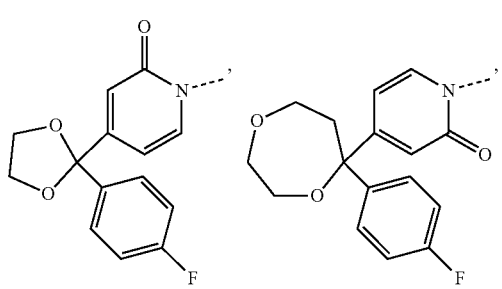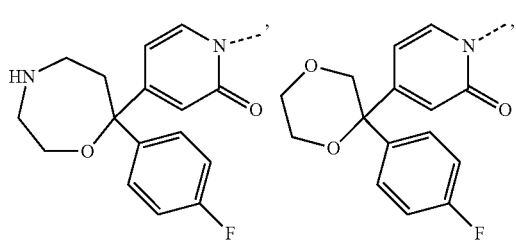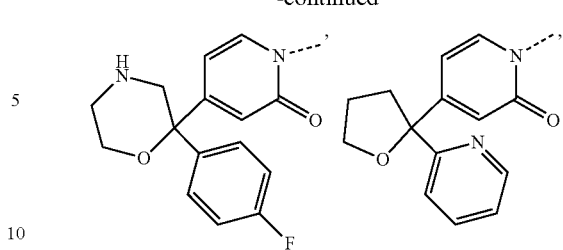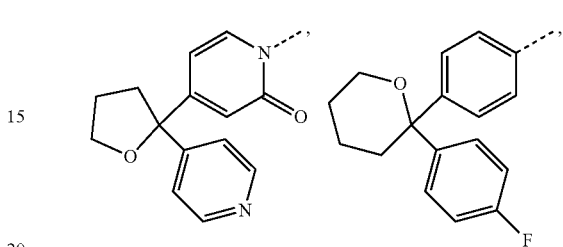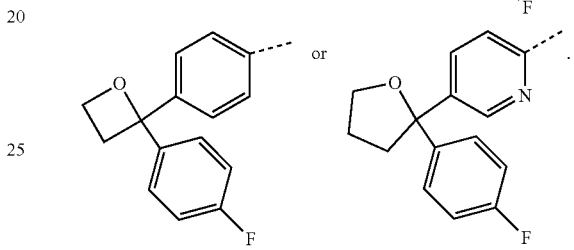
while the other variants are as defined in the present invention.
In some embodiments of the present invention, the structural unit
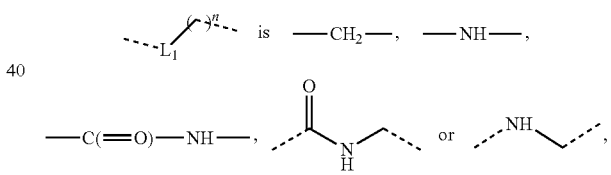
while the other variants are as defined in the present invention.
In some embodiments of the present invention, the structural unit
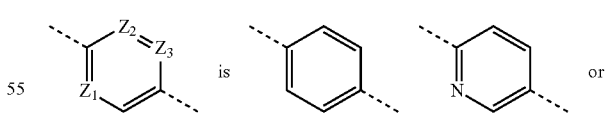
while the other variants are as defined in the present invention.

In some embodiments of the present invention, the structural unit

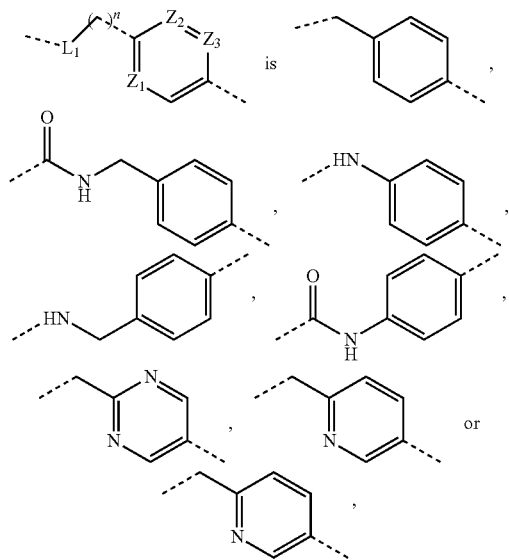

while the other variants are as defined in the present invention.

Some of the embodiments of the present invention are arbitrary combinations of each of the variants above.

In some embodiments of the present invention, the compound, the pharmaceutically acceptable salt or the isomer thereof is selected from the group consisting of

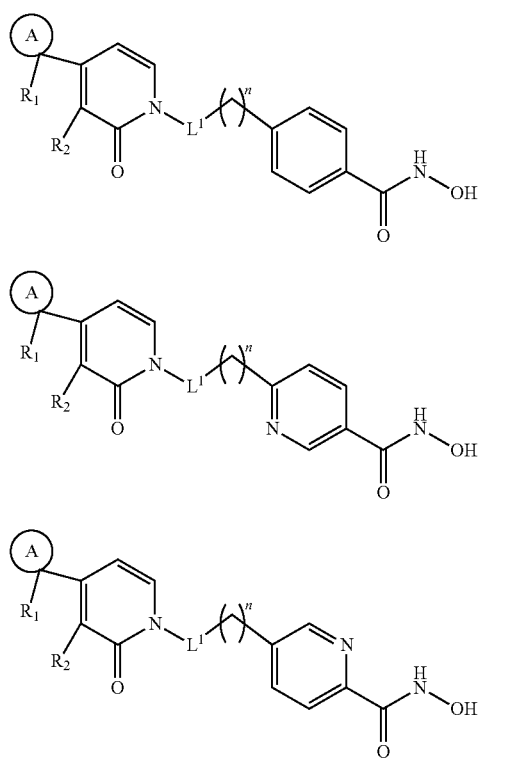

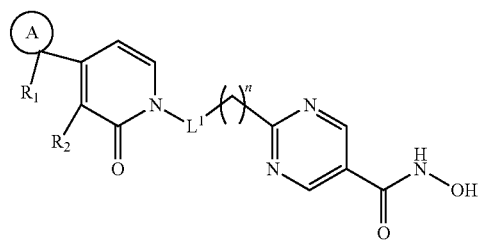

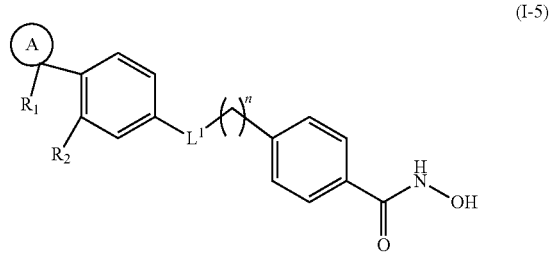

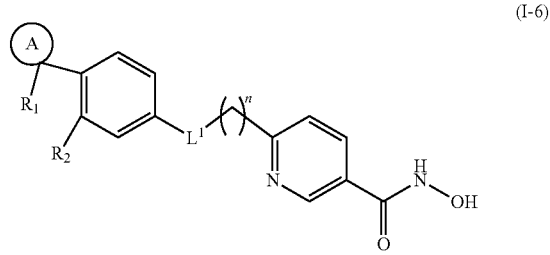

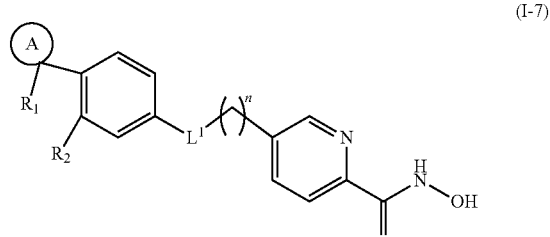

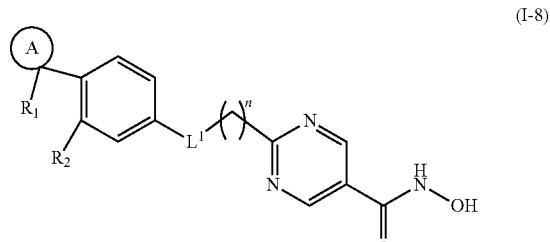

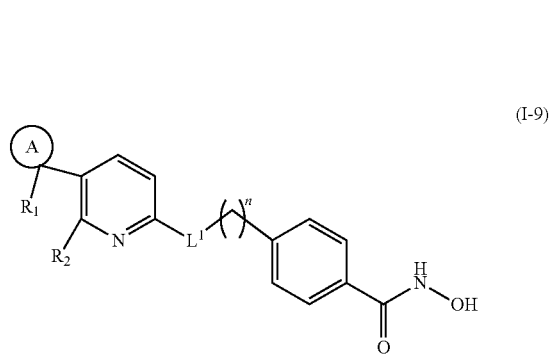

(I-10)
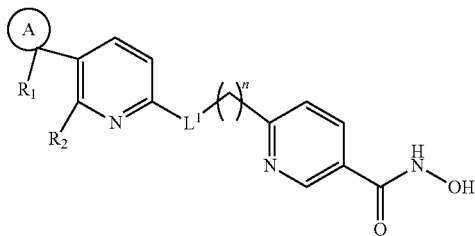

(I-11)
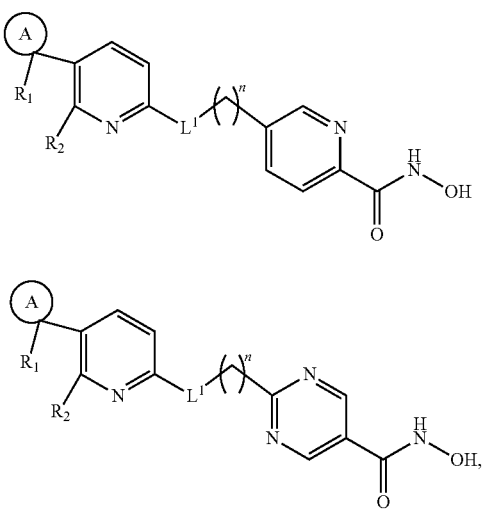
and (I-12)

wherein, ring A, $R_1$, $R_2$, $L_1$ and n are as defined in the present invention.

In some embodiments of the present invention, the compound, the pharmaceutically acceptable salt or the isomer thereof is selected from the group consisting of (I-13)
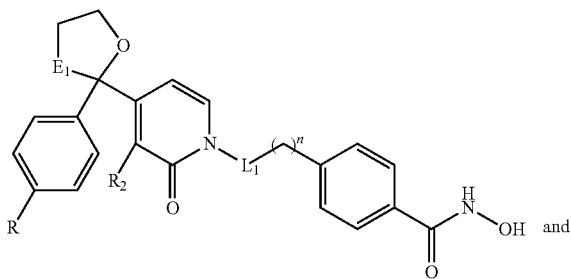
and (I-14)
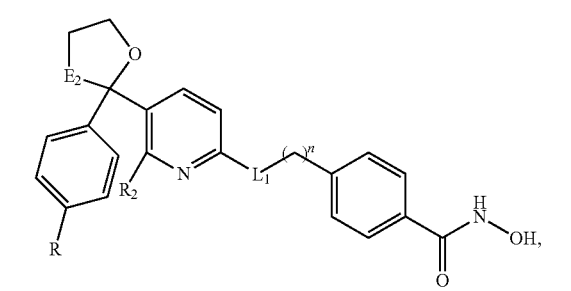

wherein, each of $E_1$, $E_2$ is independently selected from the group consisting of —O—, —CH$_2$— and —CH$_2$—CH$_2$—;

R, $R_2$, $L_1$ and n are as defined in the present invention.

The present invention also provides a compound and the pharmaceutically acceptable salt thereof, which is selected from the group consisting of

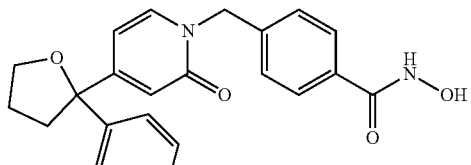

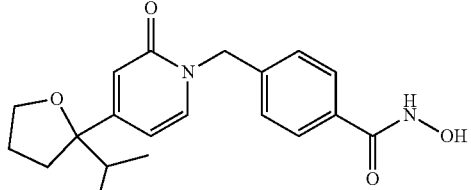

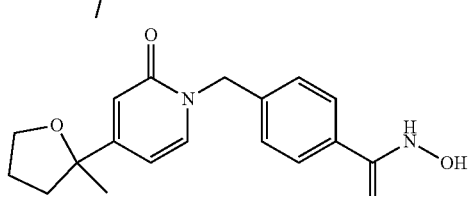

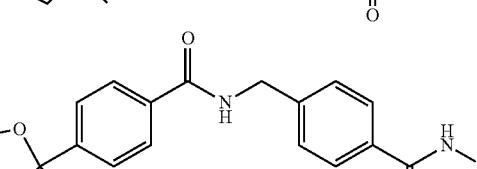

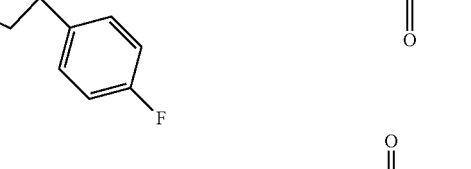

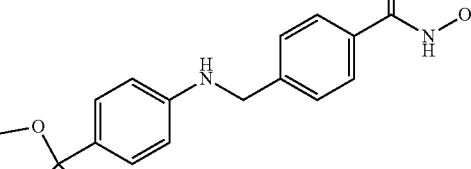

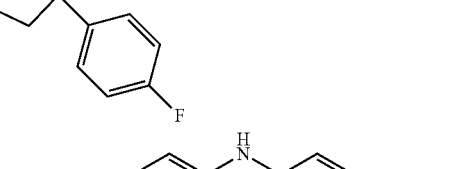

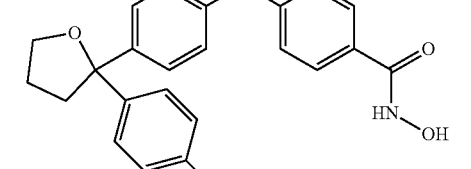

-continued
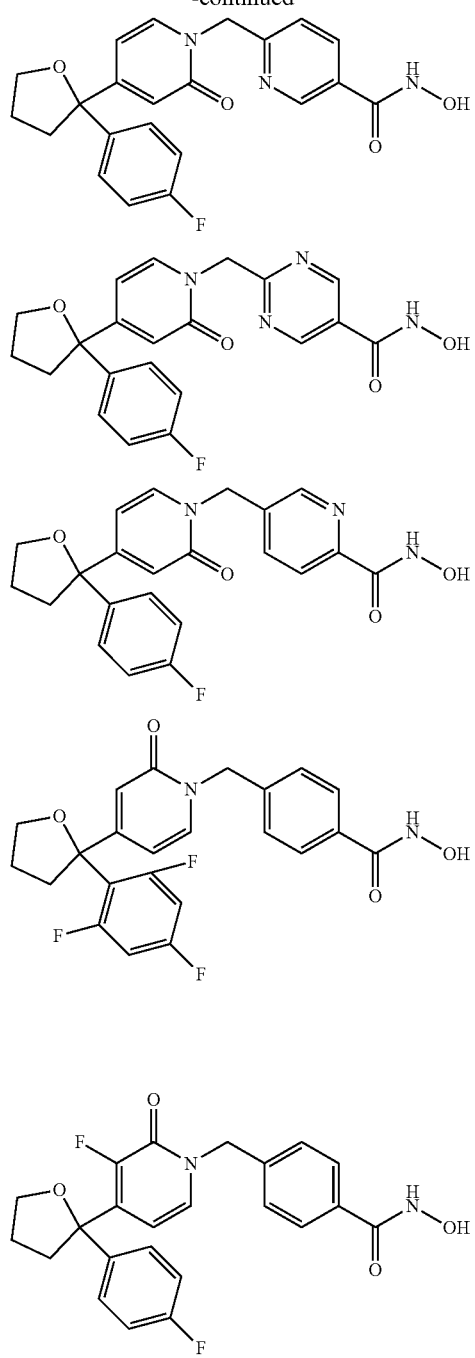
-continued
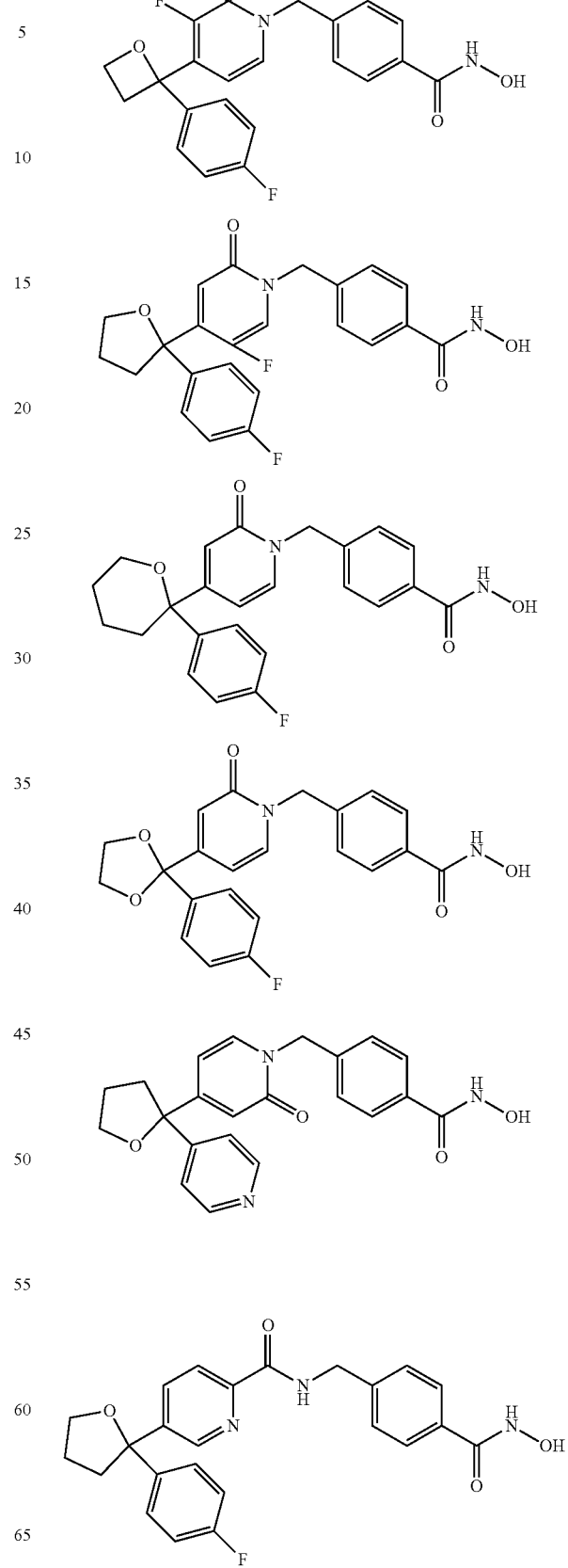

-continued

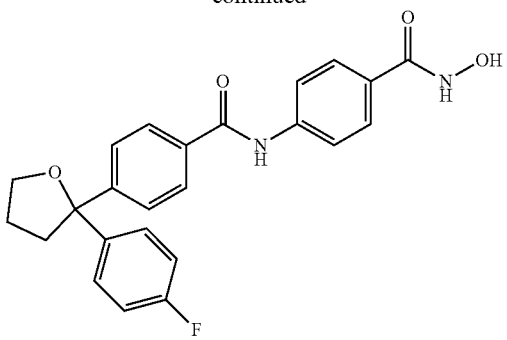

In some embodiments of the present invention, the compound, the pharmaceutically acceptable salt and the isomer thereof are selected from the group consisting of

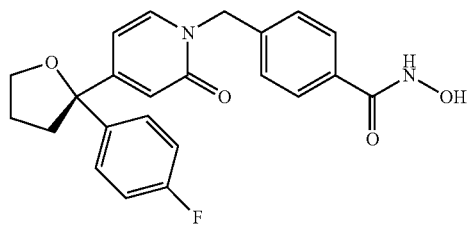

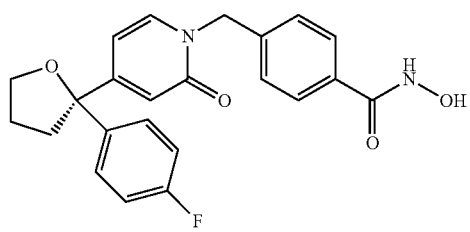

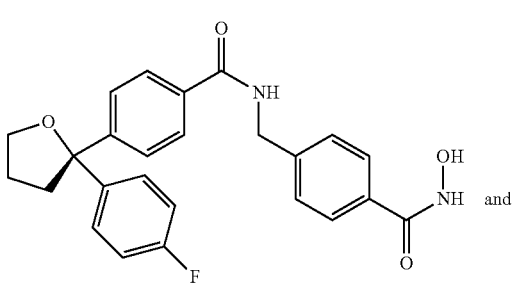 and

-continued

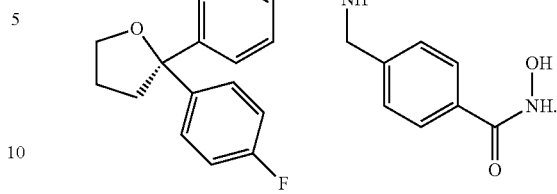

The present invention also provides a pharmaceutical composition comprising a therapeutically effective amount of the compound or a pharmaceutically acceptable salt thereof as an active ingredient and a pharmaceutically acceptable carrier.

The present invention also provides a use of the compound or the pharmaceutically acceptable salt thereof in manufacturing a medicament for the treatment of HDAC6 related diseases.

The present invention also provides a use of the composition in manufacturing a medicament for the treatment of HDAC6 related diseases.

In some embodiments of the present invention, the use is characterized by the medicament is for treating multiple myeloma.

Technical Effects

As a novel histone deacetylase 6 (HDAC6) selective inhibitor, the compound of the present invention has remarkable in vitro activity. It has a remarkable inhibitory effect on HDAC6 enzyme while a weak inhibitory effect on HDAC1, which gives it the property of high selectivity. In addition, co-administration with Ixazomib would increase the treating effect on multiple myeloma and significantly reduce toxicity.

Definitions and Descriptions

Unless otherwise indicated, the following ter MS and phrases used herein are intended to have the following meanings. A specific term or phrase should not be considered indefinite or unclear in the absence of a particular definition, but should be understood in the conventional sense. When a trade name appears herein, it is intended to refer to its corresponding commodity or active ingredient thereof. The term "pharmaceutically acceptable" is used herein in ter MS of those compounds, materials, compositions, and/or dosage for MS, which are suitable for use in contact with human and animal tissues within the scope of reliable medical judgment, with no excessive toxicity, irritation, allergic reaction or other proble MS or complications, commensurate with a reasonable benefit/risk ratio.

The term "pharmaceutically acceptable salt" refers to a salt of the compound of the present invention that is prepared by reacting the compound having a specific substituent of the present invention with a relatively non-toxic acid or base. When the compound of the present invention contains a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine or magnesium or similar salts. When the compound of the present invention contains a relatively basic functional group, an acid addition salt can be obtained by bringing the neutral form of the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and an salt of amino acid (such as arginine and the like), and a salt of an organic acid such as glucuronic acid and the like (refer to Berge et al., "Pharmaceutical Salts", Journal of Pharmaceutical Science 66: 1-19 (1977)). Certain specific compounds of the present invention contain both basic and acidic functional groups and can be converted to any base or acid addition salt.

Preferably, through bringing the salt into contact with a base or an acid in a conventional manner, then separating the parent compound, the neutral form of the compound is thereby regenerated. The difference between the parent form of the compound and its various salts lies in specific physical properties, such as different solubility in a polar solvent.

"Pharmaceutically acceptable salt" used herein belongs to a derivative of the compound of the present invention, wherein, the parent compound is modified by forming a salt with an acid or a base. Examples of the pharmaceutically acceptable salt include but are not limited to an inorganic acid or organic acid salt of a basic moiety such as amine, an alkali metal salt or an organic salt of an acidic moiety such as carboxylic acid, and the like. The pharmaceutically acceptable salt includes conventional non-toxic salt or quaternary ammonium salt of the parent compound, such as a salt formed by a non-toxic inorganic acid or an organic acid. The conventional non-toxic salt includes but is not limited to the salt derived from an inorganic acid and an organic acid, wherein the inorganic acid or organic acid is selected from the group consisting of 2-acetoxybenzoic acid, 2-hydroxyethanesulfonic acid, acetic acid, ascorbic acid, benzenesulfonic acid, benzoic acid, bicarbonate, carbonic acid, citric acid, edetic acid, ethanedisulfonic acid, ethanesulfonic acid, fumaric acid, glucoheptose, gluconic acid, glutamic acid, glycolic acid, hydrobromic acid, hydrochloric acid, hydroiodide, hydroxyl, hydroxynaphthalene, isethionic acid, lactic acid, lactose, dodecyl sulfonic acid, maleic acid, malic acid, mandelic acid, methanesulfonic acid, nitric acid, oxalic acid, pamoic acid, pantothenic acid, phenylacetic acid, phosphoric acid, polygalactanal acid, propionic acid, salicylic acid, stearic acid, subacetic acid, succinic acid, sulfamic acid, sulfanilic acid, sulfuric acid, tannin, tartaric acid and p-toluenesulfonic acid.

The pharmaceutically acceptable salt of the present invention can be prepared from the parent compound that contains an acidic or basic moiety by conventional chemical methods. Generally, such salt can be prepared by reacting the free acid or base form of the compound with a stoichiometric amount of an appropriate base or acid in water or an organic solvent or a mixture thereof. Generally, non-aqueous media such as ether, ethyl acetate, ethanol, isopropanol or acetonitrile are preferred.

In addition to the salt form, the compound provided by the present invention also exists in prodrug form. The prodrug of the compound described herein is the compound that readily undergoes chemical change under physiological condition to be converted into the compound of the present invention. Additionally, the prodrug can be converted to the compound of the present invention by a chemical or biochemical method in vivo environment.

Certain compounds of the present invention can exist in an unsolvated form or a solvated form, including a hydrated form. Generally, the solvated form is equivalent to the unsolvated form, and both are encompassed within the scope of the present invention.

Certain compounds of the present invention can have an asymmetric carbon atom (optical center) or a double bond. The racemate, diastereomer, geometric isomer and individual isomer are all encompassed within the scope of the present invention.

Unless otherwise specified, a wedged bond and a dashed bond ( ◢ ◟◟◟ ) are used to indicate the absolute configuration of a stereogenic center, ◢ and ◟◟◟ are used to indicate the relative configuration of a stereogenic center. When the compound described herein contains an olefinic double bond or other geometric asymmetric centers, E and Z geometric isomers are included unless otherwise specified. Likewise, all tautomeric for MS are encompassed within the scope of the present invention.

The compound of the present invention may present in a specific geometric or stereoisomeric form. The present invention contemplates all such compounds, including cis and trans isomer, (−)- and (+)-enantiomer, (R)- and (S)-enantiomer, diastereoisomer, (D)-isomer, (L)-isomer, and racemic mixture and other mixtures, for example, an enantiomer or diastereoisomer enriched mixture, all of which are encompassed within the scope of the present invention. The substituent such as alkyl may have an additional asymmetric carbon atom. All these isomers and mixtures thereof are encompassed within the scope of the present invention.

Optically active (R)- and (S)-isomer, or D and L isomer can be prepared using chiral synthesis or chiral reagents or other conventional techniques. If one kind of enantiomer of certain compound of the present invention is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through the conventional method in the art to give the pure enantiomer. In addition, the enantiomer and the diastereoisomer are generally isolated through chromatography which uses a chiral stationary phase and optionally combines with a chemical derivative method (for example, carbamate generated from amine).

The compound of the present invention may contain an unnatural proportion of atomic isotope at one or more than one atom(s) that constitute the compound. For example, the compound can be radiolabeled with a radioactive isotope, such as tritium ($^3H$), iodine-125 ($^{125}I$) or C-14 ($^{14}C$). All isotopic variations of the compound of the present invention, whether radioactive or not, are encompassed within the scope of the present invention. "Optional" or "Optionally" refers to the case or situation is not necessary to occur, and this term includes the occurrence or the absent of the occurrence of the case or the situation.

The term "substituted" means one or more than one hydrogen atom(s) on a specific atom are substituted by a substituent, including deuterium and hydrogen variants, as long as the valence of the specific atom is normal and the substituted compound is stable. When the substituent is a keto group (i.e. =O), it means two hydrogen atoms are substituted. Positions on an aromatic ring cannot be substituted by a keto group. The term "optionally substituted" means an atom can be substituted by a substituent or not, unless otherwise specified, the species and number of the substituent may be arbitrary as long as being chemically achievable.

When any variable (such as R) occurs in the constitution or structure of the compound more than once, the definition of the variable at each occurrence is independent. Thus, for example, if a group is substituted by 0-2 R, the group can be optionally substituted by up to two R, wherein the definition of R at each occurrence is independent. Moreover, a combination of the substituent and/or the variant thereof is allowed only when the combination results in a stable compound.

When the number of the linking group is 0, for example —(CRR)$_0$—, this means the linking group is a single bond.

When one of the variants is a single bond, this means that the two group linked by it is directly linked, for example, the L in A-L-Z represents a single bond, the actual structure is A-Z.

When a substituent is vacant, this means the substituent does not exist, for example when X in A-X is vacant, its actual structure then is A. When a bond of a substituent can be cross-linked to two atoms on a ring, such substituent can be bonded to any atom on the ring. When an enumerative substituent does not indicate by which atom it is attached to a compound included in the general chemical formula but not specifically mentioned, such substituent can be bonded by any of its atoms. A combination of substituents and/or variants thereof is allowed only when such combination can result in a stable compound. For example, the structural unit

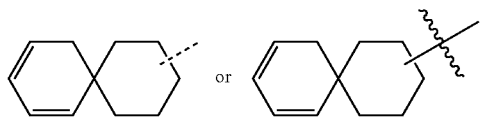

means that it can be substituted at any position on cyclohexyl or cyclohexadiene.

Unless otherwise specified, the term "hetero" represents a heteroatom or a heteroatom group (e.g., an atom group containing a heteroatom), including the atom except carbon (C) and hydrogen (H) and the atom group containing the above heteroatom, for example, including oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O), —S(=O)$_2$—, and the group consisting of —C(=O)N(H)—, —N(H)—, —C(=NH)—, —S(=O)$_2$N(H)— and —S(=O)N(H)—, each of which is optionally substituted.

Unless otherwise specified, the term "ring" refers to a substituted or unsubstituted cycloalkyl, heterocycloalkyl, cycloalkenyl, heterocycloalkenyl, cycloalkynyl, heterocycloalkynyl, aryl or heteroaryl. The so-called ring includes a single ring, a ring assembly, a spiral ring, a fused ring or a bridged ring. The number of the atom on the ring is usually defined as the member number of the ring, for example, a "5-7 membered ring" means that 5 to 7 atom are arranged on a ring. Unless otherwise specified, the ring optionally contains 1 to 3 heteroatom. Therefore, a "5-7 membered ring" includes, for example, phenyl, pyridinyl and piperidinyl; on the other hand, the term "5-7 membered heterocycloalkyl ring" includes pyridyl and piperidinyl, but excluding phenyl. The term "ring" also includes a ring system containing at least one ring, wherein each ring independently meets the above definition.

Unless otherwise specified, the term "heterocycle" or "heterocyclo" refers to a stable monocyclic, bicyclic or tricyclic ring containing a heteroatom or a heteroatom group, which can be saturated, partially unsaturated or unsaturated (aromatic) and can contain carbon atom and 1, 2, 3 or 4 ring heteroatom independently selected from N, O and S, wherein any of the above heterocycle can be fused to a benzene ring to form a bicyclic ring. The N atom could be substituted or unsubstituted (i.e. N or NR, wherein the R is H or other substituents defined herein). The heterocycle could attach to side groups of any heteroatom or C atom, forming a stable structure. If the compound is stable, the heterocycle described herein may substitution on C or N sites. The N atom in the heterocycle is optionally quaternized. In one preferred embodiment, when the total number of S and O atom in the heterocycle is more than 1, these heteroatom are not adjacent to each other. In another preferred embodiment, the total number of S and O in the heterocycle do not pass 1. As used herein, the term "aromatic heterocyclic group" or "heteroaryl" means a stable 5, 6 or 7 membered monocyclic or bicyclic, or 7, 8, 9 or 10 membered bicyclic heterocyclic aromatic ring, it includes C atom and 1, 2, 3 or 4 cyclic heteroatoms independently selected from N, O or S. The N atom could be substituted or unsubstituted (i.e. N or NR, wherein R is H or other substituent defined herein). The N and S heteroatom could be optionally oxidized (i.e. NO and S(O)p, p is 1 or 2). Its worth noting that the total number of S and O atom in the aromatic heterocycle should not be more than 1. Bridged rings are also included in the definition of heterocycles. A bridged ring is formed when one or more atom (i.e. C, O, N or S) linked two non-adjacent C or N atom. Preferred bridged ring include, but are not limited to, one C atom, two C atom, one N atom, two N atom and one C—N group. It is worth noting that a bridge always transfer single ring to triple ring. In bridged ring, a substituent on the ring could also be on the bridge.

Examples of the heterocyclic compound include, but are not limited to: acridinyl, azocinyl, benzimidazolyl, benzofuranyl, benzomercaptofuranyl, benzomercaptophenyl, benzoxazolyl, benzoxazolinyl, benzothiazolyl, benzotriazolyl, benzotetrazolyl, benzoisoxazolyl, benzoisothiazolyl, benzoimidazolinyl, carbazolyl, 4aH-carbazolyl, carbolinyl, chromanyl, chromene, cinnolinyl decahydroquinolinyl, 2H, 6H-1, 5, 2-dithiazinyl, dihydrofuro[2, 3-b]tetrahydrofuranyl, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isoindolyl, isoindolinyl, isoquinolinyl, isothiazolyl, isoxazolyl, methylenedioxyphenyl, morpholinyl, naphthyridinyl, octahydro-isoquinolinyl, oxadiazolyl, 1, 2, 3-oxadiazolyl, 1, 2, 4-oxadiazolyl, 1, 2, 5-oxadiazolyl, 1, 3, 4-oxadiazolyl, oxazolidinyl, oxazolyl, hydroxindolyl, pyrimidinyl, phenanthridinyl, phenanthrolinyl, phenazine, phenothiazine, benzoxanthinyl, phenoloxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyrido-oxazolyl, pyrido-imidazolyl, pyrido-thiazolyl, pyridinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1, 2, 5-thiadiazinyl, 1, 2, 3-thiadiazolyl, 1, 2, 4-thiadiazolyl, 1, 2, 5-thiadiazolyl, 1, 3, 4-thiadiazolyl, thianthrenyl, thiazolyl, isothiazolylthienyl, thienyl, thieno-oxazolyl, thieno-thiazolyl, thieno-imidazolyl, thienyl, triazinyl, 1H-1, 2, 3-triazolyl, 2H-1, 2, 3-triazolyl, 1H-1, 2, 4-triazolyl, 4H-1, 2, 4-triazolyl, and xanthenyl. Also included are fused-ring compounds and spiro compounds.

Unless otherwise specified, the term "hydrocarbyl" or its subconcept (e.g. alkyl, alkenyl, alkynyl, and aryl, etc.), by itself or as part of another substituent, refers to a linear, branched chain or cyclic hydrocarbon radical or any combination thereof. They can be fully saturated (such as alkyl), mono- or polyunsaturated (such as alkenyl, alkynyl or aryl), can be mono-, di- or poly-substituted, can be monovalent (such as methyl), divalent (such as methylene) or multivalent (such as methenyl), can also include a divalent or multivalent group, have a specified number of carbon atom (for example, $C_1$-$C_{12}$ indicates 1 to 12 carbon atom, $C_{1-12}$ is selected from $C_1$, $C_2$, $C_3$, $C_4$, $C_5$, $C_6$, $C_7$, $C_8$, $C_9$, $C_{10}$, $C_{11}$ and $C_{12}$; $C_{3-12}$ is selected from $C_3$, $C_4$, $C_5$, $C_6$, $C_7$, $C_8$, $C_9$, $C_{10}$, $C_{11}$ and $C_{12}$.). The term "hydrocarbyl" includes, but is not limited to aliphatic hydrocarbyl and aromatic hydrocarbyl. The aliphatic hydrocarbyl includes linear and cyclic hydrocarbyl, specifically includes but not limited to alkyl, alkenyl, and alkynyl. The aromatic hydrocarbyl includes but is not limited to 6-12 membered aromatic hydrocarbyl such as phenyl, naphthyl and the like. In some embodiments, the term "hydrocarbyl" refers to a linear or branched group or a combination thereof which can be fully saturated, mono- or polyunsaturated, and can include a divalent or multivalent group. Examples of the saturated hydrocarbyl group include, but are not limited to, methyl, ethyl, n-propyl, isopropyl, n-butyl, tert-butyl, isobutyl, sec-butyl, cyclohexyl, (cyclohexyl) methyl, cyclopropylmethyl, and the homolog or isomer of n-amyl, n-hexyl, n-heptyl, n-octyl and other atom groups. The unsaturated hydrocarbyl has one or more than one double or triple bonds. Examples of the unsaturated alkyl include but are not limited to, vinyl, 2-propenyl, butenyl, crotyl, 2-isopentenyl, 2-(butadienyl), 2, 4-pentadienyl, 3-(1, 4-pentadienyl), ethynyl, 1- and 3-propynyl, 3-butynyl, and more higher homologs and isomers.

Unless otherwise specified, the term "heterohydrocarbyl" or its subconcept (such as heteroalkyl, heteroalkenyl, heteroalkynyl, and heteroaryl, etc.), by itself or as part of another substituent, refers to a stable linear, branched or cyclohydrocarbyl or any combination thereof, which has a specified number of carbon atom and at least one heteroatom. In some embodiments, the term "heteroalkyl" by itself or in combination with another term refers to a stable linear chain, branched hydrocarbon radical or a combination thereof which has a specified number of carbon atom and at least one heteroatom. In a specific embodiment, a heteroatom is selected from B, O, N and S, wherein nitrogen and sulfur atom are optionally oxidized and the nitrogen atom is optionally quaternized. The heteroatom or heteroatom group can be located at any interior position of a heterohydrocarbyl, including the position where the hydrocarbyl attaches to the rest part of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —$CH_2$—CH=N—OCH$_3$ and —CH=CH—N($CH_3$)—$CH_3$. Up to two consecutive heteroatom can be present, such as, —$CH_2$—NH—OCH$_3$.

Unless otherwise specified, the term "cyclohydrocarbyl", "heterocyclohydrocarbyl" or its subconcept (such as aryl, heteroaryl, cycloalkyl, heterocycloalkyl, cycloalkenyl, heterocycloalkenyl, cycloalkynyl, heterocycloalkynyl, etc.) by itself or in combination with another term refers to cyclized "hydrocarbyl" or "heterohydrocarbyl". Besides, for the heterohydrocarbyl and heterocyclohydrocarbyl (such as heteroalkyl and heterocycloalkyl), the heteroatom could be located in the position other than where the heterocycle is attached to the molecule. Examples of the cycloalkyl include, but are not limited to, cyclopentyl, cyclohexyl, 1-cyclohexenyl, 3-cyclohexenyl, cycloheptyl and the like. Non-limiting examples of heterocycloalkyl include 1-(1, 2, 5, 6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydro-thiophen-2-yl, tetrahydro-thiophen-3-yl, 1-piperazinyl and 2-piperazinyl.

Unless otherwise specified, the term "alkyl" refers to a linear chain or branched saturated hydrocarbon group, can be mono-substituted (e.g. —$CH_2$F) or poly-substituted (e.g. —$CF_3$), can be monovalent (e.g. methyl), divalent (e.g. methylene) or multivalent (e.g. methenyl). Examples of alkyl include methyl (Me), ethyl (Et), propyl (such as n-propyl and isopropyl), butyl (such as n-butyl, isobutyl, s-butyl, t-butyl), pentyl (such as n-pentyl, isopentyl, neopentyl) and the like.

Unless otherwise specified, the term "alkenyl" refers to a alkyl having one or more than one carbon-carbon double bond at any position, which can be mono or multiple substituted and can be monovalent, divalent or multivalent. Examples of the "alkenyl" includes vinyl, propenyl, butenyl, pentenyl, hexenyl, m-butadienyl, m-pentadienyl, m-hexadienyl etc.

Unless otherwise specified, the term "alkynyl" refers to a alkyl having one or more than one carbon-carbon triple bond at any position, which can be mono or multiple substituted and can be monovalent, divalent or multivalent. Examples of the "alkynyl" includes ethynyl, propynyl, butynyl, pentynyl etc.

Unless otherwise specified, cycloalkyl includes any stable cyclic or polycyclic hydrocarbyl, and any carbon atom is saturated, can be mono-substituted or poly-substituted, and can be monovalent, divalent or multivalent. Examples of cycloalkyl include, but are not limited to, cyclopropyl, norbornanyl, [2.2.2]bicyclooctane, [4.4.0]bicyclodecanyl and the like.

Unless otherwise specified, cycloalkenyl includes any stable cyclic or polycyclic hydrocarbyl, the hydrocarbyl contains one or more C=C double bond in any position on the ring, it can be mono- or poly-substituted, can be monovalent, divalent or multivalent. Examples of the cycloalkenyl includes, but are not limited to cyclopentenyl and cyclohexenyl etc.

Unless otherwise specified, cycloalkynyl includes any stable cyclic or polycyclic hydrocarbyl, the hydrocarbyl contains one or more C—C triple bond in any position on the ring, it can be mono- or poly-substituted, can be monovalent, divalent or multivalent.

Unless otherwise specified, the term "halo" or "halogen" by itself or as part of another substituent refers to fluorine, chlorine, bromine or iodine atom. Furthermore, the term "haloalkyl" is meant to include monohaloalkyl and polyhaloalkyl. For example, the term "halo ($C_1$-$C_4$) alkyl" is meant to include, but not limited to, trifluoromethyl, 2, 2, 2-trifluoroethyl, 4-chlorobutyl, 3-bromopropyl and the like.

Unless otherwise specified, examples of haloalkyl includes but not limited to trifluoromethyl, trichloromethyl, pentafluoroethyl, and pentachloroethyl.

"Alkoxy" represents the above alkyl group having a specified number of carbon atoms linked by an oxygen bridge, and unless otherwise specified, $C_{1-6}$ alkoxy includes alkoxy groups of $C_1$, $C_2$, $C_3$, $C_4$, $C_5$ and $C_6$. Examples of alkoxy groups include, but are not limited to, methoxy, ethoxy, n-propoxy, isopropoxy, n-butoxy, sec-butoxy, tert-butoxy, n-pentyloxy and S-pentyloxy.

Unless otherwise specified, the term "aryl" refers to a polyunsaturated aromatic substituent, can be mono-, di- or poly-substituted, can be a monovalent, divalent or multivalent, can be a single ring or a multiple ring (e.g. one to three rings; wherein at least one ring is aromatic), which are fused together or connected covalently. The term "heteroaryl" refers to an aryl (or ring) containing one to four heteroatom. In an illustrative example, the heteroatom is selected from B, O, N and S, wherein nitrogen and sulfur atom are optionally oxidized and nitrogen atom is optionally quaternized. A heteroaryl may attach to the rest part of a molecule via a heteroatom. Non-limiting examples of aryl or heteroaryl include phenyl, naphthyl, biphenyl, pyrrolyl, pyrazolyl, imidazolyl, pyrazinyl, oxazolyl, phenyl-oxazolyl, isoxazolyl, thiazolyl, furanyl, thienyl, pyridyl, pyrimidinylbenzothiazolyl, purinyl, benzimidazolyl, indolyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl. The substituent of any of the above aryl and heteroaryl ring system is selected from the acceptable substituent described below.

Unless otherwise specified, when combined with other term (such as aryloxy, arylthio, arylalkyl), the aryl includes the aryl and heteroaryl ring as defined above. Thus, the term "aralkyl" is meant to include the group (e.g. benzyl, phenethyl, pyridylmethyl, etc.) where an aryl is attached to an alkyl, including an alkyl where the carbon atom (e.g. methylene) has been replaced by an atom such as oxygen, for example, phenoxymethyl, 2-pyridyloxy, 3-(1-naphthyloxy) propyl, and the like.

Unless otherwise specified, the term "leaving group" refers to a functional group or atom which can be replaced by another functional group or atom through a substitution reaction (such as affinity substitution reaction). For example, representative leaving groups include triflate; chlorine, bromine and iodine; sulfonate group, such as mesylate, tosylate, p-bromobenzenesulfonate, p-toluenesulfonates and the like; acyloxy, such as acetoxy, trifluoroacetoxy and the like.

Unless otherwise specified, the term "protecting group" includes, but is not limited to "amino protecting group", "hydroxy protecting group" or "thio protecting group". The term "amino protecting group" refers to a protecting group suitable for blocking the side reaction on the nitrogen of an amino. Representative amino protecting groups include, but are not limited to: formyl; acyl, such as alkanoyl(e.g. acetyl, trichloroacetyl or trifluoroacetyl); alkoxycarbonyl, such as tert-butoxycarbonyl (Boc); arylmethoxycarbonyl such as benzyloxycarbonyl (Cbz) and 9-fluorenylmethoxycarbonyl (Fmoc); arylmethyl such as benzyl (Bn), trityl (Tr), 1,1-bis-(4'-methoxyphenyl) methyl; silyl such as trimethylsilyl (TMS) and tert-butyldimethylsilyl (TBS) and the like. The term "hydroxy protecting group" refers to a protecting group suitable for blocking the side reaction on hydroxy. Representative hydroxy protecting groups include, but are not limited to: alkyl such as methyl, ethyl and tert-butyl; acyl such as alkanoyl (e.g. acetyl); arylmethyl such as benzyl (Bn), p-methoxybenzyl (PMB), 9-fluorenylmethyl (Fm), and diphenylmethyl (benzhydryl, DPM); silyl such as trimethylsilyl (TMS) and tert-butyl dimethyl silyl (TBS) and the like.

The compound of the present invention can be prepared by various of synthetic methods known by the man skilled in the art, including the embodiments below, the combination thereof with other chemical synthetic methods and equivalent alternatives known by the man skilled in the art, preferred embodiments include, but are not limited to the embodiments of the present invention.

The solvents used in the present invention are commercially available, the present invention employed the following abbreviations: aq represents water; HATU represents O-(7-azabenzotriazol-1-yl)-N,N,N,N-tetramethyluronium hexafluorophosphate; EDC represents N-(3-dimethylaminopropyl)-N'-ethylcarbodiimide hydrochloride; m-CPBA represents 3-chloroperoxybenzoic acid; eq represents equivalent or equivalence; CDI represents carbonyl diimidazole; DCM represents dichloromethane; PE represents petroleum ether; DIAD represents diisopropyl azodicarboxylate; DMF represents N, N-dimethylformamide; DMSO represents dimethylsulfoxide; EtOAc represents ethyl acetate; EtOH represents ethanol; MeOH represents methanol; CBz represents benzyloxycarbonyl, which is an amino protecting group; BOC represents tert-butylcarbonyl, which is an amino protecting group; HOAc represents acetic acid; NaCNBH$_3$ represents sodium cyanoborohydride; r.t. represents room temperature; O/N represents overnight; THF represents tetrahydrofuran; Boc$_2$O represents di-tert-butyl-dicarbonate; TFA represents trifluoroacetic acid; DIPEA represents diisopropylethylamine; SOCl$_2$ represents thionyl chloride; CS$_2$ represents carbon disulfide; TsOH represents p-toluenesulfonic acid; NFSI represents N-fluoro-N-(benzenesulfonyl)-benzsulfamide; NCS represents 1-chloropyrrolidine-2, 5-dione; n-Bu$_4$NF represents tetrabutylammonium fluoride; iPrOH represents 2-propanol; mp represents melting point; LDA represents lithium diisopropylamide; EA represents ethyl acetate; DPPF represents 1, 1'-bisdiphenylphosphinoferrocene; Et represents ethyl; Me represents methyl; DCM represents dichloromethane; TMSCHN$_2$ represents trimethylsilylated diazomethane; DCE represents dichloroethane; BSA represents bovine serum albumin; TCEP represents tris(2-carboxyethyl) phosphine; BH$_3$-Me$_2$S represents borane methyl sulfide; Pd(OAc)$_2$ represents palladium acetate; DPPP represents 1,3-bis(diphenylphosphino) propane; TEA represents triethylamine; TMSCl represents trimethylchlorosilane; EDCI represents 1-(3-dimethylaminopropyl)-3-ethylcarbodiimide hydrochloride; Et3N represents triethylamine; MeI represents Methyl iodide; KHMDS represents hexamethyldisilazide potassium; n-BuLi represents n-butyllithium; Pd$_2$(dba)$_3$ represents tris (dibenzylideneacetone) dipalladium; t-BuXPhOS represents 2-di-tert butylphosphino-2',4',6'-triisopropyl linkage; DIEA represents N,N-diisopropylethylamine.

Compounds are named manually or by ChemDraw® software, the commercially available compounds use their vendor directory names.

DETAILED DESCRIPTION OF THE PREFERRED EMBODIMENT

The following examples further illustrate the present invention, but the present invention is not limited thereto.

The present invention has been described in detail herein, wherein the specific embodiments thereof has been disclosed, for the man skilled in the art, it's obvious that various modifications and improvements could be made to the embodiments of the present invention without departing from the spirit and scope of the present invention.

Embodiment 1

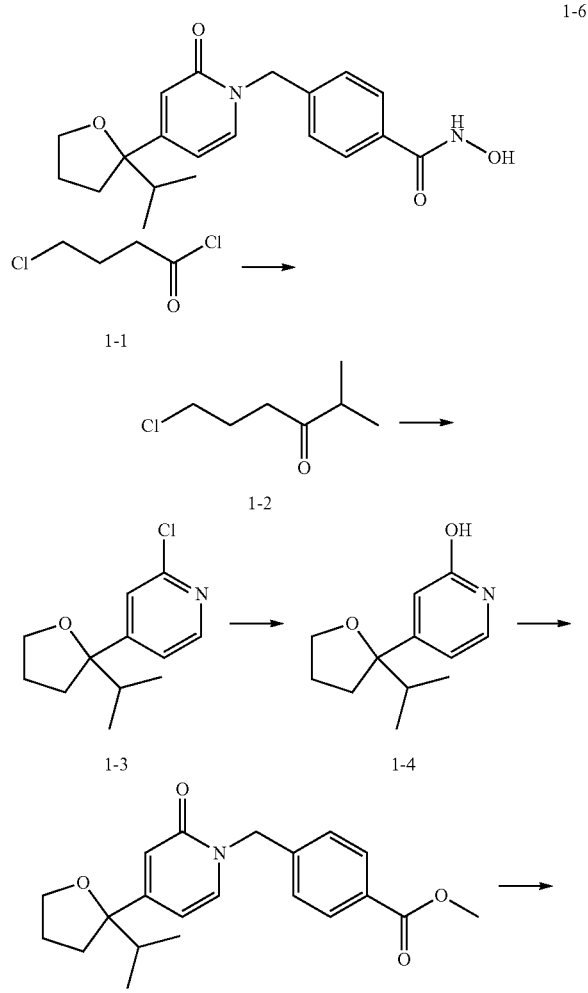

step 1: Compound 1-1 (11.30 g, 80.14 mmol) was added into anhydrous THF (120.00 mL), then iPrMgCl (2M, 40.07 mL) was added dropwise at −78° C., and stirred at 15° C. for 16 hours under nitrogen atmosphere. When the reaction was completed, saturated NH₄Cl (50 mL) was added, then after extraction and concentration, the residue was purified by silica gel chromatography to give the compound 1-2. ¹HNMR (400 MHz, CDCl₃) δ 3.57 (t, J=6.0 Hz, 2H), 2.59~2.66 (m, 3H), 2.02~2.07 (m, 2H), 1.11 (d, J=6.8 Hz, 6H).

step 2: Compound 1-2 (3.70 g, 24.89 mmol) and 2-chloro-4-bromopyridine (4.79 g, 24.89 mmol) were added into anhydrous THF (50.00 mL), then n-BuLi (2.5 M, 9.96 mL) was added dropwise at −78° C., and stirred at 20° C. for 18 hours under nitrogen protection. After the completion of the reaction, saturated NH₄Cl was added, followed by extraction and concentration, the residue was purified by silica gel chromatography to give the compound 1-3. ¹HNMR (400 MHz, CDCl₃) δ 8.31 (d, J=6.8 Hz, 1H), 7.33 (d, J=1.6 Hz, 1H), 7.15~7.19 (m, 1H), 3.92~3.98 (m, 1H), 3.75~3.81 (m, 1H), 2.08-2.17 (m, 2H), 1.89~2.01 (m, 2H), 1.60~1.72 (m, 2H), 0.78 (d, J=6.8 Hz, 3H), 0.72 (d, J=6.8 Hz, 3H).

Step 3: Compound 1-3 (1.60 g, 7.09 mmol), KOH (795.64 mg, 14.18 mmol) was added into the mixed solvent of dioxane (15.00 mL)/H₂O (5.00 mL), then Pd₂(dba)₃ (324.62 mg, 354.50 μmol) and tBuXPhOS (301.07 mg, 709.00 μmol) were added and stirred at 115° C. for 18 hours under nitrogen protection. After the completion of the reaction, the mixture was diluted by water and extracted by EtOAc, the extract was dried by brine and anhydrous and then concentrated to give the compound 1-4. MS ESI calculated value C₁₂H₁₆ClNO [M+H]⁺ 208, measured value 208.

Step 4: Compound 1-4 (200.00 mg, 964.92 μmol) was added into anhydrous DMF (50.00 mL), then NaH (60%, 57.90 mg, 1.45 mmol) was added at 0° C., and stirred at 25° C. for 0.5 hours, then methyl 4-bromomethylbenzoate (221.04 mg, 964.92 μmol) was added at 0° C. and stirred at 25° C. for 0.5 hours. After the completion of the reaction, 20 mL water was added and the residue was filtered off and dried then purified by column chromatography to give the compound 1-5. MS ESI calculated value C₂₁H₂₅NO₄ [M+H]⁺ 356, measured value 356.

Step 5: Compound 1-5 (100 mg, 281.35 μmol) was added into the mixed solvent DCM/H₂O (15.00 mL), then 2M NaOH (2 mL) was added at 0° C., followed by addition of 50% NH₂OH (2 mL), and then stirred at 25° C. for 0.5 hours. Preparative HPLC was used for separation to give the target compound 1-6. ¹H NMR (400 MHz, MeOD) δ 7.74 (d, J=8.0 Hz, 2H), 7.68 (d, J=6.8 Hz, 1H), 7.40 (d, J=8.0 Hz, 2H), 6.61 (d, J=0.8 Hz, 1H), 6.46 (dd, J=6.8 Hz & 0.8 Hz, 1H), 5.25 (s, 2H), 3.91~3.97 (m, 1H), 3.79~3.84 (m, 1H), 2.10~2.19 (m, 3H), 2.01~2.05 (m, 1H), 1.79~1.94 (m, 1H), 0.95 (d, J=7.2 Hz, 3H), 0.83 (d, J=7.2 Hz, 3H). MS ESI calculated value C₂₀H₂₄N₂O₄ [M+H]⁺ 357, measured value 357.

Embodiment 2

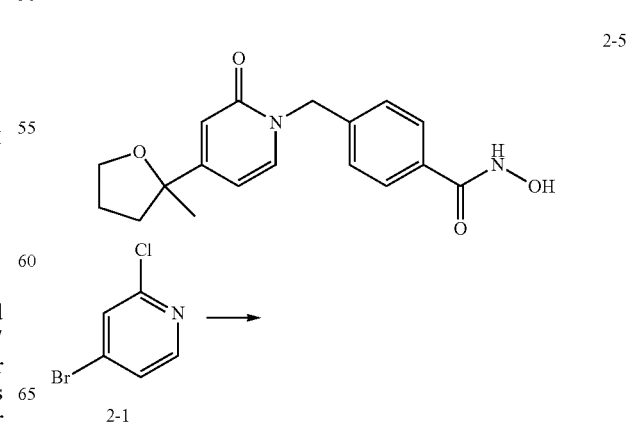

-continued

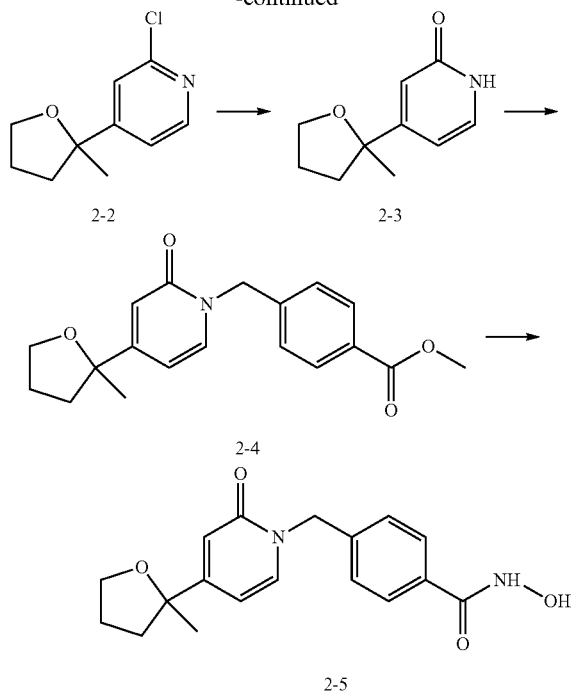

Step 1: At −78° C. and under nitrogen atmosphere, N-butyllithium (2.5 M, 24.94 mL, 1.20 eq) was added dropwise into the compound 2-1 (10.00 g, 51.96 mmol, 1.00 eq) and 5-chloropentan-2-one (6.27 g, 51.96 mmol, 1.00 eq) in tetrahydrofuran (100.00 mL), and then stirred at −78-15° C. for 5 hours under nitrogen atmosphere. The reaction solution was then concentrated and dispersed in water (100 mL) and EtOAc (100 mL), after extraction, the organic phases were combined and washed by saturated brine (100 mL*3), dried by $Na_2SO_4$, concentrated and then purified by silica get column to give the compound 2-2. MS ESI calculated value $C_{10}H_{12}ClNO$ [M+H]$^+$ 198, measured value 198.

Step 2: Under nitrogen atmosphere, $Pd_2(dba)$ 3 (1.39 g, 1.52 mmol, 0.10 eq) and t-BuXphos (1.29 g, 3.04 mmol, 0.20 eq) were added into the compound 2-2 (3.00 g, 15.18 mmol, 1.00 eq) and potassium hydroxide (1.28 g, 22.77 mmol, 1.50 eq) in dioxane (15.00 mL) and water (3.00 mL) solution. Ater 3 times of nitrogen displacement, the mixture was stirred at 110° C. for 12 hours under nitrogen atmosphere. The reaction mixture was suction filtered and was added into water, then extracted by dichloromethane:methanol (10:1, 20 mL*3), washed by saturated brine and dried over sodium sulfate, then concentrated and purified by silica gel column to give the compound 2-3. MS ESI calculated value $C_{10}H_{13}NO$ [M+H]$^+$ 180, measured value 180.

Step 3: Compound 2-3 (230.00 mg, 1.28 mmol, 1.00 eq), methyl 4-(bromomethyl) benzoate (293.97 mg, 1.28 mmol, 1.00 eq), barium carbonate (627.21 mg, 1.93 mmol, 1.50 eq) and potassium iodide (10.65 mg, 64.17 μmol, 0.05 eq) in tetrahydrofuran (20.00 mL) was displaced by nitrogen for 3 times, and then stirred at 66° C. for 12 hours under nitrogen atmosphere. The reaction mixture was concentrated, dissolved in water then extracted by EtOAc, after washed by saturated brine, it was dried over sodium sulfate and concentrated to give the compound 2-4. MS ESI calculated value $C_{19}H_{21}NO_4$ [M+H]$^+$ 328, measured value 328.

Step 4: At 0° C. under nitrogen atmosphere, sodium hydroxide solution (2 M, 2.29 mL, 5.00 eq) was added dropwise into the compound 2-4 (300.00 mg, 916.39 μmol, 1.00 eq) in methanol (15.00 mL). The reaction mixture was stirred at 15° C. for 2.5 hours. Then the reaction mixture was concentrated and dissolved into water (15 mL), extracted by dichloromethane:methanol (10:1, 15 mL*3), and washed by saturated brine, then dried over sodium sulfate, followed by concentration, finally purified by preparative HPLC to give the compound 2-5. $^1$H NMR (400 MHz, $CDCl_3$) δ 7.40 (m, 2H), 7.19 (d, J=7.2, 1H), 6.87 (m, 2H), 6.72 (s, 1H), 6.27 (d, J=5.6 Hz, 2H), 4.01 (m, 2H), 3.86 (d, J=6.0, 2H), 2.46 (m, 2H), 2.16 (s, 2H), 1.96 (m, 2H), 1.65 (m, 4H), 1.32 (s, 4H). MS ESI calculated value $C_{18}H_{20}N_2O_4$ [M+H]$^+$ 329, measured value 329.

Embodiment 3

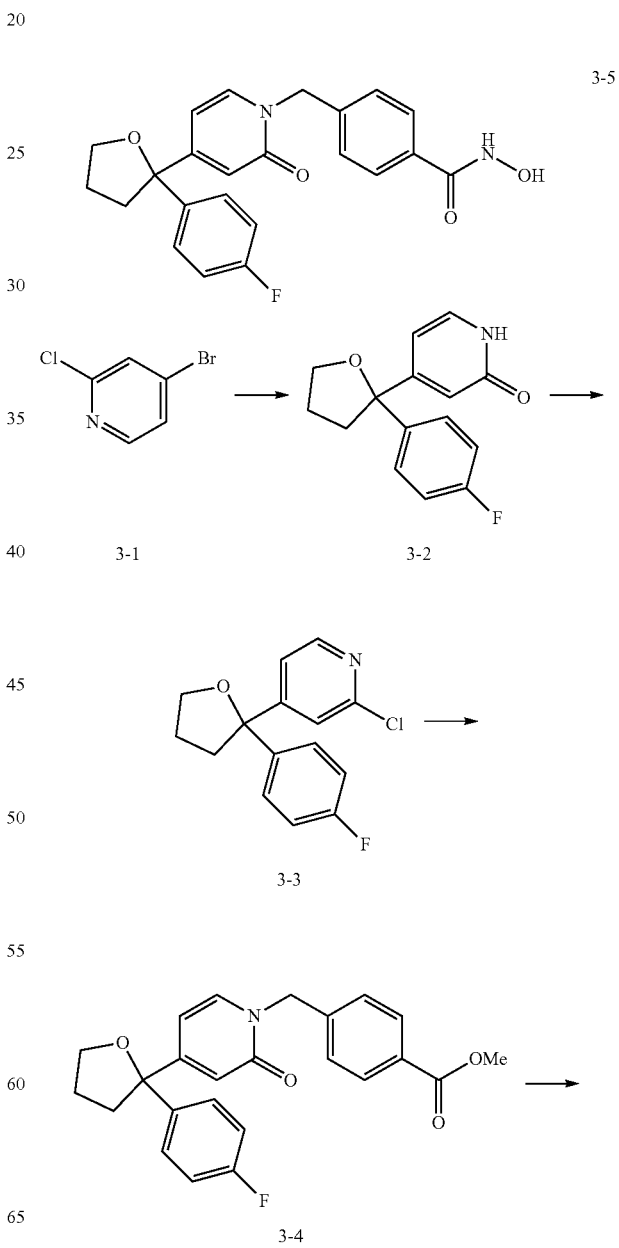

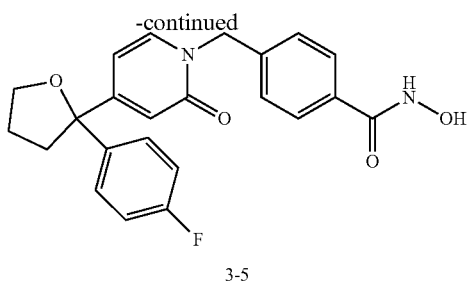

3-5

Step 1: At −65° C. to 75° C., N-butyllithium in cyclohexane solution (2.5 M, 49.89 mL, 1.20 eq) was added dropwise into 4-bromo-2-chloro-pyridine (20.00 g, 103.93 mmol, 1.00 eq) in toluene (30.00 mL), and then stirred at −65° C. to 75° C. for 1 hours, then the compound 3-1 (20.85 g, 103.93 mmol, 17.09 mL, 1.00 eq) in toluene (100.00 mL) solution was added into the reaction system, the temperature was raised to 25° C. and stirred for 2 hours. Saturated ammonium chloride solution was added into the reaction mixture, then extracted by EtOAc, then dried over anhydrous sodium sulfate, followed by filtration and concentration. After concentrated, the solution was purified by silica gel column to give the compound 3-2. $^1$H NMR (400 MHz, CDCl$_3$) δ 8.29 (d, J=5.3 Hz, 1H), 7.43-7.37 (m, 3H), 7.24 (dd, J=1.6, 5.2 Hz, 1H), 7.06-7.00 (m, 2H), 4.13-4.00 (m, 2H), 2.64-2.56 (m, 1H), 2.46 (m, 1H), 2.04-1.91 (m, 2H). MS ESI calculated value C$_{15}$H$_{13}$ClFNO [M+H]+ 278, measured value 278.

Step 2: The temperature of the reaction mixture formed by compound 3-2 (8.50 g, 30.61 mmol, 1.00 eq), potassium hydroxide (3.44 g, 61.22 mmol, 2.00 eq), tris(dibenzylideneacetone) dipalladium (5.61 g, 6.12 mmol, 0.20 eq) and 2-di-tert-butylphosphine-2', 4', 6'-triisopropylbiphenyl (2.60 g, 6.12 mmol, 0.20 eq) in dioxane (2.00 mL) and water (1.00 mL) was raised to 100° C. and the mixture was stirred for 2 hours. 1M dilute hydrochloric acid was added into the reaction mixture to adjust the PH to 7, then water was added, EtOAc was used for extraction and then the mixture was dried over anhydrous sodium sulfate, filtered and concentrated to give the crude product. The mixture was then slurry purify (打浆纯化) to give the compound 3-3. $^1$H NMR (400 MHz, CDCl$_3$) δ 12.84 (brs, 1H), 7.40 (dd, J=5.3, 8.7 Hz, 2H), 7.25 (d, J=6.8 Hz, 1H), 7.01 (t, J=8.8 Hz, 2H), 6.69 (s, 1H), 6.29 (dd, J=1.4, 6.8 Hz, 1H), 4.12-3.98 (m, 2H), 2.48 (t, J=7.2 Hz, 2H), 1.98 (m, 2H), 1.25 (dd, J=6.9, 9.5 Hz, 2H). MS ESI calculated value C$_{15}$H$_{14}$FNO$_2$ [M+H]$^+$ 260, measured value 260.

Step 3: At 0-5° C., sodium hydride (1.08 g, 27.00 mmol, purity 60%, 1.00 eq) was added into the compound 3-3 (7.00 g, 27.00 mmol, 1.00 eq) in N, N-dimethylformamide (70.00 mL) solution, and stirred at 0-5° C. for 10 mins, Then methyl 4-bromomethylbenzoate (6.18 g, 27.00 mmol, 1.00 eq) in N, N-dimethylformamide (20.00 mL) was added into the reaction system, and stirred at 10-25° C. for 2 mins. Saturated ammonium chloride solution was added into the reaction mixture, extracted with EtOAc and dried over anhydrous sodium sulfate then concentrated. After concentration the compound 3-4 was obtained and used directly in the next step.

Step 4: Sodium hydroxide solution (2 M, 27.00 mL, 2.00 eq) and oxyammonia solution (1.00 mL, 50% purity) were added into the mixture of the compound 3-4 (11.00 g, 27.00 mmol, 1.00 eq), oxyammonia solution (100.00 mL, 50% purity), methanol (20.00 mL) and dichloromethane (10.00 mL), the temperature was raised to 40-50° C., and stirred for 1 hours. After the reaction mixture was concentrated, 1M hydrochloric acid was added to adjust the PH to 7, and then extracted by dichloromethane, After concentration, reverse phase preparative HPLC was used for purification to give the compound 3-5. $^1$H NMR (400 MHz, D MSO-d$_6$) δ 11.17 (s, 1H), 9.04 (br s, 1H), 7.74-7.64 (m, 3H), 7.55-7.45 (m, 2H), 7.32 (d, J=8.3 Hz, 2H), 7.14 (t, J=8.9 Hz, 2H), 6.50 (d, J=1.9 Hz, 1H), 6.25 (dd, J=2.0, 7.2 Hz, 1H), 6.29-6.22 (m, 1H), 5.05 (s, 2H), 3.98-3.83 (m, 2H), 2.48-2.41 (m, 2H), 1.85 (m, 2H). MS ESI calculated value C$_{23}$H$_{21}$FN$_2$O$_4$ [M+H]$^+$ 409, measured value 409.

Embodiment 4

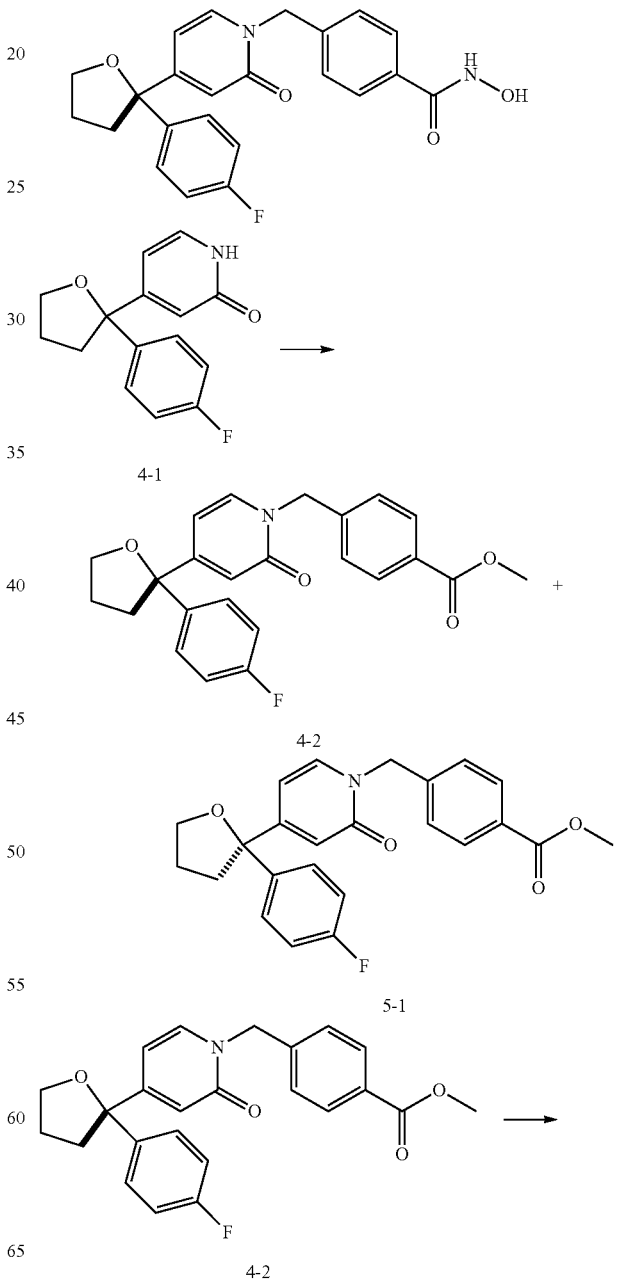

4-3(P1)

4-1

4-2

5-1

4-2

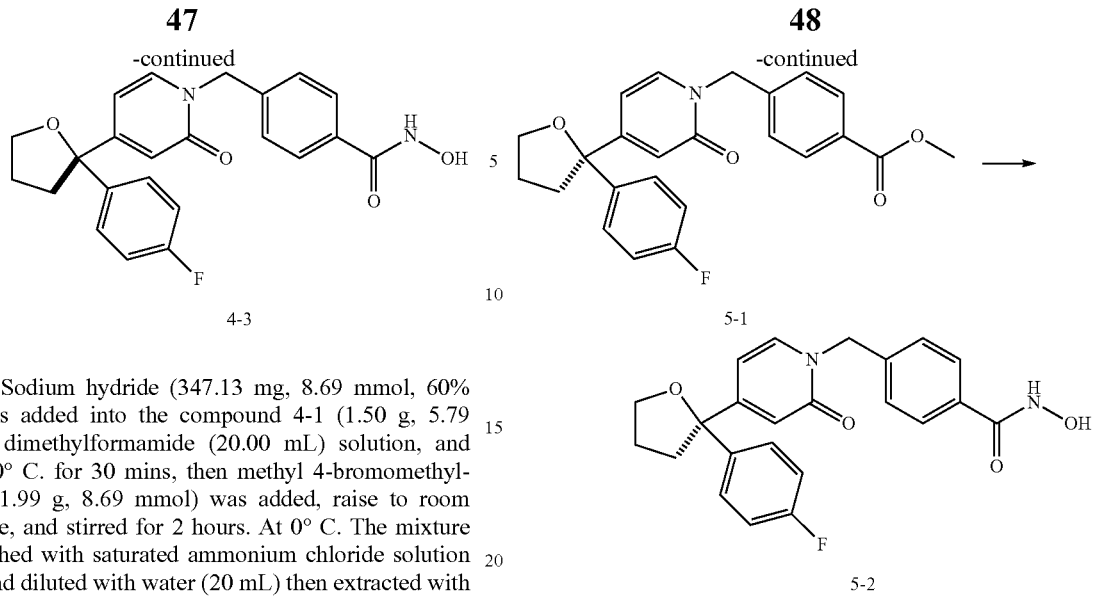

4-3

Step 1: Sodium hydride (347.13 mg, 8.69 mmol, 60% purity) was added into the compound 4-1 (1.50 g, 5.79 mmol) in dimethylformamide (20.00 mL) solution, and stirred at 0° C. for 30 mins, then methyl 4-bromomethyl-benzoate (1.99 g, 8.69 mmol) was added, raise to room temperature, and stirred for 2 hours. At 0° C. The mixture was quenched with saturated ammonium chloride solution (15 mL) and diluted with water (20 mL) then extracted with EtOAc (20 mL*4). The organic phases were combined and washed with water (20 mL*2) and saturated brine (20 mL*1), then dried and concentrated, purified with silica get column chromatography (PE/EtOAc=3/1, 1:1 to 0/1) to give the crude product. The mixture of crude product was chiral resoluted (chiral column type: OJ (250 mm*30 mm, 10 μm); mobile phase: A: CO2 B: 0.05% diethylamine/EtOH, EtOH (0.05% diethylamine) with supercritical fluid CO2 from 5% to 40%, flow velocity 60 mL/min), after resolution, the compound 4-2 and the compound 5-1 was obtained, remaining times were 2.226 min and 2.835 min respectively. The compound 4-2 has 1H NMR (400 MHz, D MSO-d6) δ=7.95-7.88 (m, 2H), 7.71 (d, J=7.2 Hz, 1H), 7.54-7.46 (m, 2H), 7.38 (d, J=8.4 Hz, 2H), 7.19-7.09 (m, 2H), 6.51 (d, J=2.0 Hz, 1H), 6.27 (dd, J=2.0, 7.2 Hz, 1H), 5.09 (s, 2H), 3.98-3.85 (m, 2H), 3.83 (s, 3H), 2.49-2.41 (m, 2H), 1.91-1.75 (m, 2H). MS ESI calculated value C24H22FNO4 [M+H]+ 407.43, measured value 408.1.

Step 2: Sodium hydroxide (103.20 mg, 2.58 mmol) and hydroxylamine (5.00 mL, 50% solution) were added into the compound 4-2 (700.00 mg, 1.72 mmol) in methanol (5.00 mL) solution, then stirred at rt for 30 mins. After concentration, diluted hydrochloric acid (1M) was added to adjust pH to 7, then purified by reverse phase preparative HPLC (0.225% FA) to give the compound 4-3. $^1$H NMR (400 MHz, D MSO-d6) δ=11.49-10.50 (br s, 1H), 9.04 (br s, 1H), 7.69 (m, 3H), 7.49 (m, 2H), 7.33 (m, 2H), 7.14 (m, 2H), 6.50 (m, 1H), 6.25 (m, 1H), 5.05 (s, 2H), 3.90 (m, 2H), 2.45 (m, 2H), 1.85 (m, 2H). MS ESI calculated value $C_{23}H_{21}N_2O_4F$ [M+H]$^+$ 408.42, measured value 408.9.

Embodiment 5

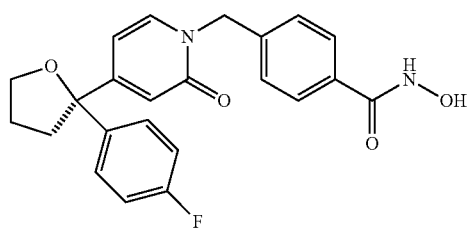

5-2

Step 1: Sodium hydroxide (132.60 mg, 3.32 mmol) and hydroxylamine (5.00 mL, 50% solution) were added into the compound 5-1 (900.00 mg, 2.21 mmol) in methanol (5.00 mL) solution, then stirred at rt for 30 mins. The mixture was concentrated and was added diluted hydrochloric acid 1M) to adjust the pH to 7, then extracted with EtOAc (50 mL*4), the organic phases were combined and concentrated, then purified by reverse phase preparative HPLC ((0.225% FA) to give the compound 5-2. $^1$H NMR (400 MHz, D MSO-d$_6$) δ 12.07-10.09 (br s, 1H), 9.08 (br s, 1H), 7.68 (m, 3H), 7.56-7.44 (m, 2H), 7.32 (m, 2H), 7.14 (m, 2H), 6.50 (m, 1H), 6.25 (m, 1H), 5.01 (s, 2H), 4.09-3.74 (m, 2H), 2.45 (m, 2H), 1.94-1.76 (m, 2H). MS ESI calculated value $C_{23}H_{21}N_2O_4F$ [M+H]$^+$ 408.42, measured value 408.8.

Embodiment 6

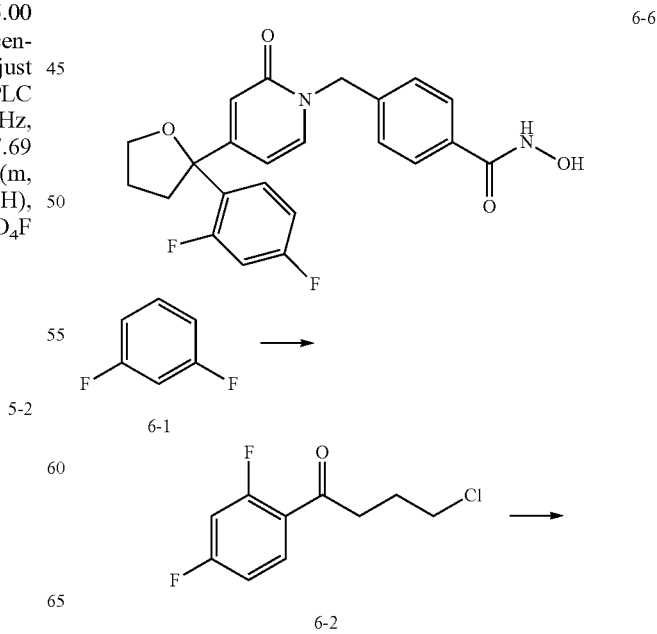

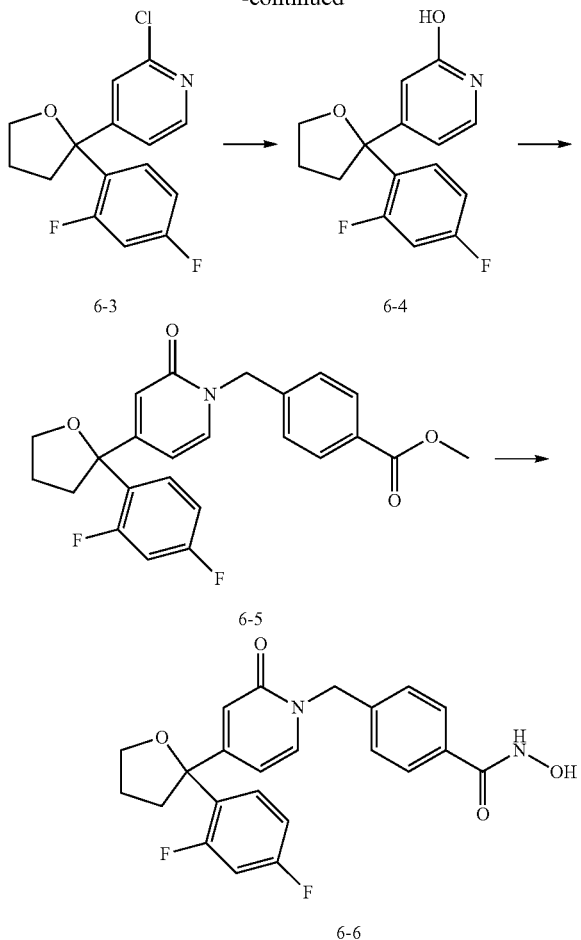

1.00 eq) in dioxane (2.00 mL) and water (1.00 mL) solution, then stirred at 80° C. for 3 hours. Water was added into the reaction mixture, then the mixture was extracted by EtOAc, washed by saturated brine, dried over anhydrous sodium sulfate and filtrated and concentrated. After concentration, TLC plate was used for purification to give the compound 6-4. MS ESI calculated value $C_{15}H_{13}F_2O_2N$ $[M+H]^+$ 278, measured value 278.

Step 4: At 0° C., sodium hydride (17.31 mg, 432.80 μmol, purity 60%, 2.00 eq) was added into the compound 6-4 (60.00 mg, 216.40 μmol, 1.00 eq) in N, N-dimethylformamide (1.00 mL) solution, then methyl 4-bromomethylbenzoate (49.57 mg, 216.40 μmol, 1.00 eq) in N, N-dimethylformamide (1.00 mL) solution was added into the reaction system, then stirred at 25° C. for 2 hours. Water was added into the reaction mixture, then the mixture was extracted by EtOAc, washed by saturated brine, dried over anhydrous sodium sulfate and filtrated and concentrated. After concentration, TLC plate was used for purification to give the compound 6-5. MS ESI calculated value $C_{24}H_{21}NO_4F_2$ $[M+H]^+$ 426, measured value 426.

Step 5: Sodium hydroxide solution (6 M, 50.00 μL, 3.99 eq) and hydroxylamine solution (1.00 mL, 50% solution) were added into the compound 6-5 (32.00 mg, 75.22 μmol, 1.00 eq) in methanol (2.00 mL) solution, then stirred at 25° C. for 17 hours. After the concentration of the reaction mixture, the mixture was purified by reverse phase column to give the compound 6-6. $^1$H NMR (400 MHz, MeOD) δ ppm 1.89-2.08 (m, 2H) 2.48-2.74 (m, 2H) 3.93-4.11 (m, 2H) 5.20 (s, 2H) 6.46 (dd, J=7.09, 1.82 Hz, 1H) 6.66 (s, 1H) 6.88-7.03 (m, 2H) 7.37 (d, J=8.16 Hz, 2H) 7.63 (d, J=7.15 Hz, 1H) 7.67-7.72 (m, 2H) 7.72-7.75 (m, 1H). MS ESI calculated value $C_{23}H_{20}N_2O_4F_2$ $[M+H]^+$ 427, measured value 427.

Embodiment 7

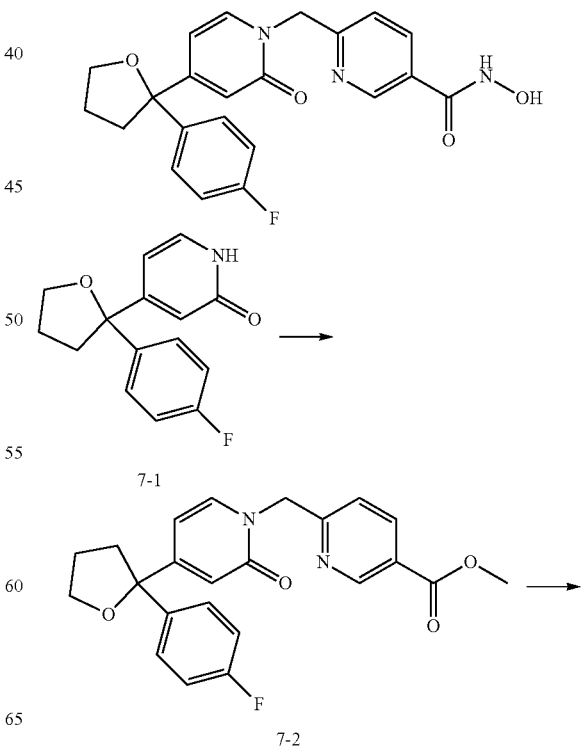

Step 1: At 5° C., 4-chlorobutyryl chloride (500.00 mg, 3.55 mmol, 396.83 μL, 0.50 eq) was added into the mixture of the compound 6-1 (809.15 mg, 7.09 mmol, 697.54 μL, 1.00 eq) and alcohol (633.60 mg, 4.75 mmol, 259.67 μL, 0.67 eq), then stirred fat 25° C. for 3 hours, the reaction mixture was added into ice water, then stirred, extracted with EtOAc, and washed by saturated brine, dried over anhydrous sodium sulfate, filtered and the filtrate was concentrated to give the compound 6-2. The liquid was used directly in the next reaction.

Step 2: At −68° C., N-butyllithium in cyclohexane solution (2.5 M, 1.21 mL, 1.10 eq) was added into 4-bromo-2-chloro-pyridine (527.29 mg, 2.74 mmol, 1.00 eq) in toluene (5.00 mL) solution, and stirred at −68° C. for 10 mins, the compound 6-2 (600.00 mg, 2.74 mmol, 1.00 eq) in toluene (5.00 mL) solution was added into the reaction system, and stirred at −68° C. for 1 hours then at 25° C. for 14 hours. Saturated ammonium chloride solution and water were added into the reaction mixture sequentially, extracted by EtOAc, then washed by saturated brine, dried over anhydrous sodium sulfate then concentrated. After concentration, TLC plate was used for purification and give the compound the compound 6-3. MS ESI calculated value $C_{15}H_{12}F_2ONCl$ [M+H]+ 296, measured value 296.

Step 3: Potassium hydroxide (33.02 mg, 588.42 μmol, 2.00 eq), tris(dibenzylideneacetone) dipalladium (26.94 mg, 29.42 μmol, 0.10 eq) and 2-di-tertbutylphosphine-2', 4', 6'-triisopropylbiphenyl (12.49 mg, 29.42 μmol, 0.10 eq) were added into the compound 6-3 (87.00 mg, 294.21 μmol,

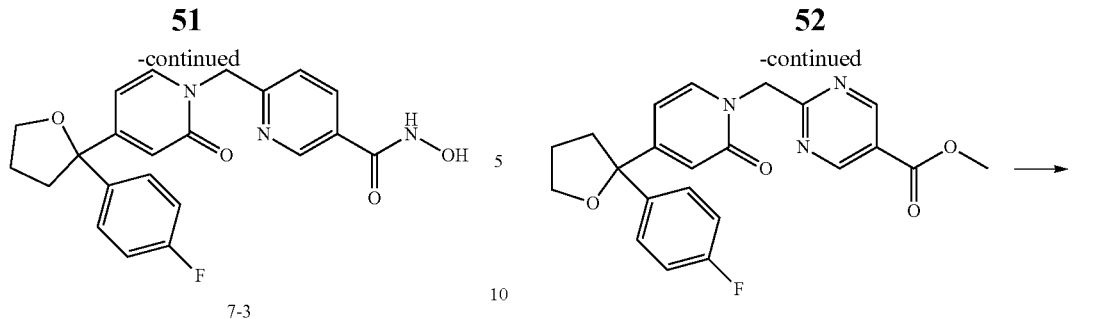

Step 1: Sodium hydride (21.60 mg, 539.98 μmol, 60% purity) was added into the compound 7-1 (70.00 mg, 269.99 μmol) in dimethylformamide (5.00 mL) solution, then stirred at 0° C. for 30 mins, and 6-bromomethyl-3-methyl formate pyridine (124.23 mg, 539.98 μmol) was added into the mixture, then stirred at 0° C. for 30 mins. The temperature was raised to rt and keep stirring for 30 mins. The mixture was added saturated ammonium chloride solution (1 mL) and water (15 mL), then extracted by EtOAc (10 mL*4). The organic phases were combined and washed by water (10 mL*3) and saturated brine (10 mL), then dried, filtered and concentrated. Separation with plate (PE/EA=1/1) gave the compound 7-2. MS ESI calculated value $C_{23}H_{21}FN_2O_4$ [M+H]$^+$ 409, measured value 409.

Step 2: Hydroxylamine (1.00 mL, 50% solution) and sodium hydroxide NaOH (6.44 mg, 161.11 μmol) were added into the compound 7-2 (70.00 mg, 161.11 μmol) in methanol (5.00 mL) solution, then stirred at rt for 30 mins. The mixture was added into diluted hydrochloric acid (1M) to adjust pH to 7, followed by purification to give the compound 7-3. $^1$H NMR (400 MHz, D MSO-d$_6$) δ 8.77 (d, J=1.8 Hz, 1H), 8.05 (dd, J=2.4, 8.2 Hz, 1H), 7.69 (d, J=7.2 Hz, 1H), 7.57-7.48 (m, 2H), 7.30 (d, J=8.2 Hz, 1H), 7.21-7.11 (m, 2H), 6.48 (d, J=1.8 Hz, 1H), 6.28 (dd, J=2.0, 7.2 Hz, 1H), 5.14 (s, 2H), 4.01-3.83 (m, 2H), 2.49-2.44 (m, 2H), 1.92-1.79 (m, 2H). MS ESI calculated value $C_{22}H_{20}FN_3O_4$ [M+H]$^+$ 410, measured value 410.

Embodiment 8

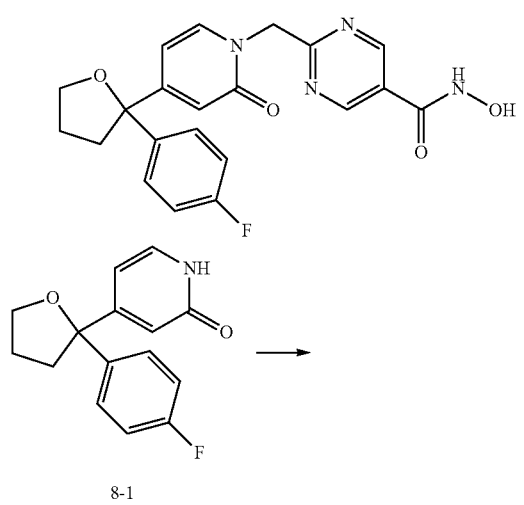

Step 1: Sodium hydride (21.60 mg, 539.98 μmol, purity 60%) was added into the compound 8-1 (70.00 mg, 269.99 μmol) in dimethylformamide (5.00 mL) solution, then stirred at 0° C. for 30 mins, Then 2-bromomethyl-5-methyl formate pyrimidine (132.33 mg, 539.98 μmol) was added and keep stirring at 0° C. for 30 mins, raised the temperature to rt and keep stirring for 30 mins. The mixture was quenched by saturated ammonium chloride (1 mL), water was added (15 mL) then extracted by EtOAc (10 mL*4). The combined organic phases were washed by water (5 mL*3) and saturated brine (10 mL), and was dried, filtered and concentrated, then purified by preparative thin layer chromatography (PE/EA=1/1) to give the compound 8-2. MS ESI calculated value C22H20FN3O4 [M+H]$^+$ 424, measured value 424.

Step 2: Hydroxylamine (1.00 mL, 50% solution) and sodium hydroxide NaOH (6.43 mg, 160.72 μmol) were added into the compound 8-2 (70.00 mg, 160.72 μmol,) in methanol (5.00 mL) solution, then stirred at 0° C. for 30 mins. The mixture was added hydrochloric acid to adjust pH to 7, then purified to give the compound 8-3. $^1$H NMR (400 MHz, D MSO-d6) δ 8.97 (s, 2H), 7.69 (d, J=7.2 Hz, 1H), 7.59-7.51 (m, 2H), 7.20-7.13 (m, 2H), 6.47 (d, J=2.0 Hz, 1H), 6.31 (dd, J=2.0, 7.2 Hz, 1H), 5.26 (s, 2H), 4.00-3.87 (m, 2H), 2.53 (m, 2H), 1.93-1.82 (m, 2H). MS ESI calculated value $C_{21}H_{19}FN_4O_4$ [M+H]$^+$ 411, measured value 411.

Embodiment 9

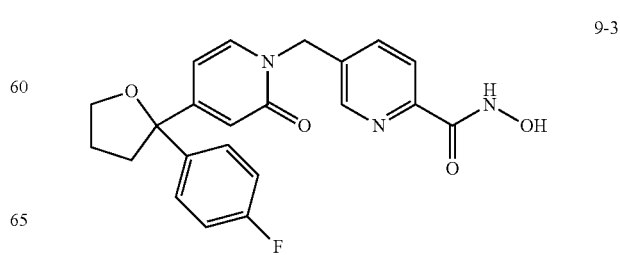

-continued

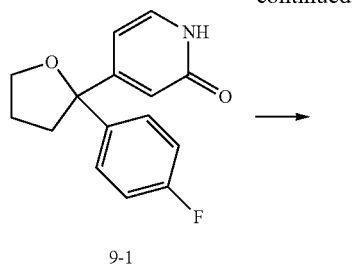

9-1

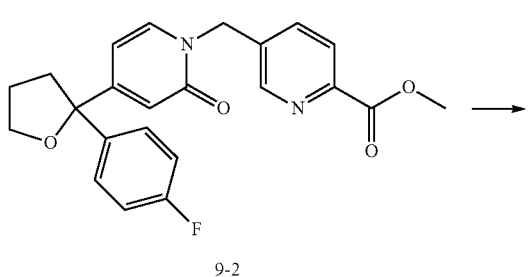

9-2

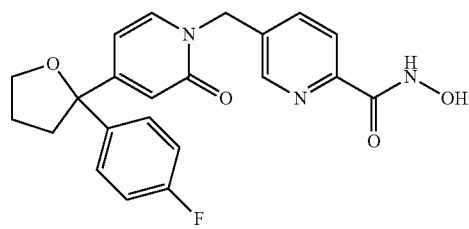

9-3

Step 1: Sodium hydride (21.60 mg, 539.98 μmol, purity 60%) was added into the compound 9-1 (70.00 mg, 269.99 μmol) in dimethylformamide (5.00 mL) solution, then stirred at 0° C. for 30 mins, then 2-methylformate-5-bromomethylpyridine (124.23 mg, 539.98 μmol) was added and was continued stirring at 0° C. for 30 mins, the temperature was raised to rt and stirred for 30 mins. The mixture was quenched by saturated ammonium chloride (1 mL*1), water (15 mL) was added then extracted with EtOAc (10 mL*3). The combined organic phases were washed by water (10 mL*2) and saturated brine (10 mL), then was dried, filtered and concentrated, followed by purification with preparative TLC (PE/EA=1/1) to give the compound 9-2. MS ESI calculated value $C_{23}H_{21}FN_2O_4$ $[M+H]^+$ 409, measured value 409.

Step 2: Hydroxylamine (1.00 mL, 50% solution) and sodium hydroxide NaOH (3.06 mg, 76.39 μmol) were added into the compound 9-2 (50.00 mg, crude product) in methanol (5.00 mL) solution, then stirred at 0° C. for 30 mins. The mixture was added hydrochloric acid to adjust pH to 7, then purified to give the compound 9-3. $^1$H NMR (400 MHz, DMSO-$d_6$) δ 8.53 (s, 1H), 7.97-7.87 (m, 1H), 7.86-7.72 (m, 2H), 7.50 (m, 2H), 7.14 (m, 2H), 6.51 (m, 1H), 6.28 (m, 1H), 5.10 (s, 2H), 4.01-3.81 (m, 2H), 2.48-2.42 (m, 2H), 1.92-1.76 (m, 2H). MS ESI calculated value $C_{22}H_{20}FN_3O_4$ $[M+H]^+$ 410, measured value 410.

Embodiment 10

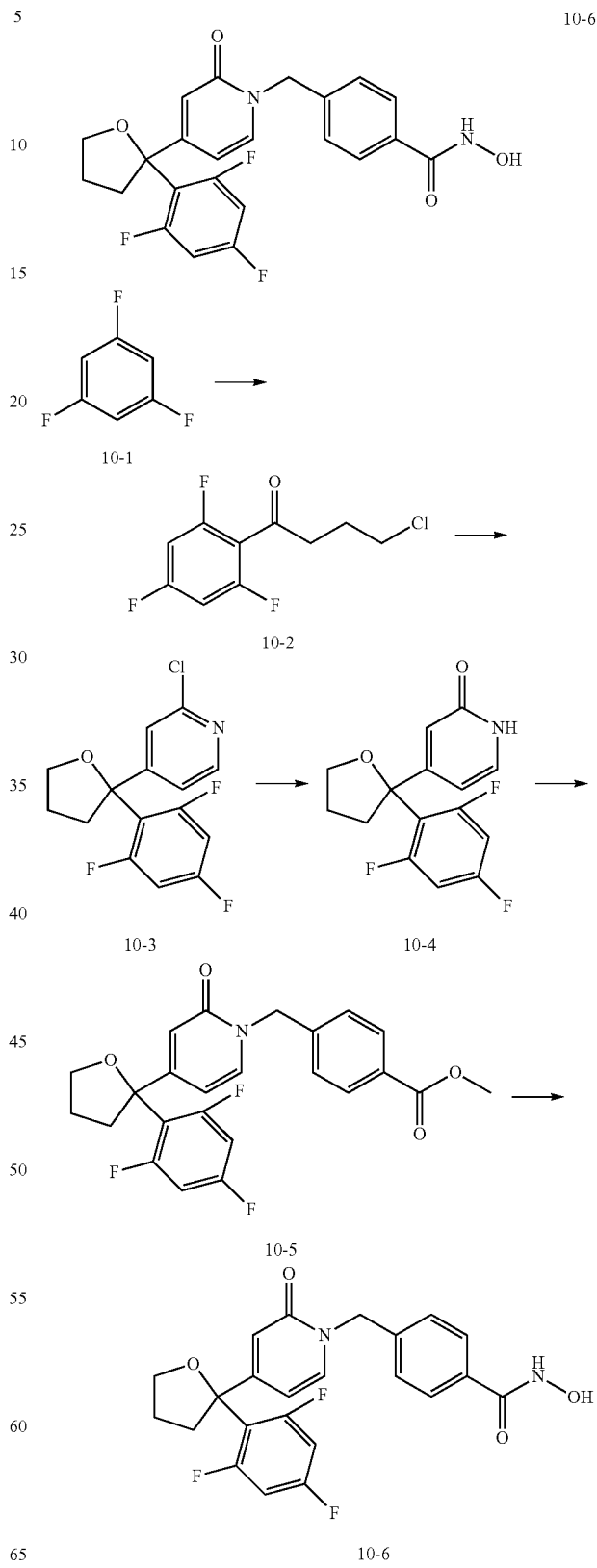

Step 1: 4-chlorobutyryl chloride (2.50 g, 17.73 mmol, 1.98 mL, 1.00 eq) was added dropwise into the mixture of the compound 10-1 (4.68 g, 35.46 mmol, 3.66 mL, 2.00 eq) and alcohol (3.14 g, 23.58 mmol, 1.29 mL, 1.33 eq), then stirred at 30° C. for 6 hours, the reaction mixture was added into ice water, then was stirred and extracted by EtOAc, washed by saturated brine, dried over anhydrous sodium sulfate, and was filtered and concentrated, then purified by silica gel column to give the compound 10-2. This liquid was used directly in the next reaction.

Step 2: At −68° C., N-butyllithium in cyclohexane solution (2.5 M, 1.12 mL, 1.10 eq) was added into 4-bromo-2-chloro-pyridine (488.80 mg, 2.54 mmol, 1.00 eq) in toluene (3.00 mL) solution, then the compound 10-2 (600.00 mg, 2.54 mmol, 1.00 eq) in toluene (1.00 mL) solution was added into the reaction system, temperature was raised to 25° C. and stirred for 6 hours. Saturated ammonium chloride solution and water were added into the reaction mixture, then the mixture was extracted by EtOAc, and washed by saturated brine, dried over anhydrous sodium sulfate, and was concentrated. After concentration, the mixture was purified with silica gel column to give the compound 10-3. MS ESI calculated value $C_{15}H_{11}F_3ONCl$ [M+H]$^+$ 314, measured value 314.

Step 3: Potassium hydroxide (146.67 mg, 2.61 mmol, 2.00 eq), tris(dibenzylideneacetone) dipalladium (119.96 mg, 131.00 μmol, 0.10 eq) and 2-di-tert-butylphosphine-2',4',6'-triisopropylbiphenyl (55.50 mg, 130.70 μmol, 0.10 eq) were added into the compound 10-3 (410.00 mg, 1.31 mmol, 1.00 eq) in dioxane (5.00 mL) and water (1.00 mL) solution, then stirred at 80° C. for 4 hours. Saturated ammonium chloride solution and water were added into the reaction mixture, then the mixture was extracted by EtOAc, and washed by saturated brine, dried over anhydrous sodium sulfate, then filtered and concentrated. After concentration, the mixture was purified by silica gel column to give the compound 10-4.

Step 4: The temperature of the compound 10-4 (100.00 mg, 338.68 μmol, 1.00 eq), methyl 4-bromomethylbenzoate (155.16 mg, 677.36 μmol, 2.00 eq) and barium carbonate (220.70 mg, 677.37 μmol, 2.00 eq) in acetonitrile (2.00 mL) solution was raised to 80° C., the mixture was stirred for 2 hours. The reaction mixture was then added water, extracted by EtOAc, washed by saturated brine and dried over anhydrous sodium sulfate, followed by concentration. After concentration, the mixture was purified by preparative thin layer chromatography to give the compound 10-5.

Step 5: Sodium hydroxide (3.61 mg, 90.21 μmol, 1.00 eq) and hydroxylamine solution (1.00 mL, 50% purity) were added into the compound 10-5 (40.00 mg, 90.21 mol, 1.00 eq) 的 methanol (2.00 mL) solution, then stirred at 25° C. for 17 hours. After the reaction mixture was concentrated, it was purified by reverse phase preparative column to give the compound 10-6. $^1$H NMR (400 MHz, MEOD) δ ppm 1.75-2.11 (m, 2H) 2.53-2.84 (m, 2H) 3.90-4.20 (m, 2H) 5.41 (s, 2H) 6.79-6.88 (m, 2H) 6.92 (s, 1H) 6.97 (dd, J=5.40, 1.25 Hz, 1H) 7.54 (d, J=8.28 Hz, 2H) 7.76 (d, J=8.28 Hz, 2H) 8.05 (d, J=5.40 Hz, 1H), MS ESI calculated value C23H19N2O4F3 [M+H]$^+$ 445, measured value 445.

Embodiment 11

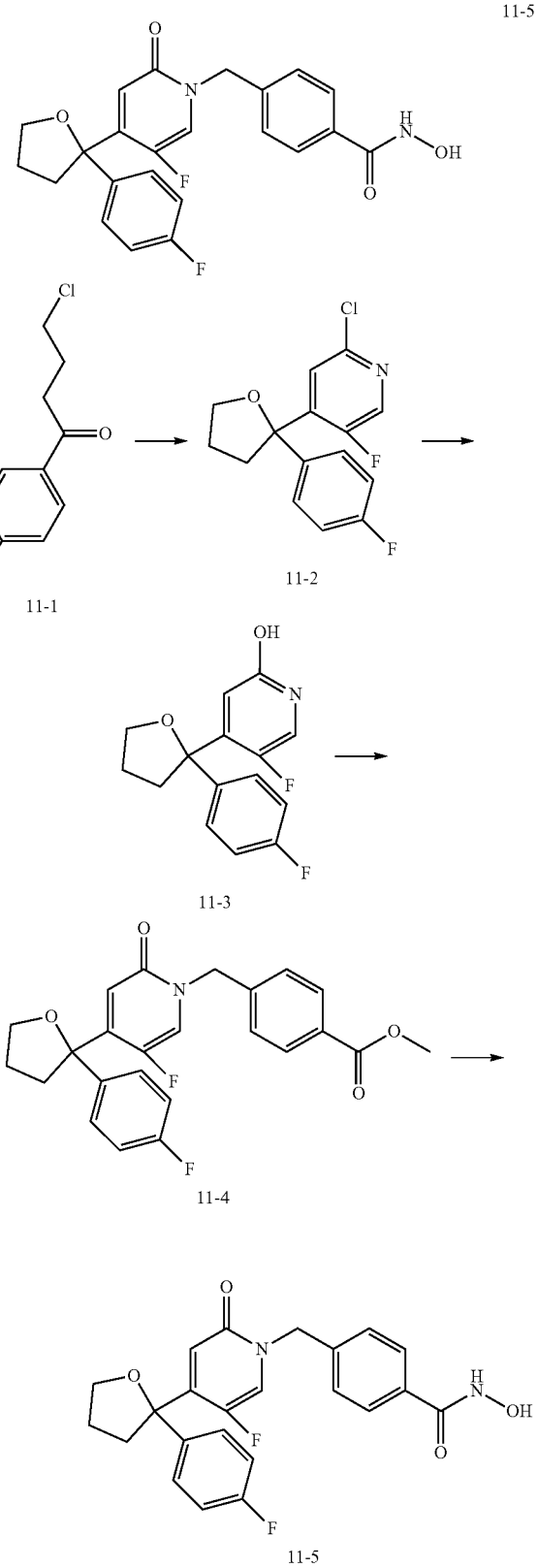

Step 1: Under nitrogen protection, at −70° C., n-BuLi (2.5 M, 9.12 mL, 1.20 eq) was added dropwise into 4-bromo-2-chloro-3-fluoropyridine (4.00 g, 19.01 mmol, 1.00 eq) in toluene (20.00 mL) solution, after the completion of the adding, the mixture was stirred at the temperature for 30 mins, then the compound 11-1 (3.81 g, 19.01 mmol, 819.67 μL, 1.00 eq) was added into the suspension above. The temperature of the reaction system was raised slowly to 40° C. and stirred for 12 hours. The reaction mixture was poured into water (80 mL), then extracted by EtOAc (40 mL×3), the combined extract was washed by brine (50 mL), and dried over anhydrous $Na_2SO_4$, filtered and concentrated under reduced pressure. The solid obtained was purified by silica gel column chromatography (PE/EtOAc=10/1) to give the compound 11-2. MS ESI calculated value $C_{15}H_{12}ClF_2NO$ [M+H]$^+$ 296, measured value 296.

Step 2: Under nitrogen protection, the mixture of compound 11-2 (3.86 g, 13.05 mmol, 1.00 eq), t-BuXPhOS (554.16 mg, 1.31 mmol, 0.10 eq), $Pd_2(dba)_3$ (1.20 g, 1.31 mmol, 0.10 eq) and KOH (1.46 g, 26.10 mmol, 2.00 eq) in dioxane (100 mL) and $H_2O$ (20 mL) was heated to 100° C. and stirred for 2 hours. The reaction mixture was then poured into $H_2O$ (80 mL), then extracted by EtOAc/MeOH (10/1, 30 mL×3), the combined extract was washed by brine (40 mL), then dried over anhydrous $Na_2SO_4$, and filtrated and concentrated under reduced pressure. The solid obtained was slurried by PE (20 mL) and filtered, dried over to give the compound 11-3. MS ESI calculated value $C_{15}H_{13}F2NO_2$ [M+H]$^+$ 278, measured value 278.

Step 3: Under nitrogen protection, at 0° C., NaH (553.97 mg, 13.85 mmol, purity 60%, 1.20 eq) was added into the compound 11-3 (3.20 g, 11.54 mmol, 1.00 eq) in DMF (60 mL) solution, then stirred at the temperature for 20 mins, then methyl 4-bromomethylbenzoate (2.64 g, 11.54 mmol, 1.10 eq) was added into the suspension above and the temperature was raised to 20° C., continued to stir for 1 hours. The reaction mixture was poured into $H_2O$ (250 mL), and extracted by EtOAc/MeOH (10/1, 50 mL×3), the combined extract was washed by brine (100 mL), then dried over anhydrous $Na_2SO_4$, filtered and concentrated under reduced pressure. The solid obtained was pass through silica gel column chromatography (PE/EtOAc=3/1) to give the compound 11-4. MS ESI calculated value $C_{24}H_{21}F_2NO_4$ [M+H]$^+$ 426, measured value 426.

Step 4: At 0° C., $NH_2OH \cdot H_2O$ (20.0 mL, 50% solution) and NaOH (2 M, 20.0 mL) solution were added dropwise in sequence into the compound 11-4 (2.00 g, 4.70 mmol, 1.00 eq) in MeOH (20.0 mL) and DCM (10.0 mL) solution, then continued to stir the reaction at 0° C. for 1 hours. Most of the solvent was eliminated by concentration under reduced pressure, the rest of the solution was cooled down to 0° C. and adjusted the pH=7-8 with concentrated hydrochloric acid, after treatment the compound 11-5 was obtained. 1H NMR (400 MHz, D MSO-d$_6$) δ 11.18 (s, 1H), 9.90-9.90 (m, 1H), 9.04 (brs, 1H), 7.98 (d, J=6.78 Hz, 1H), 7.70 (d, J=8.03 Hz, 2H), 7.44 (dd, J=8.41, 5.65 Hz, 2H), 7.37 (d, J=8.03 Hz, 2H), 7.15 (t, J=8.91 Hz, 2H), 6.60 (d, J=7.53 Hz, 1H), 4.90-5.15 (m, 2H), 3.80-4.05 (m, 2H), 2.60-2.75 (m, 1H), 2.38-2.44 (m, 1H), 1.93 (q, J=7.09 Hz, 2H). MS ESI calculated value $C_{23}H_{20}F_2N_2O_4$ [M+H]+ 427, measured value 427.

Embodiment 12

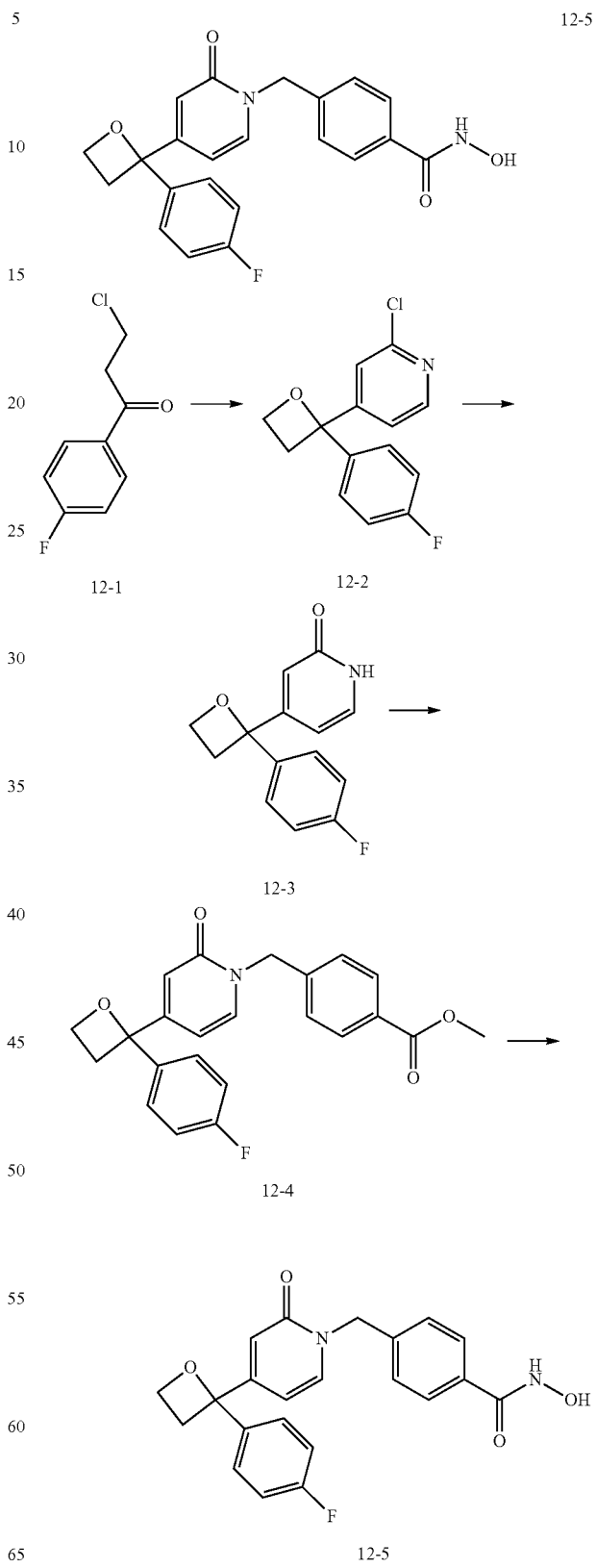

Step 1: Under N₂ protection, at −70° C., n-BuLi (2.5 M, 1.29 mL, 1.20 eq) was added dropwise into 4-bromo-2-chloropyridine (515.62 mg, 2.68 mmol, 1.00 eq) in toluene (3.00 mL) solution, after completion of adding, the mixture was stirred at the temperature for 20 mins, then the compound 12-1 (500.00 mg, 2.68 mmol, 1.00 eq) was added into the suspension above. The temperature of the reaction system was raised slowly to 25° C. and stirred for 6 hours. Toluene was eliminated by concentration under reduced pressure, the remaining solid was dissolved in DMF (3.00 mL), at 25° C., NaH (160.76 mg, 4.02 mmol, purity 60%, 1.50 eq) was added, then the system was heated to 60° C. and stirred for 2 hours. Then the reaction mixture was poured into H₂O (80 mL), then EtOAc (30 mL×3) was used for extraction, the combined extracts was washed by brine (50 mL), then dried over anhydrous Na₂SO₄, followed by filtration and concentration under reduced pressure. The solid obtained was passed through silica gel column chromatography (PE/EtOAc=10/1) to give the compound 12-2. MS ESI calculated value $C_{14}H_{11}ClFNO$ [M+H]⁺ 264, measured value 264.

Step 2: Under N₂ protection, the mixture of compound 12-2 (320.00 mg, 1.21 mmol, 1.00 eq), t-BuXPhOS (102.76 mg, 242.00 μmol, 0.20 eq), Pd₂(dba)₃ (221.60 mg, 242.00 μmol, 0.20 eq) and KOH (135.79 mg, 2.42 mmol, 2.00 eq) in dioxane (10.00 mL) and H₂O (3.00 mL) was heated to 100° C. and stirred for 2 hours. The reaction mixture was poured into H₂O (100 mL), Then EtOAc (50 mL×3) was used for extraction, the combine extracts was washed by brine (60 mL), and dried over anhydrous Na₂SO₄, followed by filtration and concentration under reduced pressure. The solid obtained was passed through preparative TLC (PE/EtOAc=3/1) to give the compound 12-3. MS ESI calculated value $C_{14}H_{12}FNO_2$ [M+H]⁺ 246, measured value 246.

Step 3: Under N₂ protection, at 0° C., NaH (56.80 mg, 1.42 mmol, purity 60%, 1.20 eq) was added into the compound 12-3 (290.00 mg, 1.18 mmol, 1.00 eq) in DMF (5.00 mL) solution, and stirred at the temperature for 20 mins, then methyl 4-bromomethylbenzoate (297.33 mg, 1.30 mmol, 1.10 eq) was added into the suspension above, the temperature of the reaction system was raised to 20° C. and continued to stir for 2 hours. The reaction mixture was poured into water (80 mL), then extracted by EtOAc/MeOH (10/1, 30 mL×3), the combined extracts was washed by brine (50 mL), then dried over anhydrous Na₂SO₄, followed by filtration and concentration under reduced pressure. The solid obtained was purified by preparative TLC (PE/EtOAc=1/1) to give the compound 12-4. MS ESI calculated value $C_{23}H_{20}FNO_4$ [M+H]⁺ 394, measured value 394.

Step 4: At 0° C., NH₂OH.H₂O (150.00 μL, 50% solution) and NaOH (2 M, 150.00 μL) solution was added dropwise in sequence into the compound 12-4 (150.00 mg, 381.28 μmol, 1.00 eq) in DCM (2.00 mL) and MeOH (2.00 mL) solution, then the reaction was stirred at 0° C. for 2 hours. Most of the solvent was eliminated by concentration under reduced pressure, the rest of the solution was purified by preparative HPLC (0.1% NH₄OH) to give the compound 12-5. ¹H NMR (400 MHz, D MSO-d₆) δ 10.99 (brs, 1H), 8.67-9.79 (brs, 1H), 7.77 (d, J=7.28 Hz, 1H), 7.69 (d, J=8.03 Hz, 2H), 7.46 (dd, J=8.66, 5.40 Hz, 2H), 7.34 (d, J=8.03 Hz, 2H), 7.20 (t, J=8.91 Hz, 2H), 6.52 (d, J=1.51 Hz, 1H), 6.18 (dd, J=7.03, 1.76 Hz, 1H), 5.08 (s, 2H), 4.39-4.58 (m, 2H), 3.01-3.19 (m, 2H). MS ESI calculated value $C_{22}H_{19}FN_2O_4$ [M+H]+ 395, measured value 395.

Embodiment 13

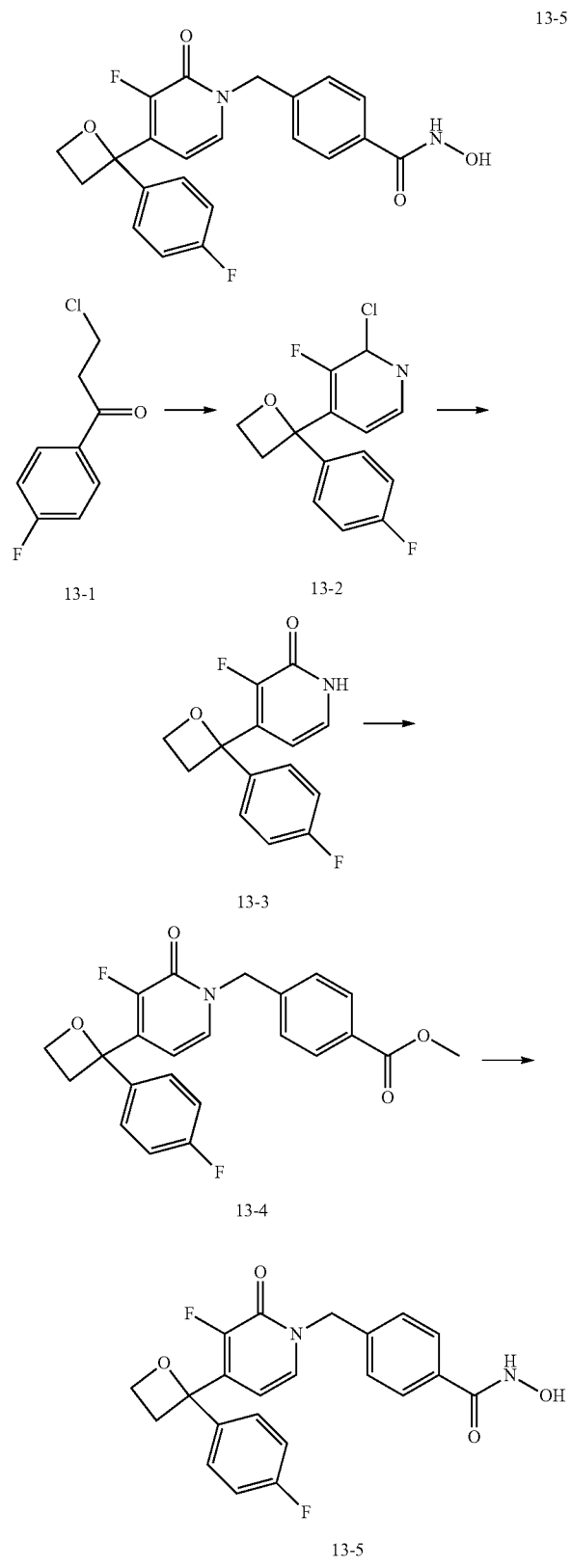

Step 1: Under N₂ protection, at −70° C., n-BuLi (2.5 M, 1.03 mL, 1.20 eq) was added dropwise into 4-bromo-2-chloro-3-fluoropyridine (450.32 mg, 2.14 mmol, 1.00 eq) in toluene (8.00 mL) solution, after completion of adding, the mixture was stirred at the temperature for 20 mins, then compound 13-1 (400.00 mg, 2.14 mmol, 1.00 eq) was added into the suspension above. The temperature of the system was raised slowly to 25° C. and stirred for 6 hours. Toluene was eliminated by concentration under reduced temperature, the remaining solid was dissolved in DMF (8.00 mL), at 25° C., NaH (128.40 mg, 3.21 mmol, purity 60%, 1.50 eq) was added and then the system was heated to 60° C. and stirred for 2 hours. The reaction mixture was poured into water (80 mL), then extracted by EtOAc (30 mL×3), the combined extracts was washed by brine (50 mL), then dried over anhydrous Na₂SO₄, followed by filtration and concentration under reduced pressure. The solid obtained was passed through column chromatography (PE/EtOAc=10/1) to give the compound 13-2. MS ESI calculated value $C_{14}H_{10}ClF_2NO$ [M+H]⁺ 282, measured value 282.

Step 2: Under N₂ protection, the mixture of compound 13-2 (440.00 mg, 1.56 mmol, 1.00 eq), t-BuXPhOS (132.49 mg, 312.00 μmol, 0.20 eq), Pd₂(dba)₃ (285.70 mg, 312.00 μmol, 0.20 eq) and KOH (175.06 mg, 3.12 mmol, 2.00 eq) in dioxane (10.00 mL) and H₂O (3.00 mL) was heated to 100° C. and stirred for 2 hours. The reaction mixture was poured into water (100 mL), and extracted by EtOAc (50 mL×3), the combined extracts was washed by brine (60 mL), then dried over anhydrous Na₂SO₄, followed by filtration and concentration under reduced pressure. The solid obtained was purified by preparative TLC (PE/EtOAc=3/1) to give the compound 13-3. MS ESI calculated value $C_{14}H_{11}F_2NO_2$ [M+H]⁺ 264, measured value 264.

Step 3: Under N₂ protection, at 0° C., NaH (69.29 mg, 1.73 mmol, purity 60%, 1.20 eq) was added into the compound 13-3 (380.00 mg, 1.44 mmol, 1.00 eq) in DMF (5.00 mL) solution, then the mixture was stirred at the temperature for 20 mins, then methyl 4-bromomethylbenzoate (363.74 mg, 1.59 mmol, 1.10 eq) was added into the suspension above and the temperature of the system was raised to 20° C., then continued stirring for 2 hours. The reaction mixture was poured into water (80 mL), and extracted by EtOAc/MeOH (10/1, 30 mL×3), the combined extracts was washed by brine (50 mL), then dried over anhydrous Na₂SO₄, followed by filtration and concentration under reduced pressure. The solid obtained was purified by preparative TLC (PE/EtOAc=1/1) to give the compound 13-4. MS ESI calculated value $C_{23}H_{19}F_2NO_4$ [M+H]⁺ 412, measured value 412.

Step 4: At 0° C., NH₂OH.H₂O (3.00 mL, 50% solution) and NaOH (2 M, 3.00 mL) solution was added dropwise in sequence into the compound 13-4 (350.00 mg, 850.75 μmol, 1.00 eq) in DCM (3.00 mL) and MeOH (3.00 mL) solution, then the reaction was stirred at 0° C. for 1 hours. Most of the solvent was eliminated by concentration under reduced pressure, the rest of the solution was purified by preparative HPLC (0.1% TFA) to give the compound 13-5. ¹H NMR (400 MHz, DMSO-d₆) δ 11.19 (brs, 1H), 8.06 (d, J=6.52 Hz, 1H), 7.71 (d, J=8.28 Hz, 2H), 7.38-7.50 (m, 5H), 7.22 (t, J=8.91 Hz, 2H), 6.65 (d, J=7.28 Hz, 1H), 4.98-5.08 (m, 2H), 4.49-4.59 (m, 2H), 3.25-3.34 (m, 1H), 3.05-3.15 (m, 1H). MS ESI calculated value $C_{22}H_{18}F_2N_2O_4$ [M+H]+ 413, measured value 413.

Embodiment 14

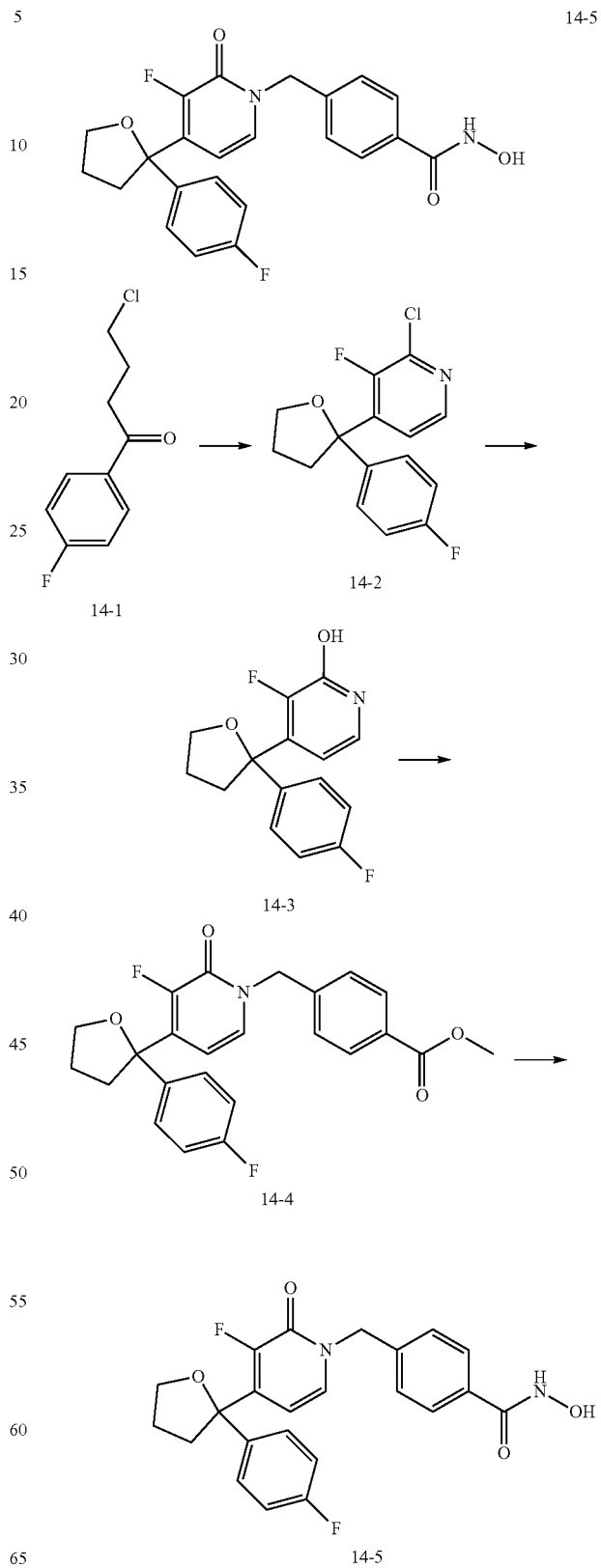

Step 1: Under N₂ protection, at −70° C., n-BuLi (2.5 M, 6.84 mL, 1.20 eq) was added dropwise into 4-bromo-2-chloro-5-fluoropyridine (3.00 g, 14.26 mmol, 1.00 eq) in toluene (80.00 mL) solution, after completion of adding, the mixture was stirred at the temperature for 30 mins, then the compound 14-1 (2.86 g, 14.26 mmol, 2.34 mL, 1.00 eq) was added into the suspension above. the temperature of the system was raised slowly to 40° C. and stirred for 12 hours. The reaction mixture was poured into water (300 mL), and extracted by EtOAc (100 mL×3), the combined extracts was washed by brine (100 mL), then dried over anhydrous Na₂SO₄, followed by filtration and concentration under reduced pressure. The solid obtained was passed through column chromatography (PE/EtOAc=10/1) to give the compound 14-2. MS ESI calculated value $C_{15}H_{12}ClF_2NO$ [M+H]⁺ 296, measured value 296.

Step 2: Under N₂ protection, the mixture of compound 14-2 (300.00 mg, 1.01 mmol, 1.00 eq), t-BuXPhOS (85.78 mg, 202.00 μmol, 0.20 eq), Pd₂(dba)₃ (184.98 mg, 202.00 μmol, 0.20 eq) and KOH (113.34 mg, 2.02 mmol, 2.00 eq) in dioxane (10.00 mL) and H₂O (3.00 mL) was heated to 100° C. and stirred for 2 hours. The reaction mixture was poured into water (100 mL), and extracted by EtOAc (50 mL×3), the combined extracts was washed by brine (60 mL), then dried over anhydrous Na₂SO₄, followed by filtration and concentration under reduced pressure. The solid obtained was purified by preparative TLC (PE/EtOAc=3/1) to give the compound 14-3. MS ESI calculated value $C_{15}H_{13}F_2NO_2$ [M+H]⁺ 278, measured value 278.

Step 3: Under N₂ protection, at 0° C., NaH (34.62 mg, 865.58 μmol, purity 60%, 1.20 eq) was added into the compound 14-3 (200.00 mg, 721.32 μmol, 1.00 eq) in DMF (5.00 mL) solution, and the mixture was stirred at the temperature for 20 mins, then methyl 4-bromomethylbenzoate (165.23 mg, 721.32 μmol, 1.00 eq) was added into the suspension above and the temperature of the system was raised to 20° C., then continued stirring for 1 hours. The reaction mixture was poured into water (50 mL), and extracted by EtOAc/MeOH (10/1, 20 mL×3), the combined extracts was washed by brine (30 mL), then dried over anhydrous Na₂SO₄, followed by filtration and concentration under reduced pressure. The solid obtained was purified by preparative TLC (PE/EtOAc=1/1) to give the compound 14-4. MS ESI calculated value $C_{24}H_{21}F_2NO_4$ [M+H]⁺ 426, measured value 426.

Step 4: At 0° C., NH₂OH.H₂O (2.00 mL, 50% solution) and NaOH (2.00 mL, 2 M) solution were added dropwise in sequence into the compound 14-4 (100.00 mg, 235.06 μmol, 1.00 eq) in DCM (2.00 mL) and MeOH (4.00 mL) solution, then the reaction was stirred at 0° C. for 1 hours. Most of the solvent was eliminated by concentration under reduced pressure, the rest of the solution was cooled down to 0° C., concentrated hydrochloric acid was added to adjust the pH=6-7, aftertreatment to give the compound 14-5. ¹H NMR (400 MHz, D MSO-d₆) δ 11.17 (brs, 1H), 9.05 (brs, 1H), 8.61-9.43 (m, 1H), 7.64-7.73 (m, 3H), 7.46 (dd, J=8.5, 5.5 Hz, 2H), 7.34 (d, J=8.0 Hz, 2H), 7.16 (t, J=8.9 Hz, 2H), 6.48 (t, J=6.9 Hz, 1H), 5.07-5.18 (m, 2H), 3.90 (t, J=7.2 Hz, 2H), 2.64-2.70 (m, 1H), 2.41-2.47 (m, 1H), 1.82-1.97 (m, 2H). MS ESI calculated value $C_{23}H_{20}F_2N_2O_4$ [M+H]+ 427, measured value 427.

Embodiment 15

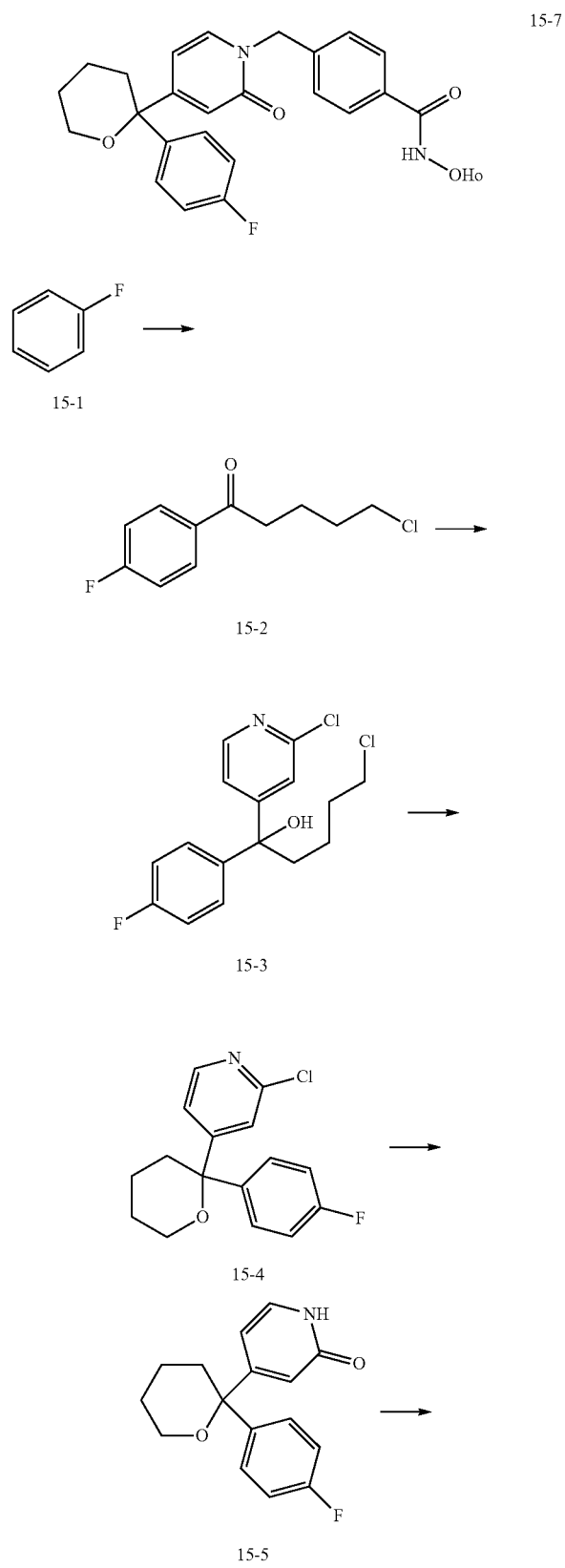

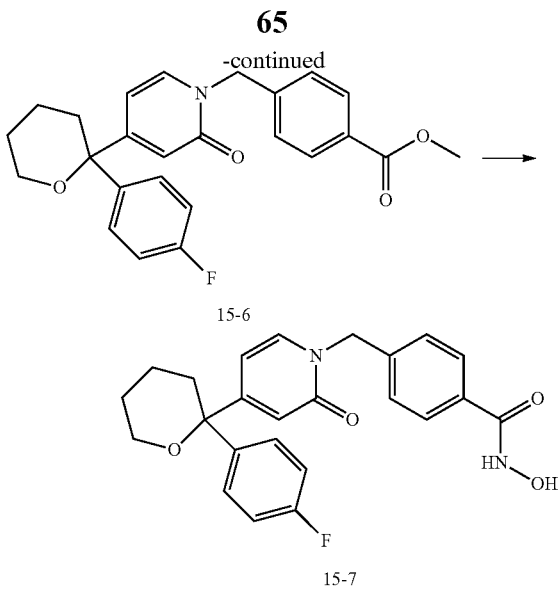

15-6

15-7

Step 1: At 0° C., compound 15-1 (6.20 g, 64.50 mmol, 6.08 mL, 2.00 eq) and alcohol (4.73 g, 35.48 mmol, 1.10 eq) was added into a 100 mL 3-neck flask, then added also 5-chlorovaleryl chloride (5.00 g, 32.25 mmol, 4.17 mL, 1.00 eq), the mixture was heated to rt and stirred for 2 hours. The mixture was quenched by ice water (20 mL), water (100 mL) was added and extracted by EtOAc (100 mL*2), the organic phases were combined, then washed by saturated brine, dried over sodium sulfate, followed by filtration and concentration, to give the compound 15-2. $^1$H NMR (400 MHz, CDCl$_3$) δ 8.08-7.91 (m, 2H), 7.13 (m, 2H), 3.63-3.55 (m, 2H), 2.99 (m, 2H), 1.98-1.82 (m, 4H).

Step 2: At −78° C. nitrogen atmosphere, tert-butyllithium (2.5 M, 13.32 mL, 1.10 eq) was slowly added dropwise into 4-bromo-2-chloropyridine (5.83 g, 30.28 mmol, 1.00 eq) in toluene (100.00 mL) solution, then stirred for 10 mins and added the compound 15-2 (6.50 g, 30.28 mmol, 1.00 eq), then continued stirring for 30 mins. Saturated ammonium chloride (20 mL) was used to quench the reaction, water (100 mL) was then added, and EtOAc (100 mL*3) was used for extraction, the combined organic phases were washed by saturated brine (100 mL), dried over sodium sulfate, filtered and concentrated, separated with column (silica gel column, PE/EtOAc=10/1) to give the compound 15-3. MS ESI calculated value $C_{16}H_{16}Cl_2FNO$ [M+H]$^+$ 328.2, measured value 328.2.

Step 3: At 0° C. nitrogen atmosphere, NaH (877.49 mg, 21.94 mmol, 60% purity, 1.20 eq) was added into the compound 15-3 (6.00 g, 18.28 mmol, 1.00 eq) in N, N-dimethylformamide (30.00 mL) solution, then stirred at 0-5° C. for 30 mins. The reaction was quenched by saturated ammonium chloride (30 mL), then water (100 mL) was added, and extracted by EtOAc (80 mL*3), the combined organic phases were washed by water (100 mL*3) and saturated brine (50 mL*1), dried over sodium sulfate, filtered and concentrated to give the compound 15-4. MS ESI calculated value $C_{16}H_{15}ClFNO$ [M+H]$^+$ 291.75, measured value 292.0.

Step 4: Under nitrogen protection, the compound 15-4 (1.00 g, 3.43 mmol, 1.00 eq), potassium hydroxide (384.64 mg, 6.86 mmol, 2.00 eq), tris(dibenzylideneacetone) dipalladium (627.74 mg, 686.00 μmol, 0.20 eq) and 2-di-tertbutylphosphine-2',4',6'-triisopropylbiphenyl (291.10 mg, 686.00 μmol, 0.20 eq) were added into the mixed solution of water (5.00 mL) and 1,4-dioxane (10.00 mL), the mixture was then heated to 90° C., then stirred for 3 hours. The mixture was concentrated and water (50 mL) was added, then was extracted by EtOAc (20 mL*3), the combined organic phases were washed by saturated brine (50 mL), dried over sodium sulfate, filtered and concentrated, then purified by column (silica gel column, PE/EtOAc=10/1 to 2/1, dichloromethane/methanol=20/1) to give the compound 15-5. MS ESI calculated value $C_{16}H_{16}FNO_2$ [M+H]$^+$ 273.30, measured value 274.1.

Step 5: At 0° C. under nitrogen protection, sodium hydride (17.56 mg, 439.08 mol, 60% purity, 1.00 eq) was added into the compound 15-5 (150.00 mg, 439.08 μmol, 1.00 eq) in N, N-dimethylformamide (5.00 mL) solution, the mixture was stirred for 10 mins then methyl 4-bromomethylbenzoate (125.72 mg, 548.85 μmol, 1.00 eq) was added, then the mixture was heated to rt, and continued stirring for 30 mins. Saturated ammonium chloride (2 mL) and water (15 mL) was added into the system, then extracted by EtOAc (10 mL*3), the combined organic phases were washed by saturated brine (15 mL), dried over sodium sulfate, then filtered, concentrated and purified to give the compound 15-6. MS ESI calculated value $C_{25}H_{24}FNO_4$ [M+H]$^+$ 421.46, measured value 422.2.

Step 6: Hydroxylamine solution (2.00 mL, 50% solution) and sodium hydroxide (35.09 mg, 877.32 μmol, 3.00 eq) were added into the compound 15-6 (145.00 mg, 292.44 μmol, 1.00 eq) in methanol (10.00 mL) solution, the mixture was stirred at rt for 1 hours, then concentrated and purified by preparative HPLC (0.225% FA) to give the compound 15-7. $^1$H NMR (400 MHz, D MSO-d$_6$) δ=7.73-7.62 (m, 3H), 7.46 (m, 2H), 7.32 (d, J=8.2 Hz, 2H), 7.16 (t, J=8.8 Hz, 2H), 6.47 (d, J=1.6 Hz, 1H), 6.20 (dd, J=1.6, 7.2 Hz, 1H), 5.04 (s, 2H), 3.71~3.53 (m, 2H), 2.34~2.07 (m, 2H), 1.65-1.46 (m, 4H). MS ESI calculated value $C_{24}H_{23}FN_2O_4$ [M+H]$^+$ 422.45, measured value 423.4.

Embodiment 16

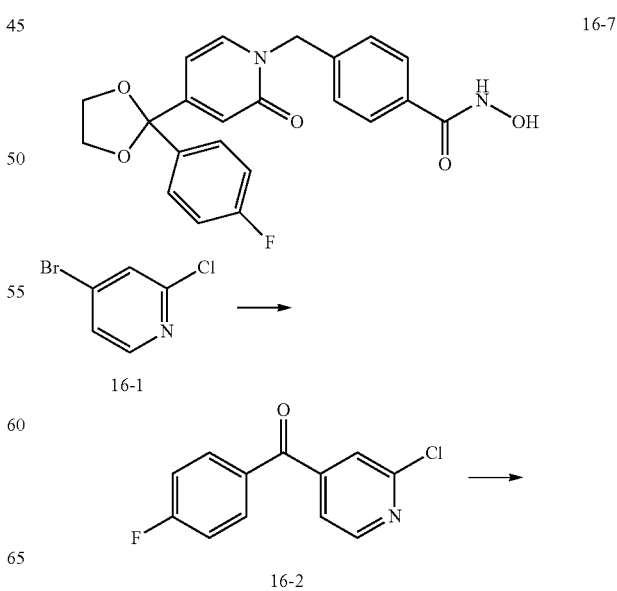

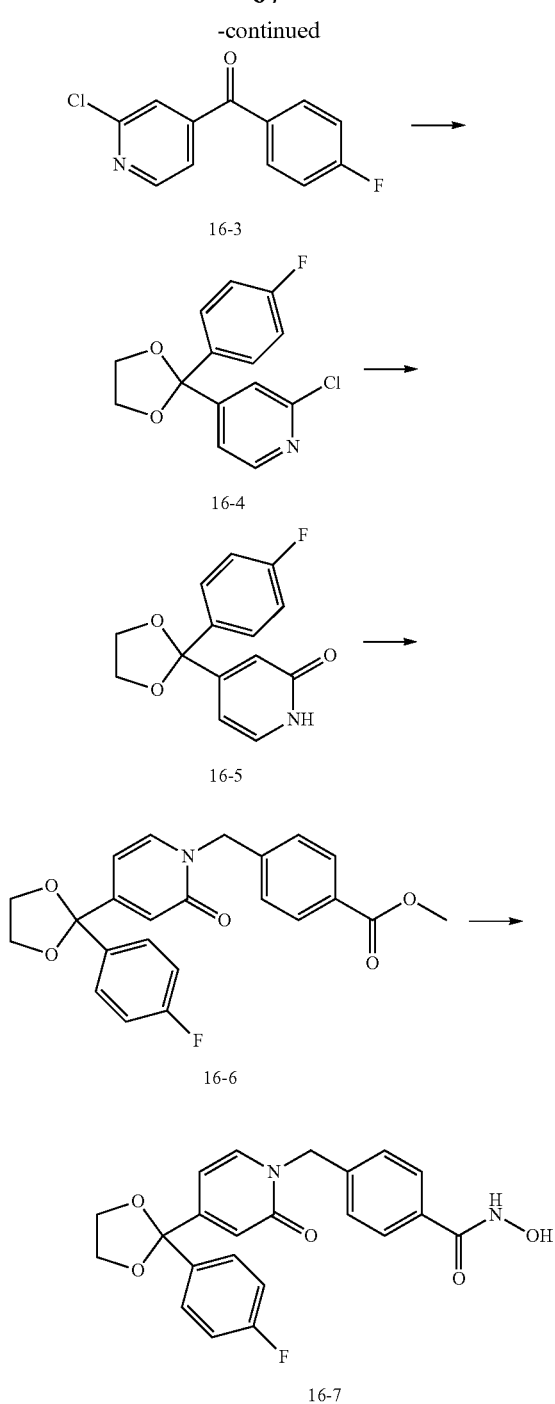

16-3

16-4

16-5

16-6

16-7

Step 1: At −78° C. under nitrogen protection, N-butyl-lithium (2.5 M, 88.63 mL, 1.10 eq) was slowly added dropwise into the compound 16-1 (38.76 g, 201.43 mmol, 1.00 eq) in toluene (250.00 mL) solution, then stirred for 30 mins, then p-fluorobenzaldehyde was slowly added dropwise into the reaction system (25.00 g, 201.43 mmol, 21.19 mL, 1.00 eq), the system temperature was raised to rt in 30 mins, saturated ammonium chloride (100 mL) solution was added into the system, followed by water (200 mL), then extracted by EtOAc (150 mL*3), the organic phases were combined and washed by saturated brine (150 mL), dried over sodium sulfate, filtered and concentrated, then purified by column (silica gel column, PE:EtOAc=5:1) to give the compound 16-2. $^1$H NMR (400 MHz, CDCl$_3$) δ 8.30 (d, J=5.2 Hz, 1H), 7.43-7.37 (m, 1H), 7.35-7.29 (m, 2H), 7.20 (dd, J=0.8, 5.2 Hz, 1H), 7.11-7.03 (m, 2H), 5.78 (d, J=2.6 Hz, 1H), 2.67 (d, J=3.4 Hz, 1H). MS ESI calculated value $C_{12}H9ClFNO$ [M+H]$^+$ 237.66, measured value 238.2.

Step 2: At 0° C., Dess-Martin Periodinane (45.15 g, 106.46 mmol, 32.96 mL, 1.10 eq) was added into the compound 16-2 (23.00 g, 96.78 mmol, 1.00 eq) in dichloromethane (230.00 mL), the system temperature was raised to 25° C., then stirred for 2 hours. The system was then filtered, the filtrate was concentrated, chromatographic purified by silica gel column (PE:EtOAc=5:1) to give the compound 16-3. MS ESI calculated value $C_{12}H7ClFNO$ [M+H]$^+$ 235.64, measured value 236.2.

Step 3: P-toluenesulfonic acid (7.27 g, 38.19 mmol, 3.00 eq) and ethanediol (1.58 g, 25.46 mmol, 1.42 mL, 2.00 eq) were added into the compound 16-3 (3.00 g, 12.73 mmol, 1.00 eq) in toluene (100.00 mL) solution, the system was heated to 110° C., then stirred for 5 hours. The mixture was concentrated then purified by column (PE:EtOAc=10:1 至 5:1) to give the compound 16-4. MS ESI calculated value $C_{14}H_{11}ClFNO_2$ [M+H]$^+$ 279.69, measured value 280.0.

Step 4: Tris(dibenzylideneacetone) dipalladium (61.55 mg, 67.22 μmol, 0.20 eq), potassium hydroxide (40.12 mg, 715.08 μmol, 2.00 eq) and 2-di-tertbutylphosphine-2', 4', 6'-triisopropylbiphenyl (28.54 mg, 67.22 μmol, 0.20 eq) were added into the mixture of the compound 16-4 (100.00 mg, 336.09 μmol, 1.00 eq) in 1, 4-dioxane (5.00 mL), the system was heated to 90° C. and stirred for 3 hours. The mixture was concentrated and water (10 mL) was added, then extracted by EtOAc (10 mL*3), the organic phases were combined then washed with saturated brine (10 mL), dried over sodium sulfate, filtered and concentrated, then purified to give the compound 16-5. MS ESI calculated value $C_{14}H_{12}FNO_3$ [M+H]$^+$ 261.25, measured value 262.2.

Step 5: At 0° C. under nitrogen protection, sodium hydride (22.54 mg, 563.44 μmol, 60% purity, 2.00 eq) was added into the mixture of the compound 16-5 (80.00 mg, 281.72 μmol, 1.00 eq) in N, N-dimethylformamide (10.00 mL), the system was stirred for 10 mins, then methyl 4-bromomethylbenzoate (129.07 mg, 563.44 μmol, 2.00 eq) was added, and continued stirring for 30 mins. The mixture was quenched by water (5 mL), and extracted by EtOAc (5 mL*3), the combined organic phases was then washed by water (10 mL) and saturated brine (10 mL), dried over sodium sulfate, filtered and concentrated then purified to give the compound 16-6. MS ESI calculated value $C_{23}H_{20}FNO_5$ [M+H]$^+$ 409.41, measured value 410.3.

Step 6: Hydroxylamine solution (1.00 mL, 50% purity) and sodium hydroxide (17.03 mg, 425.73 μmol, 3.00 eq) were added into the compound 16-6 (70.00 mg, 141.91 μmol, 1.00 eq) in methanol (5.00 mL) solution, the mixture was stirred at rt for 1 hours. the mixture was concentrated then purified by preparative HPLC (0.225% FA) to give the compound 16-7. $^1$H NMR (400 MHz, D MSO-d$_6$) δ=7.77 (d, J=7.2 Hz, 1H), 7.68 (d, J=8.2 Hz, 2H), 7.53-7.45 (m, 2H), 7.33 (d, J=8.2 Hz, 2H), 7.19 (t, J=8.8 Hz, 2H), 6.48 (d, J=1.8 Hz, 1H), 6.20 (dd, J=1.8, 7.2 Hz, 1H), 5.08 (s, 2H), 3.99 (m, 4H). MS ESI calculated value $C_{22}H_{19}FN_2O_5$ [M+H]$^+$ 410.40, measured value 411.1.

Embodiment 17

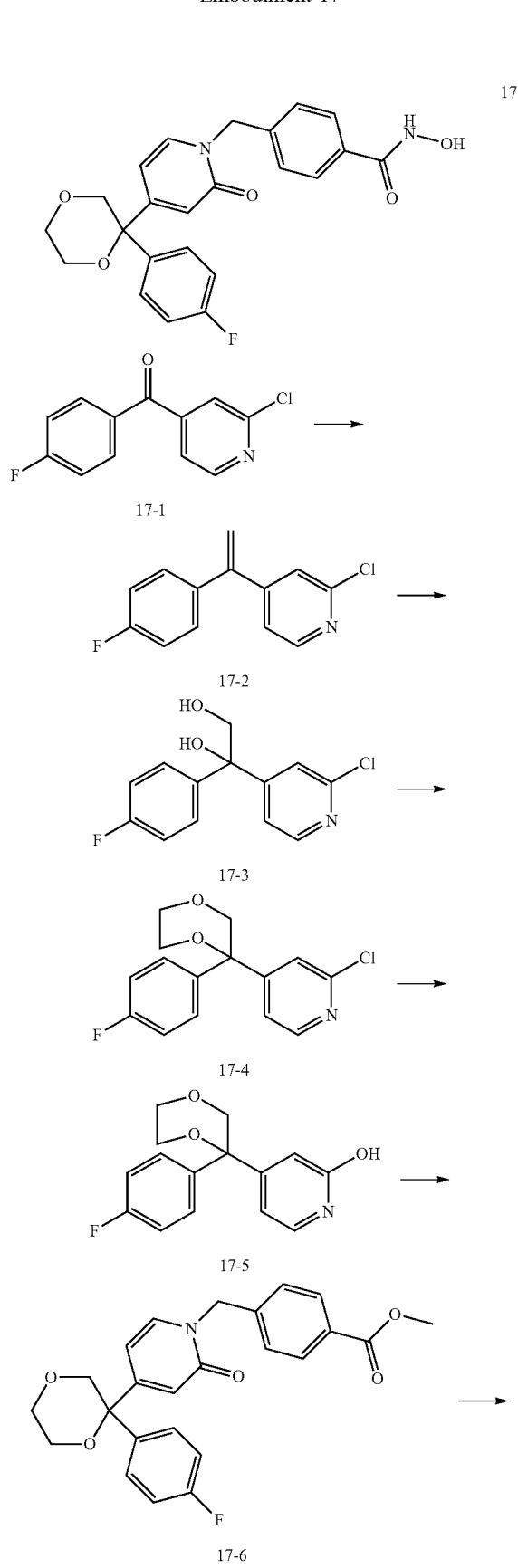

17-7

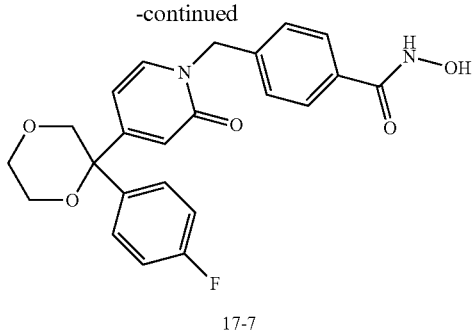

17-7

Step 1: Under N₂ protection, methyltriphenylphosphonium iodide (2.83 g, 7.01 mmol, 1.10 eq) and t-BuOK (1 M, 7.01 m, 1.10 eq) 的 THF (20.00 mL) solution were heated and refluxed for 1 hours. Then the suspension was cooled down to 0° C. and added the compound 17-1 (1.50 g, 6.37 mmol, 1.00 eq), and the reaction mixture obtained was stirred at 20° C. for 12 hours. The reaction mixture was poured into water (100 mL), and extracted by EtOAc (50 mL×3), the combined extracts was washed by brine (50 mL), then dried over anhydrous Na₂SO₄, followed by filtration and concentration under reduced pressure. The solid obtained was passed through column chromatography (PE/EtOAc=20/1) to give the compound 17-2. MS ESI calculated value $C_{13}H_{19}ClFN$ [M+H]+ 234, measured value 234.

Step 2: Compound 17-2 (800.00 mg, 3.42 mmol, 1.00 eq) and OsO₄ (869.47 mg, 3.42 mmol, 177.44 μL, 1.00 eq) in THF (10.00 mL) and H₂O (2.00 mL) solution was stirred at 20° C. for 4 hours. The reaction mixture was washed by 2M Na₂SO₃ solution (80 mL), and extracted by EtOAc (30 mL×3), the combined extracts was washed by brine (50 mL), then dried over anhydrous Na₂SO₄, filtered and concentrated under reduced temperature to give the compound 17-3. MS ESI calculated value $C_{13}H_{11}ClFNO_2$ [M+H]+ 268, measured value 268.

Step 3: Compound 17-3 (800.00 mg, 2.99 mmol, 1.00 eq), 1,2-dibromoethane (561.45 mg, 2.99 mmol, 225.48 μL, 1.00 eq) and t-BuOK (503.03 mg, 4.49 mmol, 1.50 eq) in DMSO (10.00 mL) was heated to 70° C. and stirred for 6 hours. The reaction mixture was poured into water (100 mL), and extracted by EtOAc/MeOH (10/1, 50 mL×3), the combined extracts was washed by brine (80 mL), then dried over anhydrous Na2SO4, followed by filtration and concentration under reduced pressure. The solid obtained was purified by preparative TLC (PE/EtOAc=2/1) to give the compound 17-4. MS ESI calculated value $C_{15}H_{13}ClFNO_2$ [M+H]+ 294, measured value 294.

Step 4: Under N₂ protection, compound 17-4 (180.00 mg, 612.83 μmol, 1.00 eq), t-BuXPhOS (26.02 mg, 61.28 μmol, 0.10 eq), Pd₂(dba)₃ (56.12 mg, 61.28 μmol, 0.10 eq) and KOH (68.77 mg, 1.23 mmol, 2.00 eq) in dioxane (10.00 mL) and H₂O (2.00 mL) solution was heated to 100° C. and stirred for 1 hours. The reaction mixture was poured into water (80 mL), and 2M HCl was used to adjust pH=6, then extracted by EtOAc (30 mL×3), the combined extracts was washed by brine (50 mL), then dried over anhydrous Na2SO4, followed by filtration and concentration under reduced pressure. The solid obtained was purified by preparative TLC (PE/EtOAc=3/1) to give the compound 17-5. MS ESI calculated value $C_{15}H_{14}FNO_3$ [M+H]+ 276, measured value 276.

Step 5: Under N₂ protection, at 0° C., NaH (15.69 mg, 392.34 μmol, purity 60%, 1.20 eq) was added into the compound 17-5 (90.00 mg, 326.95 μmol, 1.00 eq) in DMF (5.00 mL) solution, then continued stirring at this temperature for 20 mins. Then methyl 4-(bromomethyl) benzoate (74.89 mg, 326.95 μmol, 1.00 eq) was added into the suspension above, the reaction mixture was heated to 15° C. and stirred for 1 hours. The reaction mixture was poured into water (50 mL), and extracted by EtOAc (20 mL×3), the combined extracts was washed by brine (50 mL), then dried over anhydrous Na$_2$SO$_4$, followed by filtration and concentration under reduced pressure. The solid obtained was purified by preparative TLC (PE/EtOAc=1/2) to give the compound 17-6. MS ESI calculated value C$_{24}$H$_{22}$FNO$_5$ [M+H]+ 424, measured value 424.

Step 6: At 0° C., NH$_2$OH.H$_2$O (1.00 mL, 50% solution) and NaOH solution (2 M, 1.00 mL) were added dropwise in sequence into the compound 17-6 (100.00 mg, 236.17 μmol, 1.00 eq) in DCM (1.00 mL) and MeOH (2.00 mL) solution. When the addition was completed, the reaction mixture was stirred at 0° C. for 6 hours. Most of the solvent was eliminated by concentration under reduced pressure. The rest of the solution was cooled down to 0° C. and 2 M HCl was used to adjust pH=8, then filtered and rinsed repeatedly with H$_2$O (5 mL×3), finally dried in vacuum to give the compound 17-7. $^1$H NMR (400 MHz, D MSO-d$_6$) δ 11.17 (brs, 1H), 9.04 (brs, 1H), 7.74 (d, J=7.28 Hz, 1H), 7.69 (d, J=8.28 Hz, 2H), 7.46 (dd, J=9.03, 5.52 Hz, 2H), 7.33 (d, J=8.28 Hz, 2H), 7.19 (t, J=8.91 Hz, 2H), 6.57 (d, J=1.76 Hz, 1H), 6.13 (dd, J=7.15, 1.88 Hz, 1H), 5.07 (s, 2H), 4.11-4.24 (m, 1H), 3.99-4.08 (m, 1H), 3.54-3.71 (m, 4H). MS ESI calculated value C$_{23}$H$_{21}$FN$_2$O$_5$ [M+H]+ 425, measured value 425.

Embodiment 18

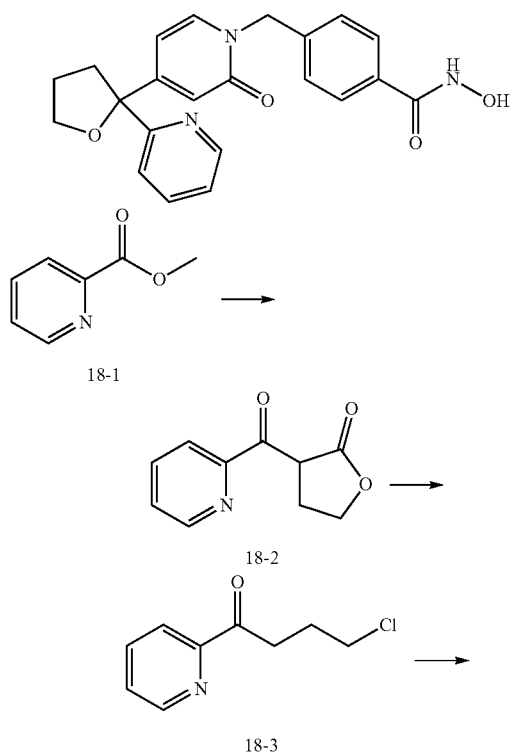

Step 1: At 0° C., sodium hydride (1.75 g, 43.75 mmol, purity 60%, 1.20 eq) was added into 1, 4-butyrolactone (3.45 g, 40.11 mmol, 3.05 mL, 1.10 eq) in toluene (30.00 mL) solution, then the compound 18-1 (5.00 g, 36.46 mmol, 4.39 mL, 1.00 eq) in toluene (10.00 mL) solution was added at 0° C., the mixture then was stirred to react at 20° C. for 12 hours. Saturated ammonium chloride solution and water were added into the reaction mixture, then extracted by EtOAc. The organic phase was washed by saturated brine, dried over anhydrous sodium sulfate, filtered and concentrated to give the compound the compound 18-2, which was used directly in the next reaction.

Step 2: The mixture of the compound 18-2 (3.22 g, 16.84 mmol, 1.00 eq) and 36% hydrochloric acid (10.20 g, 100.71 mmol, 10.00 mL, 5.98 eq) was heated to 80° C., and stirred to react for 3 hours. The reaction mixture was poured into 0° C. saturated potassium carbonate solution, water was added then, and extracted by EtOAc, the organic phase was washed by brine, dried over anhydrous sodium sulfate, filtered and concentrated, then purified by silica gel column to give the compound 18-3, which was used directly in the next reaction.

Step 3: At −68° C., N-butyllithium hexanesolution (2.5 M, 1.34 mL, 1.10 eq) was added dropwise into 2-fluoro-4-iodopyridine (730.20 mg, 3.05 mmol, 1.00 eq) toluene (5.00 mL)

solution, then the compound 18-3 (560.00 mg, 3.05 mmol, 1.00 eq) in toluene (1.00 mL) solution was added, the reaction gradually heated to 20° C., then stirred to react for 2 hours. Saturated ammonium chloride solution and water were added into the reaction mixture, then extracted by EtOAc, the organic phase was washed by saturated brine, dried over anhydrous sodium sulfate, filtered and concentrated, then purified by silica gel column to give the compound 18-4. MS ESI calculated value $C_{14}H_{13}ClN_2O$ [M+H]+ 261.0, measured value 261.0.

Step 4: Potassium hydroxide (322.82 mg, 5.75 mmol, 2.00 eq), tris(dibenzylideneacetone) dipalladium (263.42 mg, 287.66 μmol, 0.10 eq) and 2-di-tertbutylphosphine-2', 4', 6'-triisopropylbiphenyl (122.15 mg, 287.66 μmol, 0.10 eq) were added into the compound 18-4 (750.00 mg, 2.88 mmol, 1.00 eq) in dioxane (5.00 mL) and water (1.00 mL) solution, then stirred at 100° C. for 4 hours. Saturated ammonium chloride and water were added into the reaction mixture, then extracted by EtOAc, washed by brine, dried over anhydrous sodium sulfate, filtered and concentrated. After concentration, it was purified by silica gel column to give the compound 18-5. MS ESI calculated value $C_{14}H_{14}N_2O_2$ [M+H]+ 243, measured value 243.

Step 5: At 0° C., sodium hydride (32.29 mg, 807.36 μmol, 60% purity, 1.20 eq) was added into the compound 18-5 (163.00 mg, 672.80 μmol, 1.00 eq) in N, N-dimethylformamide (2.00 mL) solution, methyl 4-bromomethylbenzoate (154.12 mg, 672.80 μmol, 1.00 eq) in N, N-dimethylformamide (1.00 mL) solution was added into the system, then stirred at 20° C. for 2 hours. Saturated ammonium chloride solution and water was added into the reaction mixture, extracted by EtOAc, washed by brine, dried over anhydrous sodium sulfate, followed by concentrated to give the compound 18-6. MS ESI calculated value $C_{23}H_{22}N_2O_4$ [M+H]+ 391.0, measured value 391.0.

Step 6: Sodium hydroxide (22.54 mg, 563.48 μmol, 1.00 eq) and hydroxylamine solution (1.00 mL, 50% solution) were added into the compound 18-6 (220.00 mg, 563.48 μmol, 1.00 eq) in methanol (2.00 mL) solution, then stirred at 20° C. for 6 hours. After concentration of the reaction mixture, the mixture was purified by reverse phase preparative HPLC to give the compound 18-7. $^1$H NMR (400 MHz, METHANOL-d4) δ=8.53 (dd, J=0.8, 4.8 Hz, 1H), 7.82-7.74 (m, 1H), 7.70 (d, J=8.2 Hz, 2H), 7.67 (d, J=7.9 Hz, 1H), 7.60 (d, J=7.1 Hz, 1H), 7.36 (d, J=8.3 Hz, 2H), 7.27 (ddd, J=1.1, 4.9, 7.5 Hz, 1H), 6.79 (d, J=1.8 Hz, 1H), 6.60 (dd, J=2.0, 7.1 Hz, 1H), 5.18 (s, 2H), 4.17-3.96 (m, 2H), 3.04-2.91 (m, 1H), 2.38 (td, J=7.6, 12.6 Hz, 1H), 2.06-1.80 (m, 2H). MS ESI calculated value $C_{22}H_{21}N_3O_4$ [M+H]+ 392, measured value 392.

Embodiment 19

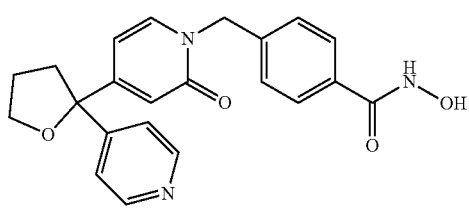

19-7

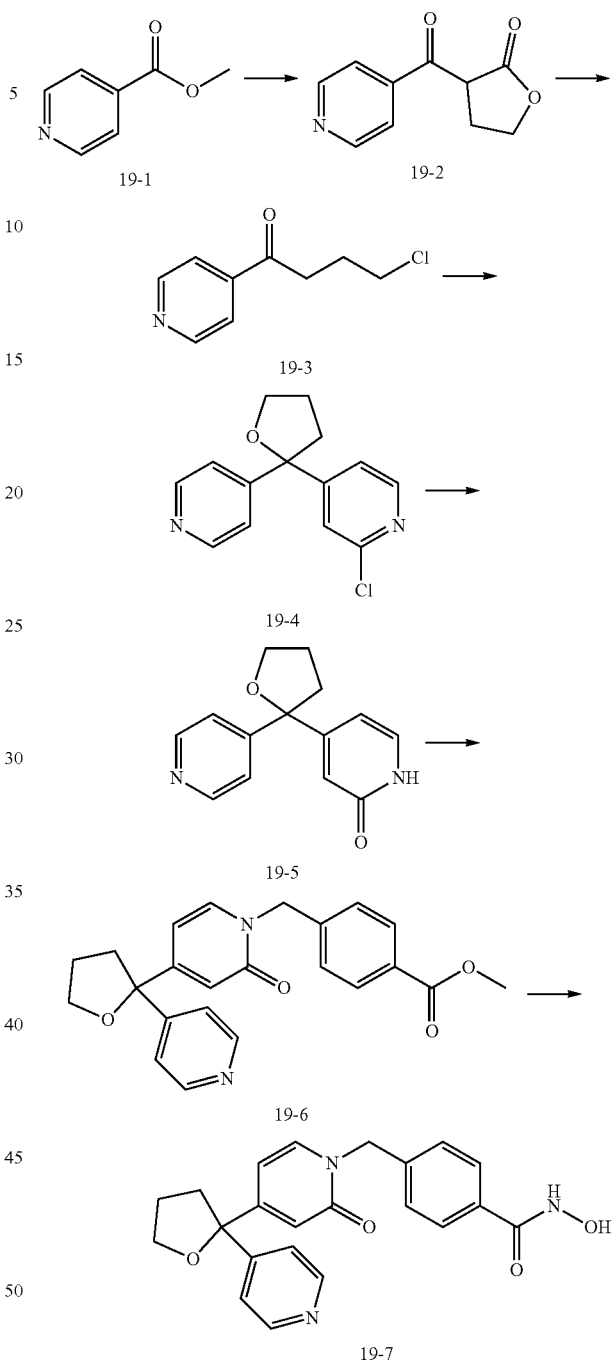

Step 1: At 0° C., sodium hydride (1.06 g, 26.38 mmol, purity 60%, 2.27 eq) was added into 1, 4-butyrolactone (1.00 g, 11.62 mmol, 884.96 μL, 1.00 eq) in tetrahydrofuran (5.00 mL) solution, then stirred at 0° C. for 30 mins, the compound 19-1 (2.39 g, 17.43 mmol, 2.06 mL, 1.50 eq) in tetrahydrofuran (2.00 mL) solution was added at 0° C., then stirred at 20° C. for 2 hours. Saturated ammonium chloride solution water and EtOAc were added into the reaction mixture. The aqueous phase was concentrated and added acetone, then stirred and filtered, the mother solution was concentrated to give the compound 19-2, which was used directly in the next step.

Step 2: The mixture of the compound 19-2 (1.50 g, 7.85 mmol, 1.00 eq) and 36% hydrochloric acid (15.30 g, 151.11 mmol, 15.00 mL, 19.26 eq) was heated to 80° C., the reaction was stirred for 2 hours. Then the reaction mixture was poured into 0° C. ice water, then extracted by EtOAc, the organic phase was washed by brine, dried over anhydrous sodium sulfate, filtered and concentrated, then purified by silica gel column to give the compound 19-3, which was used directly in the next step.

Step 3: At −68° C., N-butyllithium hexanesolution (2.5 M, 1.44 mL, 1.10 eq) was added dropwise into 2-fluoro-4-iodopyridine (782.97 mg, 3.27 mmol, 1.00 eq) toluene (5.00 mL) solution, followed by addition of the compound 19-3 (600.00 mg, 3.27 mmol, 1.00 eq) in toluene (1.00 mL) solution, the reaction gradually heated to 20° C., the reaction was stirred for 12 hours. Saturated ammonium chloride solution and water were added into the reaction mixture, then extracted by EtOAc, the organic phase was washed by saturated brine, dried over anhydrous sodium sulfate, filtered and concentrated, then purified by silica gel column to give the compound 19-4. MS ESI calculated value $C_{14}H_{13}ClN_2O$ [M+H]+ 261.0, measured value 261.0.

Step 4: Potassium hydroxide (221.07 mg, 3.94 mmol, 2.00 eq), tris(dibenzylideneacetone) dipalladium (180.40 mg, 197.00 μmol, 0.10 eq) and 2-di-tertbutylphosphine-2′, 4′, 6′-triisopropylbiphenyl (83.65 mg, 197.00 μmol, 0.10 eq) were added into the compound 19-4 (513.00 mg, 1.97 mmol, 1.00 eq) in dioxane (5.00 mL) and water (1.00 mL) solution, then stirred at 100° C. for 2 hours. Water was added into the reaction mixture, then extracted by EtOAc, washed by brine, dried over anhydrous sodium sulfate, filtered and concentrated. After concentration, the mixture was then purified by silica gel column to give the compound 19-5. MS ESI calculated value $C_{14}H_{14}N_2O_2$ [M+H]+ 243, measured value 243.

Step 5: At 0° C., sodium hydride (47.55 mg, 1.19 mmol, purity 60%, 1.20 eq) was added into 19-5 (240.00 mg, 990.63 μmol, 1.00 eq) in N, N-dimethylformamide (5.00 mL) solution, methyl 4-bromomethylbenzoate (226.92 mg, 990.63 μmol, 1.00 eq) in N, N-dimethylformamide (1.00 mL) solution was added into the reaction system, and stirred at 20° C. for 2 hours. Saturated ammonium chloride solution and water was added into the reaction mixture, then extracted by EtOAc, washed by brine, dried over anhydrous sodium sulfate, followed by concentration and then purified by chromatography to give the compound 19-6. MS ESI calculated value $C_{23}H_{22}N_2O_4$ [M+H]+ 391.1, measured value 391.1

Step 6: Sodium hydroxide (13.52 mg, 338.08 μmol, 2.00 eq) and hydroxylamine solution (1.00 mL, 50% purity) were added into the compound 19-6 (66.00 mg, 169.04 μmol, 1.00 eq) in methanol (5.00 mL) solution, and stirred at 20° C. for 12 hours. After the reaction mixture was concentrated, it was purified by reverse phase preparative column to give the compound 19-7. $^1$H NMR (400 MHz, MeOD) δ 8.51 (d, J=6.1 Hz, 2H), 8.45 (brs, 1H), 8.47-8.41 (m, 1H), 7.71 (d, J=8.3 Hz, 2H), 7.65 (d, J=7.2 Hz, 1H), 7.62-7.56 (m, 2H), 7.37 (d, J=8.3 Hz, 2H), 6.76 (d, J=1.9 Hz, 1H), 6.49 (dd, J=1.9, 7.2 Hz, 1H), 5.20 (s, 2H), 4.13-3.99 (m, 2H), 2.58 (t, J=7.2 Hz, 2H), 2.09-1.88 (m, 2H). MS ESI calculated value $C_{22}H_{21}N_3O_4$ [M+H]+ 392, measured value 392.

Embodiment 20

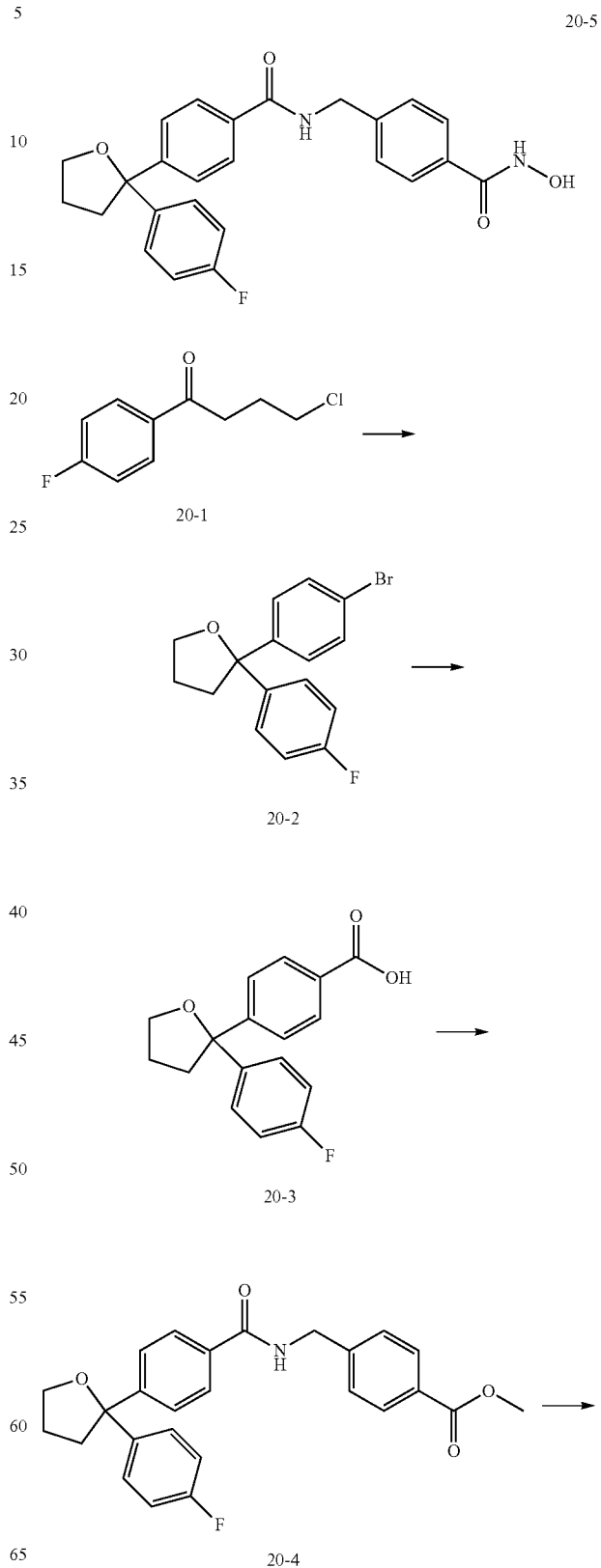

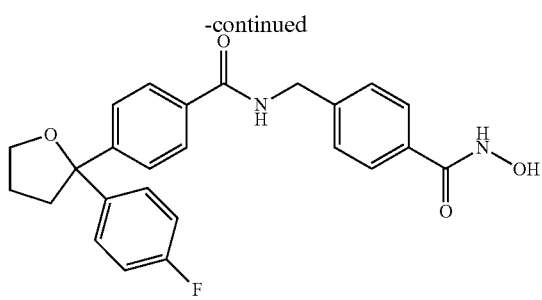

20-5

Step 1: Under N₂ protection, at −70° C., n-BuLi (2.5 M, 23.33 mL, 1.10 eq) was added dropwise into 1-bromo-4-iodobenzene (15.00 g, 53.02 mmol, 1.00 eq) in THF (150.00 mL) solution, after the addition was completed, the reaction was continued stirring at the temperature for 30 mins. Compound 20-1 (10.64 g, 53.02 mmol, 8.72 mL, 1.00 eq) was then added dropwise into the yellow suspension above, when the addition is complete, the system temperature was raised to 20° C. and stirred for 12 hours. When the reaction was completed, it was quenched by water (300 mL) and extracted by EtOAc (100 mL×3), the combined extracts was washed by brine (100 mL), then dried over anhydrous Na₂SO₄, filtered and concentrated under reduced temperature to give the compound 20-2. $^1$H NMR (400 MHz, CDCl₃) δ 7.25-7.50 (m, 6H), 6.90-7.00 (m, 2H), 4.03 (t, J=6.8 Hz, 2H), 2.40-2.55 (m, 2H), 1.85-2.00 (m, 2H).

Step 2: Under N₂ protection, at −70° C., n-BuLi (2.5 M, 1.24 mL, 1.00 eq) was added dropwise into the compound 20-2 (1.00 g, 3.11 mmol, 1.00 eq) in THF (15.00 mL) solution, when the addition was completed, the mixture was continued stirring at the temperature for 30 mins. Then drikold (about 5 g) was added into the system above and gradually raise the temperature to 20° C. and stirred for 2 hours. When the reaction was completed, the mixture was poured into water (30 mL), 2 M KOH was used to adjust pH=9, then extracted by EtOAc (10 mL×2). Then the aqueous phase was adjusted to pH=5 using 2M HCl, then extracted by EtOAc (20 mL×3. The extracts was washed by brine (30 mL), then dried over anhydrous Na₂SO₄, filtered and concentrated under reduced temperature to give the compound 20-3. $^1$H NMR (400 MHz, D MSO-d₆) δ 7.87 (d, J=8.0 Hz, 2H), 7.56 (d, J=7.6 Hz, 2H), 7.40-7.50 (m, 2H), 7.12 (t, J=8.8 Hz, 2H), 3.90-4.00 (m, 2H), 2.51-2.60 (m, 2H), 1.75-1.90 (m, 2H).

Step 3: Compound 20-3 (100.00 mg, 349.28 μmol, 1.00 eq), HATU (159.37 mg, 419.14 μmol, 1.20 eq) and DIEA (67.71 mg, 523.92 μmol, 91.50 μL, 1.50 eq) in MeCN (10.00 mL) solution were stirred at 20° C. for 30 mins, then 4-(aminomethyl) methyl benzoate (70.43 mg, 349.28 μmol, 1.00 eq, hydrochloride) was added into the above solution then continued stirring at 20° C. for 12 hours. When the reaction was completed, the reaction mixture was concentrated, the residue was slurried by H₂O (3 mL), and filtered and dried in vacuum to give the compound 20-4, which was used directly in the next step. MS ESI calculated value C₂₆H₂₄FNO₄ [M+H]⁺ 434, measured value 434.

Step 4: At 20° C., NH₂OH.H₂O (3.00 mL, 50% solution) and NaOH (2 M, 1.50 mL) solution was added dropwise in sequence into the compound 20-4 (150.00 mg, 346.04 μmol, 1.00 eq) in DCM (4.00 mL) and MeOH (2.00 mL) solution. When the addition was completed, the reaction mixture was heated and refluxed for 6 hours. Then the mixture was directly purified by preparative HPLC (0.1% TFA) to give the compound 20-5. $^1$H NMR (400 MHz, D MSO-d₆) δ 11.15 (brs, 1H), 8.95-9.05 (m, 2H), 7.80 (d, J=8.0 Hz, 2H), 7.67 (d, J=8.0 Hz, 2H), 7.52 (d, J=8.4 Hz, 1H), 7.40-7.50 (m, 2H), 7.33 (d, J=8.4 Hz, 2H), 7.02-7.10 (m, 2H), 4.67 (d, J=5.6 Hz, 2H), 3.92 (t, J=6.8 Hz, 2H), 2.51-2.60 (m, 2H), 1.85-1.95 (m, 2H). MS ESI calculated value C₂₅H₂₃FN₂O₄ [M+H]+ 435, measured value 435.

Embodiment 21

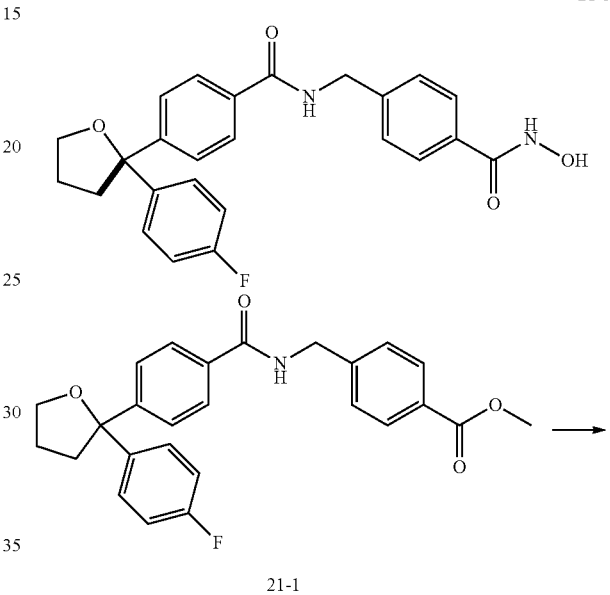

21-3

21-1

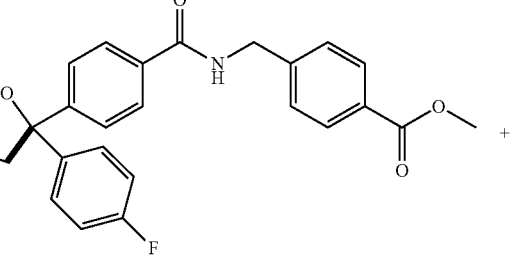

21-2 (P1)

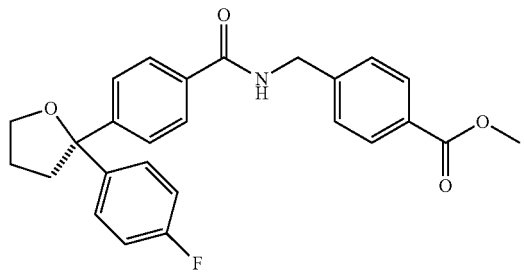

22-1 (P2)

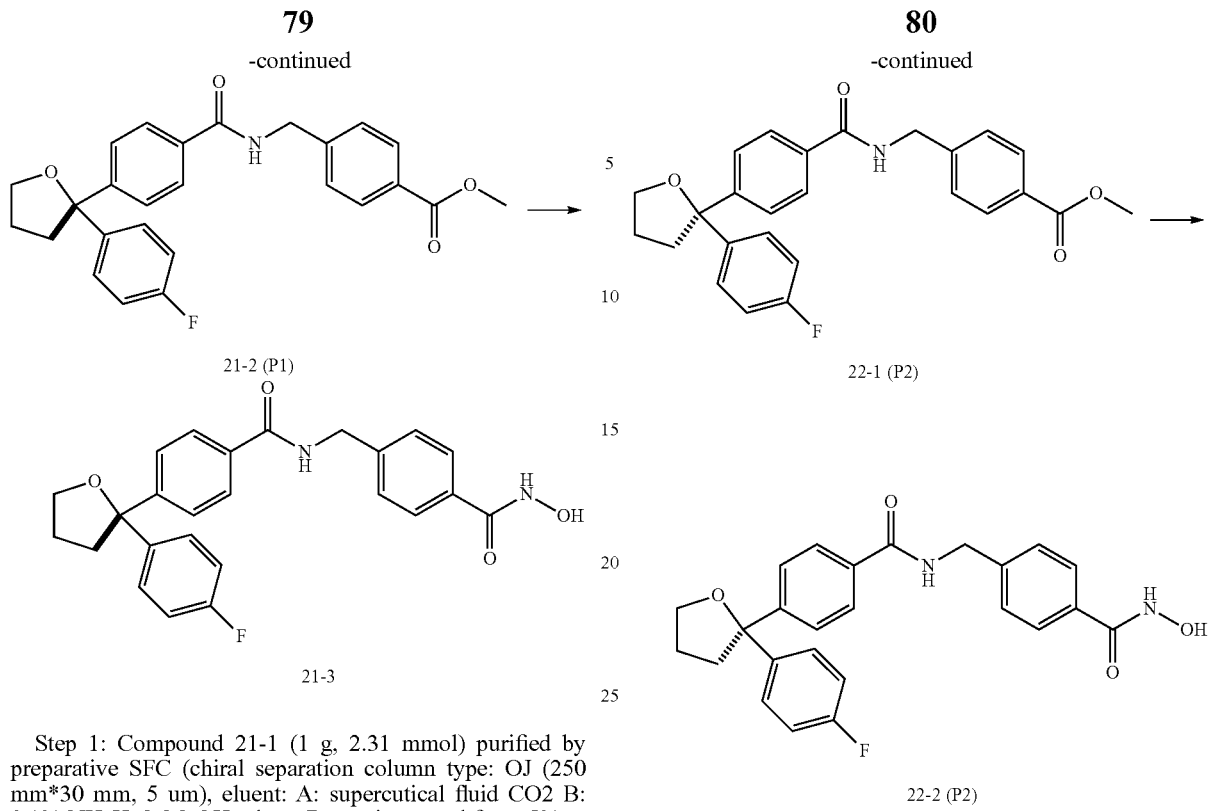

Step 1: Compound 21-1 (1 g, 2.31 mmol) purified by preparative SFC (chiral separation column type: OJ (250 mm*30 mm, 5 um), eluent: A: supercutical fluid CO2 B: 0.1% NH₃H₂O MeOH, phase B was increased from 5% to 40% in 5.5 mins, then eluted by keeping 40% phase B for 3 mins, finally 5% phase B was kept for 1.5 mins, flow velocity 60 mL), the two isomers were obtained, 21-2(P1) and 22-1(P2), remaining times were 6.474 min and 7.256 min, respectively.

Step 2: At 0° C., NH₂OH.H₂O (4.00 mL, 50% solution) and NaOH (2 M, 4.00 mL) were added dropwise in sequence into the compound 21-2(P1) (450.00 mg, 1.04 mmol, 1.00 eq) in DCM (4.00 mL) and MeOH (4.00 mL) solution, when the addition was completed, the mixture was continued stirring at that temperature for 2 hours. Most of the solvent was eliminated by concentration under reduced pressure, the solvent remained was cooled down to 0° C. and by using 8 M HCl, the pH=7-8 were adjusted, the precipitates were filtered, the residue was washed by H₂O (5 mL×2), then dried under reduced pressure to give the compound 21-3. ¹H NMR (400 MHz, MeOD) δ 7.79 (d, J=8.4 Hz, 2H), 7.71 (d, J=8.4 Hz, 2H), 7.54 (d, J=8.4 Hz, 2H), 7.40-7.05 (m, 4H), 6.95-7.05 (m, 2H), 4.60 (d, J=4.0 Hz, 2H), 4.02 (t, J=7.2 Hz, 2H), 2.50-2.60 (m, 2H), 1.85-2.00 (m, 2H). MS ESI calculated value $C_{25}H_{23}FN_2O_4$ [M+H]⁺ 435, measured value 435.

Embodiment 22

Step 1: At 0° C., NH₂OH.H₂O (4.00 mL, 50% solution) and NaOH (2 M, 4.00 mL) were added dropwise in sequence into the compound 22-1(P2) (450.00 mg, 1.04 mmol, 1.00 eq) in DCM (4.00 mL) and MeOH (4.00 mL) solution, when the addition was complete, the mixture was continued stirring at that temperature for 2 hours. Most of the solvent was eliminated by concentration under reduced pressure, the solvent remained was cooled down to 0° C. then adjusted pH=7-8 using 8 M HCl, aftertreatment to give the compound 22-2(P2). ¹H NMR (400 MHz, MeOD) δ 7.79 (d, J=8.4 Hz, 2H), 7.71 (d, J=8.4 Hz, 2H), 7.54 (d, J=8.4 Hz, 2H), 7.40-7.05 (m, 4H), 6.95-7.05 (m, 2H), 4.60 (s, 2H), 4.02 (t, J=7.2 Hz, 2H), 2.50-2.60 (m, 2H), 1.85-2.00 (m, 2H). MS ESI calculated value $C_{25}H_{23}FN_2O_4$ [M+H]⁺ 435, measured value 435.

Embodiment 23

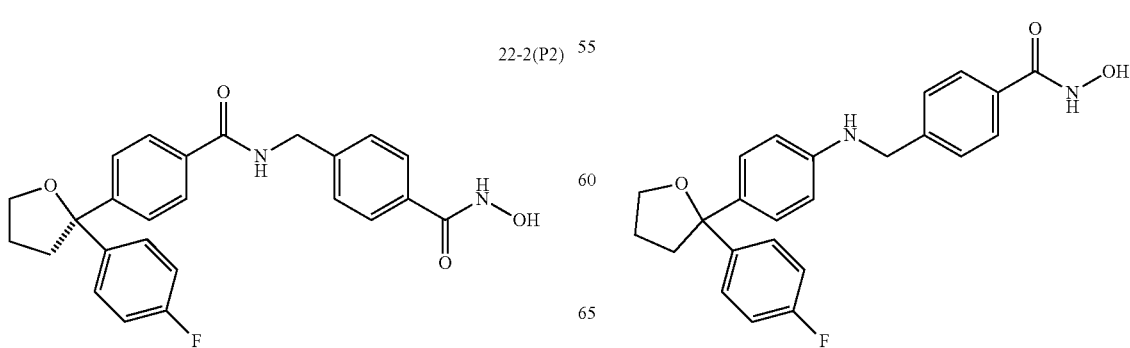

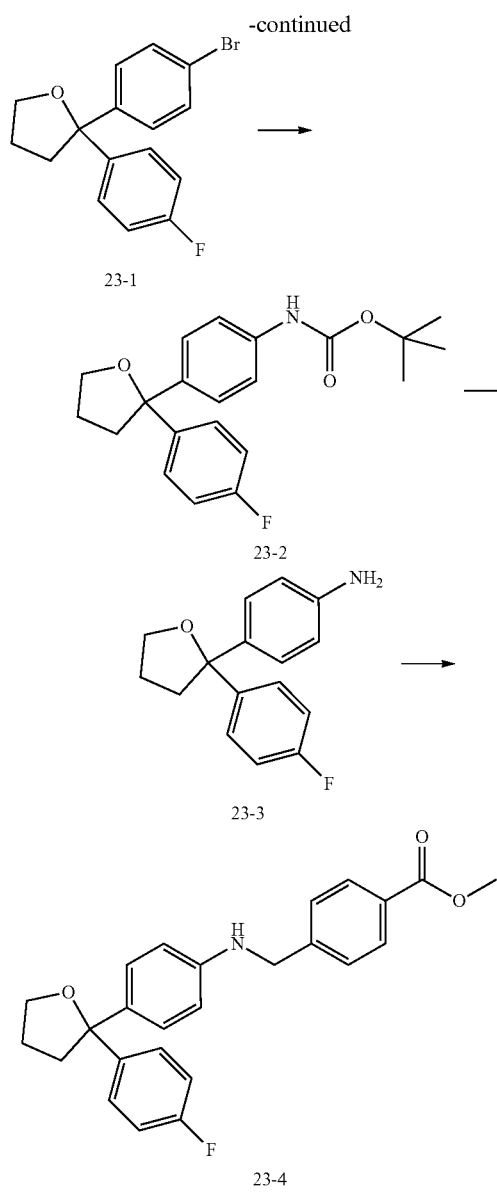

extracted by EtOAc (50 mL×3), the combined extracts was washed by brine (80 mL), then dried over anhydrous Na2SO4, followed by filtration and concentration under reduced pressure. The product was passed through silica gel column chromatography (PE/EtOAc=9/1) to give the compound 23-2. MS ESI calculated value C21H24FNO3 [M+H]+ 358, measured value 358.

Step 2: At 25° C., TFA (2.00 mL) was added into the compound 23-2 (250.00 mg, 699.46 μmol, 1.00 eq) in DCM (5.00 mL) solution and stirred for 30 mins, then concentrated under reduced temperature to give the compound 23-3. MS ESI calculated value $C_{16}H_{16}FNO$ $[M+H]^+$ 258, measured value 258.

Step 3: Compound 23-3 (250.00 mg, 673.26 μmol, 1.00 eq, TFA salt), methyl 4-(bromomethyl) benzoate (154.22 mg, 673.26 μmol, 1.00 eq) and $K_2CO_3$ (139.58 mg, 1.01 mmol, 1.50 eq) in DMF (5.00 mL) solution were stirred at 25° C. for 6 hours. The reaction mixture was then poured into water (50 mL), and extracted by EtOAc (30 mL×2, the combined extracts was washed by brine (30 mL), then dried over anhydrous $Na_2SO_4$, filtered and concentrated under reduced temperature to give the compound 23-4, which was used directly in the next step. MS ESI calculated value $C_{25}H_{24}FNO_3$ $[M+H]^+$ 406, measured value 406.

Step 4: At 25° C., $NH_2OH.H_2O$ (3.00 mL, 50% solution) and NaOH (2 M, 1.50 mL) solution were added dropwise in sequence into the compound 23-4 (250.00 mg, 616.58 mmol, 1.00 eq) in DCM (4.00 mL) and MeOH (2.00 mL) solution, then the reaction system temperature was raised to 50° C. and stirred for 2 hours. Most of the solvent was eliminated by concentration under reduced pressure, the rest of the solution was purified by preparative HPLC (0.1% $NH_4OH$) to give the compound 23-5. $^1H$ NMR (400 MHz, D MSO-$d_6$) δ 11.04 (brs, 1H), 9.03 (brs, 1H), 7.67 (d, J=8.0 Hz, 2H), 7.35-7.45 (m, 4H), 6.95-7.05 (m, 4H), 6.45 (d, J=8.4 Hz, 2H), 6.28 (t, J=5.6 Hz, 1H), 4.25 (d, J=6.0 Hz, 2H), 3.70-3.90 (m, 2H), 2.20-2.45 (m, 4H), 1.65-1.90 (m, 2H). MS ESI calculated value $C_{25}H_{24}FNO_3$ [M+H]+ 406, measured value 406.

Embodiment 24

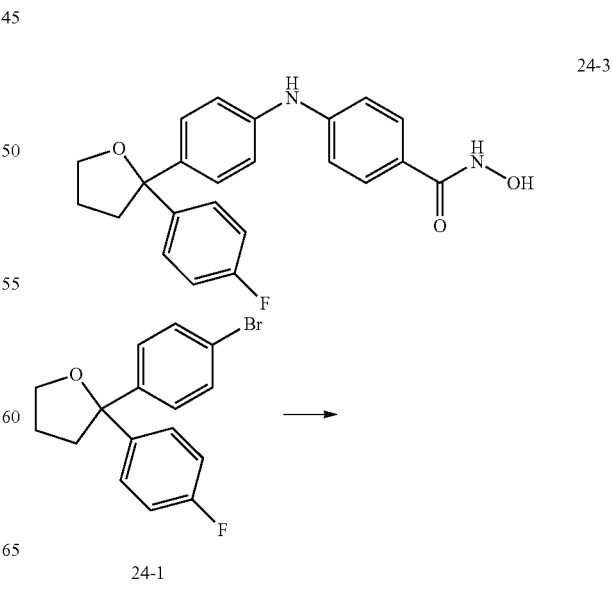

Step 1: Under $N_2$ protection, compound 23-1 (1.00 g, 3.11 mmol, 1.00 eq), tert-butoxycarbonyl ammonia (546.50 mg, 4.67 mmol, 1.50 eq), Xantphos (179.95 mg, 311.00 μmol, 0.10 eq), $Pd_2(dba)_3$ (142.39 mg, 155.50 μmol, 0.05 eq) and $Cs_2CO_3$ (1.52 g, 4.67 mmol, 1.50 eq) in DMF (15.00 mL) solution were heated to 100° C. and stirred for 12 hours. The reaction mixture was poured into water (100 mL), and Embodiment 25

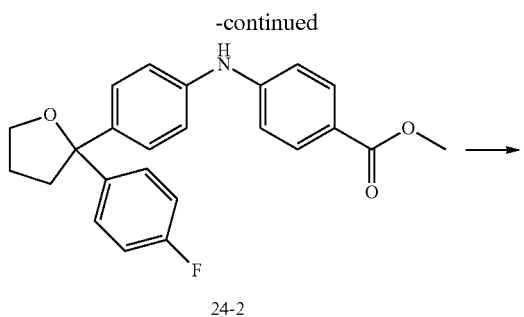

24-2

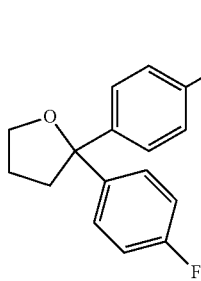

24-3

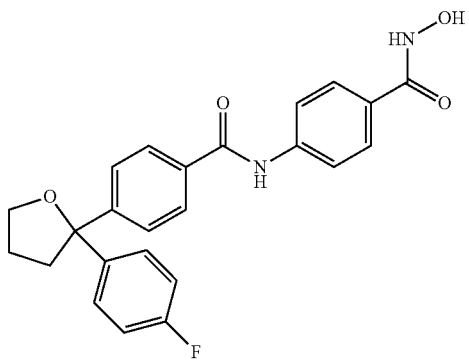

25-3

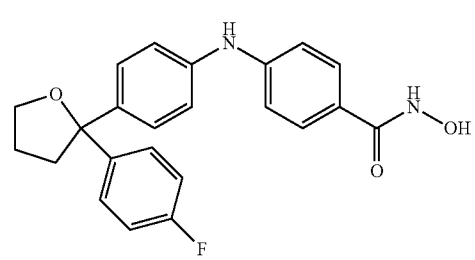

25-1

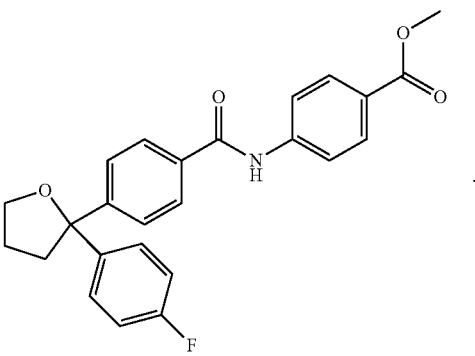

25-2

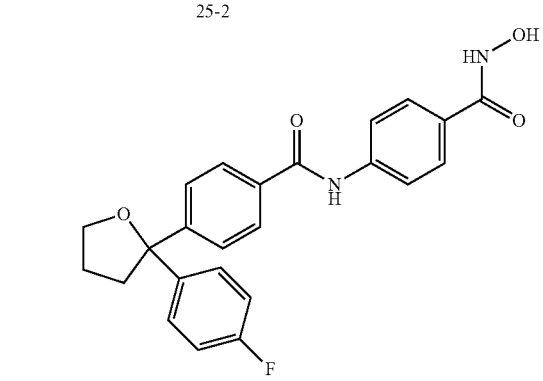

25-3

Step 1: Under N₂ protection, compound 24-1 (300.00 mg, 934.06 μmol, 1.00 eq), methyl 4-aminobenzoate (141.19 mg, 934.06 μmol, 1.00 eq), Xantphos (108.09 mg, 186.81 μmol, 0.20 eq), Cs₂CO₃ (456.50 mg, 1.40 mmol, 1.50 eq) and Pd₂(dba)3 (85.53 mg, 93.41 μmol, 0.10 eq) in DMF (15.00 mL) solution were heated to 100° C. and stirred for 8 hours. The reaction mixture was poured into water (150 mL), and extracted by EtOAc (80 mL×2), the combined extracts was washed by brine (50 mL), then dried over anhydrous Na₂SO₄, followed by filtration and concentration under reduced pressure. The product was purified by silica gel column chromatography (PE/EtOAc=5/1) to give the compound 24-2. MS ESI calculated value $C_{24}H_{22}FNO_3$ [M+H]+ 392, measured value 392.

Step 2: At 25° C., NH2OH.H2O (2.00 mL, 50% solution) and NaOH (2 M, 2.00 mL) solution were added dropwise in sequence into the compound 24-2 (250.00 mg, 638.67 μmol, 1.00 eq) in DCM (2.00 mL) and MeOH (4.00 mL) solution. When the addition was complete, the reaction was continued stirring at 20° C. for 12 hours. Most of the solvent was eliminated by concentration under reduced pressure, the residue was dissolved by DMSO (5 mL), the solution obtained was purified by preparative HPLC (0.1% NH₄OH) to give the compound 24-3.

¹H NMR (400 MHz, D MSO-d6) δ 10.88 (brs, 1H), 8.85 (brs, 1H), 8.50 (brs, 1H), 6.90-7.80 (m, 12H), 3.80-4.00 (m, 2H), 2.30-2.45 (m, 2H), 1.80-1.90 (m, 2H). MS ESI calculated value $C_{23}H_{21}FN_2O_3$ [M+H]+ 393, measured value 393.

Step 1: Compound 25-1 (800.00 mg, 2.79 mmol, 1.00 eq), HATU (1.59 g, 4.19 mmol, 1.50 eq) and DIEA (722.26 mg, 5.59 mmol, 976.03 μL, 2.00 eq) in MeCN (5.00 mL) solution were stirred at 20° C. for 20 mins, then methyl 4-aminobenzoate (422.38 mg, 2.79 mmol, 1.00 eq) was added into above solution, then continued stirring at that temperature for 12 hours. The solvent was eliminated by concentration under reduced temperature, the solid remained was dissolved by EtOAc (80 mL), and then washed, in turn, by 2M NaOH solution (30 mL×2) and brine (50 mL), then dried over anhydrous Na2SO4, and filtered and concentrated under reduced temperature. The product was purified by silica gel column chromatography (PE/EtOAc=10/1) to give the compound 25-2. MS ESI calculated value $C_{25}H_{22}FNO_4$ [M+H]+ 420, measured value 420.

Step 2: At 20° C., NH$_2$OH.H$_2$O (11.00 mL, 50% solution) and NaOH (2 M, 10.00 mL) solution were added dropwise in sequence into the compound 25-2 (1.10 g, 2.62 mmol, 1.00 eq) in DCM (10.00 mL) and MeOH (20.00 mL) solution, when the addition was completed, the mixture was continued stirring at that temperature for 12 hours. Most of the solvent was eliminated by concentration under reduced pressure, the residue was dissolved to clarification (溶清) by DMSO (5 mL), solution obtained was purified by preparative HPLC (0.1% HCl) to give the compound 25-3.

$^1$H NMR (400 MHz, D MSO-d$_6$) δ 11.14 (brs, 1H), 10.39 (brs, 1H), 7.86 (d, J=8.4 Hz, 2H), 7.82 (d, J=8.4 Hz, 2H), 7.40 (d, J=8.8 Hz, 2H), 7.61 (d, J=8.8 Hz, 2H), 7.45-7.55 (m, 2H), 7.13 (t, J=8.8 Hz, 2H), 3.96 (t, J=7.6 Hz, 2H), 2.58 (t, J=6.8 Hz, 2H), 1.80-1.95 (m, 2H). MS ESI calculated value $C_{24}H_{21}FN_2O_4$ [M+H]+ 421, measured value 421.

Embodiment 26

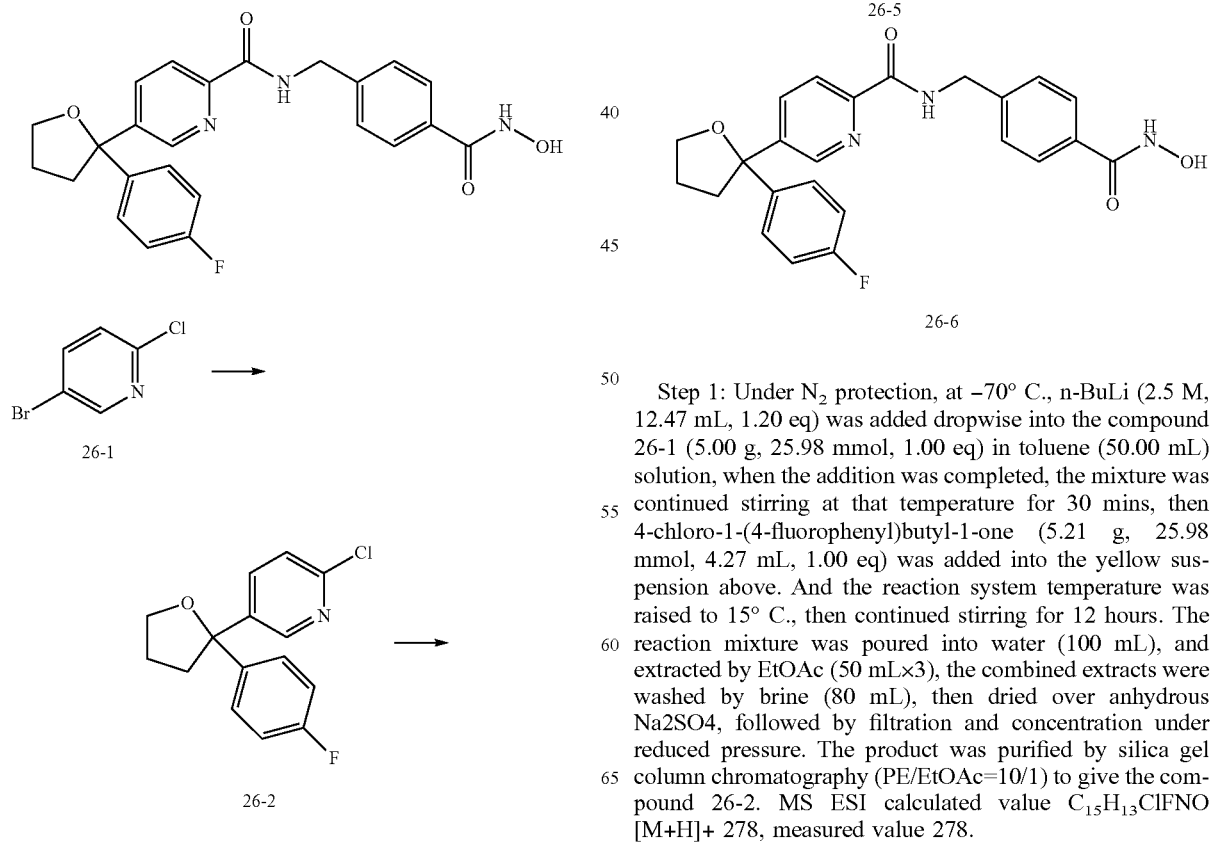

Step 1: Under N$_2$ protection, at −70° C., n-BuLi (2.5 M, 12.47 mL, 1.20 eq) was added dropwise into the compound 26-1 (5.00 g, 25.98 mmol, 1.00 eq) in toluene (50.00 mL) solution, when the addition was completed, the mixture was continued stirring at that temperature for 30 mins, then 4-chloro-1-(4-fluorophenyl)butyl-1-one (5.21 g, 25.98 mmol, 4.27 mL, 1.00 eq) was added into the yellow suspension above. And the reaction system temperature was raised to 15° C., then continued stirring for 12 hours. The reaction mixture was poured into water (100 mL), and extracted by EtOAc (50 mL×3), the combined extracts were washed by brine (80 mL), then dried over anhydrous Na2SO4, followed by filtration and concentration under reduced pressure. The product was purified by silica gel column chromatography (PE/EtOAc=10/1) to give the compound 26-2. MS ESI calculated value $C_{15}H_{13}ClFNO$ [M+H]+ 278, measured value 278.

Step 2: The mixture of compound 26-2 (1.00 g, 3.60 mmol, 1.00 eq), DPPP (148.51 mg, 360.00 μmol, 0.10 eq), Pd$_2$(dba)$_3$ (164.86 mg, 180.00 μmol, 0.05 eq) and TEA (546.54 mg, 5.40 mmol, 748.68 μL, 1.50 eq) in D MSO (10.00 mL) and MeOH (3.00 mL) solution was heated to 80° C., then stirred under CO (50 psi) atmosphere for 12 hours. The reaction mixture was poured into water (100 mL), and extracted by EtOAc (50 mL×3), the combined extracts were washed by brine (80 mL), then dried over anhydrous Na$_2$SO$_4$, then filtered and concentrated under reduced temperature to give the compound 26-3. MS ESI calculated value C$_{17}$H$_{16}$FNO$_3$ [M+H]+ 302, measured value 302.

Step 3: The mixed solution of compound 26-3 (1.00 g, 3.32 mmol, 1.00 eq) and NaOH (265.60 mg, 6.64 mmol, 2.00 eq) 的 MeOH (10.00 mL) and H$_2$O (10.00 mL) was heated, refluxed and stirred for 2 hours. Then MeOH was eliminated by concentration under reduced temperature, the aqueous phase was extracted by EtOAc (10 mL×2), then the aqueous phase was adjusted the pH=6 by using hydrochloric acid. Finally the mixture was concentrated under reduced temperature to give the compound 26-4. MS ESI calculated value C$_{16}$H$_{14}$FNO$_3$ [M+H]+ 288, measured value 288.

Step 4: 26-4 (900.00 mg, 3.13 mmol, 1.00 eq), HATU (1.79 g, 4.70 mmol, 1.50 eq) and DIEA (1.21 g, 9.40 mmol, 3.00 eq) in MeCN (15.00 mL) solution were stirred at 20° C. for 30 mins. Then 4-(aminomethyl) methyl benzoate (631.71 mg, 3.13 mmol, 1.00 eq, hydrochloride) was added into the above solution and stirred at 20° C. for 3 hours. The mixture was concentrated under reduced temperature, then diluted by H$_2$O (80 mL), then extracted by EtOAc (30 mL×3), the combined extracts were washed by brine (30 mL), then dried over anhydrous Na2SO4, followed by filtration and concentration under reduced pressure. The product was finally passed through column chromatography (PE/EtOAc=5/1 to 3/1) to give 26-5. MS ESI calculated value C$_{25}$H$_{23}$FN$_2$O$_4$ [M+H]+ 435, measured value 435.

Step 5: At 0° C., NH$_2$OH.H$_2$O (47.04 mg, 460.34 μmol, 2.00 mL, 50% solution) and NaOH (2 M, 230.17 μL) solution were added dropwise in sequence into 26-5 (200.00 mg, 460.34 μmol, 1.00 eq) in DCM (2.00 mL) and MeOH (4.00 mL) solution, after the completion of the addition, the mixture was continued stirring at that temperature for 3 hours. Most of the solvent was eliminated by concentration under reduced pressure, then dissolve to clarification by DMSO (5 mL), the solution obtained was purified by preparative HPLC (0.05% HCl) to give 26-6. $^1$H NMR (400 MHz, D MSO-d$_6$) δ 11.15 (brs, 1H), 10.22 (brs, 1H), 9.35 (t, J=6.4 Hz, 1H), 8.72 (d, J=1.5 Hz, 1H), 8.01-8.07 (m, 1H), 7.94-8.00 (m, 1H), 7.68 (d, J=8.3 Hz, 2H), 7.49-7.56 (m, 2H), 7.34 (d, J=8.3 Hz, 2H), 7.15 (t, J=8.9 Hz, 2H), 4.51 (d, J=6.3 Hz, 2H), 3.98 (t, J=7.2 Hz, 2H), 2.62 (t, J=7.2 Hz, 2H), 1.89 (qd, J=7.2, 5.1 Hz, 2H). MS ESI calculated value C$_{24}$H$_{22}$FN$_3$O$_4$ [M+H]+ 436, measured value 436.

Experimental Example 1: In Vitro Evaluation

The degree of deacetylation of the acetylated substrate was determined by detecting the changes in the intensity of the fluorescent signal in the 384-well microplate using EnVision® microplate reader, the half inhibitory comcentration IC50 value of the compound inhibitor was used as a reference to evaluate the inhibitory effect of the compound on the histone deacetylase (HDAC).

1. Steps and Methods of the Assay:
   1.1 Compound Dilution and Sample Loading:
   The compound was diluted by DMSO to 2 mM, and then added to 384 compound plate, then the solution was diluted 3 times, 10 gradients and double duplicate wells using a Bravo automated liquid workstation; then 0.15 μL of the compound was transferred from 384 compound plate to 384 assay plate by Echo liquid handler.
   1.2 configuration of the assay buffer: the configuration contains 20 mM Hepes, 137 mM NaCl, 2.7 mM KCl, 1 mM MgCl$_2$, 0.05% BSA, 0.5 mM TCEP of 1× assay buffer, each of which is represented by final concentration thereof.
   1.3 Configuration of the 1.5× Enzyme Mixture:
   The rapidly dissolving histone deacetylase was added to the 1× assay buffer and mixed well. The 1.5× enzyme mixture was added to a 20 μL to 384-well assay plate, mixed by centrifugation, placed in a 23° C. incubator, and the enzyme was incubated with the compound for 20 minutes.
   Configuration of 3× Substrate Mixture:
   The 3× substrate solution was configured by 1× assay buffer, and then mixed well. 10 μL was added to a 384-well assay plate, mixed by centrifugation, and placed in a 23° C. incubator for 90 minutes for reaction.
   1.5 Preparation of Terminating the Mixture:
   The terminating mixture of trypsin and the positive compound SAHA (Vorinostat, vorinostat) was configured with 1× assay buffer and mixed well. The reaction was terminated by adding 30 μL to a 384-well assay plate, then centrifuged, and placed in a 23° C. incubator for 60 minutes.
   1.6 Readings:
   After termination of the reaction for 60 minutes, the 384-well assay plate was placed on an Envision micro-plate reader and the fluorescence value was read.
   1.7 Data analysation: the data was analyzed by using XLfit5 software to calculate the IC50 value of the compound.

TABLE 1

In vitro screening test results of the compounds of the invention

| The compounds formed by the embodiment | HDAC 6 IC50(nM) | HDAC 1 IC50(nM) |
|---|---|---|
| Embodiment1 | A | D |
| Embodiment2 | A | D |
| Embodiment3 | A | C |
| Embodiment4 | A | C |
| Embodiment5 | A | C |
| Embodiment6 | A | C |
| Embodiment7 | A | D |
| Embodiment8 | A | D |
| Embodiment9 | C | D |
| Embodiment10 | B | D |
| Embodiment11 | A | C |
| Embodiment12 | A | C |
| Embodiment13 | A | C |
| Embodiment14 | A | C |
| Embodiment15 | A | C |
| Embodiment16 | A | C |
| Embodiment17 | A | C |
| Embodiment18 | A | C |
| Embodiment19 | A | C |
| Embodiment20 | A | C |
| Embodiment21 | A | C |
| Embodiment22 | A | C |
| Embodiment23 | B | D |
| Embodiment24 | B | D |
| Embodiment25 | B | D |
| Embodiment26 | A | C |

Remarks: A ≤ 10 nM; 10 nM < B ≤ 50 nM; 50 nM < C ≤ 200 nM; D > 200 nM;
Conclusion: the inhibitory effect of the compound of the present invention on HDAC6 is signicicant, while the inhibitory effect on HDAC1 is weak, which shows the property of high selectivity.

Experimental Example 2: Pharmacokinetic Evaluation of the Compounds

Purpose of the experiment: test the compound's pharmacokinetics in male beagle dogs Experimental materials: Beagle (male, 6-15 kg, 6 months-4 age, Marshall Bioresources, Beijing, China)

Experimental Operation:

The Beagle's pharmacokinetic characteristics after oral administration of the compound were tested by a standard scheme. In the experiment, the candidate compound was formulated into a uniform suspension and administered to a beagle dog for single oral administration. Oral menstruum was formed by a certain proportion of polyethylene glycol-polyoxyethylene castor oil aqueous solution. Blood samples within 24 hours was collected, then centrifuged at 3000 g for 10 minutes, the supernatant was separated to obtain plasma samples, 30 μL of plasma samples was added into 300 μL of internal standard acetonitrile solution to precipitate protein, 30 μL of supernatant was obtained after vortex and centrifugation, and then equal volume of water was added, followed by vortex and centrifugation for another time to collect the supernatant, and the plasma concentration was quantitatively analyzed by LC-MS/MS analysis, and the pharmacokinetic parameters such as peak concentration, peak-reached time, half-life, and area under the administrating curve were calculated.

The experimental results are shown in the Table 2

TABLE 2 pharmacokinetic test results

| Candidate (componds of the embodiment) | Clearance rate (mL/min/kg) | Half-life $T_{1/2}$ (h) | Integrated concentration AUC (nM · hr) | bioavailability F (%) |
|---|---|---|---|---|
| Embodiment 26 | 16.0 | 2.14 | 13340 | 53.1 |

Conclusion: the compond of the present invention shows good single or partial canine pharmacokinetic index.

Experimental Example 3: In Vivo Pharmacodynamic Study of Administration Combining with Ixazomib on CB-17 SCID Model of Human Myeloma MM.1S Cells Subcutaneous Xenograft Tumor 1. Purpose of the Experiment:

HDAC inhibitors are widely used in a variety of cancers and can be combined with a variety of drugs to enhance therapeutic effect of the drug, which is a well-recognized anti-tumor target. HDAC inhibitors are widely used in a variety of cancers, and can be combined with a variety of drugs to enhance the therapeutic effect of the drug, such as the combination of panobinostat and the proteasome inhibitor bortezomib can enhance the therapeutic effect against the multiple myeloma and significantly reduce the toxicity.

The purpose of this experiment was to investigate the in vivo therapeutic effect of the compounds of the present invention in combination with proteasome inhibitor Ixazomib on human myeloma MM.1S cell subcutaneous xenografts in the CB-17 SCID model.

2. Methods and Steps of the Experiments 2.1 Cell Culture

Human myeloma MM. S cells were cultured in vitro in a single layer, culture environment was RPMI-1640 medium (supplier: Gibco; Cat. No. 22400-089) supplemented with 10% fetal bovine serum, 37° C. 5% CO2 incubator. Then passage was done by routinely digested with trypsin-EDTA twice a week. When the cell saturation rate reached 80%-90%, the cells were collected, counted, and inoculated.

2.2 Tumor Cell Inoculation 0.2 mL of 5×10$^6$ MM.1S cells were subcutaneously inoculated into the right back of each mouse (Beijing Weitong Lihua Biotechnology Co., Ltd., female, 6-8 weeks old) (PBS: Matrigel=1:1)). Administration by groups was initiated when the average tumor volume reached 100-150 mm$^3$.

2.3 Configuration of the Candidate Compounds

TABLE 3

Methods of configuration of the candidate compounds

| Compound | packing | Methods of configuration | concentration (mg/mL) | Storage condition |
|---|---|---|---|---|
| menstruum | — | 2.5 mL of dimethyl sulfoxide was placed in a 50.0 mL volumetric flask, and 47.5 mL of 10% hydroxypropyl-β-cyclodextrin was added and vortexed to a clear solution. | — | 4° C. |
| Embodiment 26, 30 mg/kg | 3501.04 mg/vial | 53.38 mg of the compound of embodiment 26 was weighted in a brown dispensing bottle, 875 μL of dimethyl sulfoxide was added, vortexed to mix well, then 16.625 mL of 10% hydroxypropyl-β-cyclodextrin was added followed by vortexing and ultrasound to give a clear and transparent solution. | 3.0 | 4° C. |
| Ixazomib, 4 mg/kg | 100.80 mg/vial | 2.83 mg of Ixazomib was weighed into a brown dispensing vial, and 7.001 mL of 5% hydroxypropyl-β-cyclodextrin was added followed by vortexing and ultrasound to give a clear and transparent solution. | 0.4 | 4° C. |

Remarks: the drugs need to be gently mixed well before being administered to the animal.

2.4 Daily Observation of the Experimental Animals

Animals were monitored daily for health and mortality, routine tests includes observations of tumor growth and drug treatment effects on animal performance, such as behavioral activities, food intake (visual inspection only), weight change (measured every other day), appearance signs or other abnormal conditions. The number of animal deaths and side effects in the group were recorded based on the number of animals in each group.

2.5 Tumor Measurement and Experimental Index

The experimental index is to investigate whether tumor growth is inhibited, delayed or cured. Tumor diameters were measured with vernier calipers three times a week. The tumor volume is calculated by: $V=0.5a \times b^2$, where a and b represent the long and short diameters of the tumor, respectively.

The antitumor effect of the compound was evaluated by TGI (%) or relative tumor growth rate T/C (%). TGI (%), reflecting the tumor growth inhibition rate. TGI (%) is calculated by: TGI (%)=((1−(the average tumor volume at the end of a treatment group−the average tumor volume at the beginning of the treatment group))/(the average tumor at the end of the treatment of the solvent control group)−(the average tumor at the beginning of the treatment of the solvent control group))×100%.

Relative tumor proliferation rate T/C (%): the calculation formula is as follows: T/C %=$T_{RTV}/C_{RTV} \times 100\%$ ($T_{RTV}$: RTV of the treatment group; $C_{RTV}$: RTV of the negative control group). The relative tumor volume (RTV) was calculated according to the results of tumor measurement, the calculation formula was RTV=$V_t/V_0$, where $V_0$ is the average tumor volume measured at the time of group administration (ie, $d_0$), and $V_t$ is the average tumor volume measured for a certain measurement, $T_{RTV}$ and $C_{RTV}$ took data from the same day.

Tumor were weighted after the end of the experiment and the percentage of $T/C_{weight}$ was calculated. $T_{weight}$ and $C_{weight}$ represent the tumor weights of the drug-administered group and the menstruum control group, respectively.

3. Statistic Analysis

Statistical analysis includes the mean and standard error (SEM) of tumor volume at each time point for each group. The treatment group showed the best therapeutic effect on the 21st day after the administration at the end of the trial, therefore statistical analysis was performed based on this data to evaluate the difference between the groups. T-test was used for comparison between the two groups, and one-way ANOVA was used for comparison between three or more groups. If there was a significant difference in F values, the test was performed by Games-Howell method. If there is no significant difference in F values, the Dunnet (2-sided) method was used for analysis. All data analysis was performed with SPSS 17.0. A significant difference was considered if $p<0.05$.

4. Experimental Results and Discussion

In the experiments, we have evaluated the in vivo therapeutic effect of the compound from embodiment 26 administrated in combination with Ixazomib on human myeloma MM.1s cell xenograft model. The tumor volume datas of this group at different time points indicated. On the 21st day after the administration started, the tumor volume of the tumor-bearing mice in the solvent control group reached 2611 mm³, and the candidate compound Ixazomib (4 mg/kg) administered alone had a significant antitumor effect compared with the solvent control group (T/C).=34.97%, TGI=68.65%, p=0.030), with a tumor volume of 916 mm³. The compound of the embodiment 26 (30 mg/kg) and Ixazomib (4 mg/kg) combined administrated group had a significant antitumor effect compared with the solvent control group (T/C=8.34%, TGI=96.88%, p=0.001). The tumor volume was 218 mm³.

In summary, in the human myeloma MM. S cell xenograft model, comparing with the solvent control group, the compound of embodiment 26 (30 mg/kg) and Ixazomib (4 mg/kg) combined administrated group have the best tumor inhibition effect. The mice showed good tolerance and no significant weight loss.

What is claimed is:

1. A compound represented by formula (I), a pharmaceutically acceptable salt or a isomer thereof,

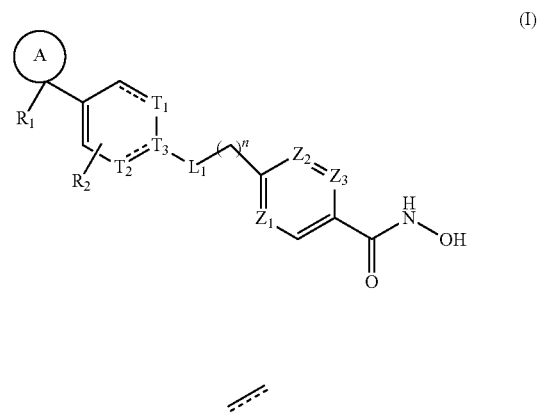

is a single bond or a double bond;
n is 0 or 1;
each of $T_1$, $T_2$ is independently selected from the group consisting of CH, $CH_2$, —C(=O)— and N;
$T_3$ is C or N;
each of $Z_1$, $Z_2$, $Z_3$ is CH;
$L_1$ is selected from the group consisting of a single bond, —NH— and —C(=O)—NH—;
$R_1$ is selected from the group consisting of $C_{1-3}$ alkyl, phenyl or 6-membered heteroaryl, each of which is optionally substituted by 1, 2 or 3 R;
$R_2$ is —H, F, Cl, Br or I;
Ring A is 4 to 7-membered heterocycloalkyl;
R is F, Cl, Br or I;
the "hetero" in 6-membered heteroaryl or 4 to 7-membered heterocycloalkyl is independently —NH—, N or —O—;
in any of the cases above, the number of heteroatom or heteroatom group is independently 1, 2 or 3, respectively.

2. The compound, the pharmaceutically acceptable salt or the isomer thereof as defined in claim 1, wherein $R_1$ is selected from the group consisting of methyl, ethyl, isopropyl, phenyl and pyridyl, each of which is optionally substituted by 1, 2 or 3 R; or, ring A is selected from the group consisting of oxetanyl, tetrahydrofuranyl, tetrahydropyranyl, 1,3-dioxolanyl, 1,4-dioxepinyl, 1,4-dioxanyl, 1,4-oxazacycloheptyl and morpholinyl; or, the structural unit

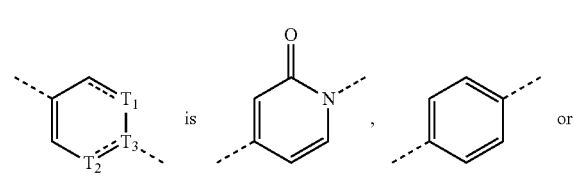

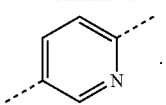

3. The compound, the pharmaceutically acceptable salt or the isomer thereof as defined in claim 2, wherein R₁ is selected from the group consisting of CH₃,

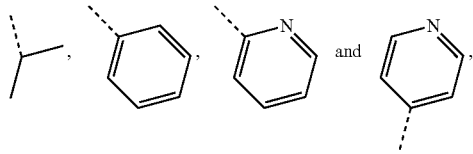

each of which is optionally substituted by 1, 2 or 3 R; or, ring A is selected from the group consisting of

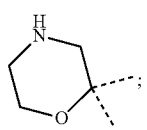

or, the structural unit

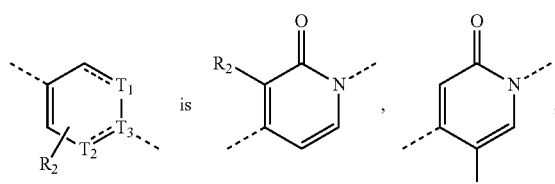

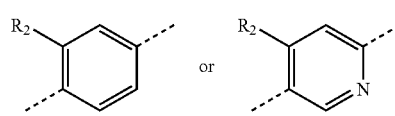

4. The compound, the pharmaceutically acceptable salt or the isomer thereof as defined in claim 3, wherein R₁ is selected from the group consisting of CH₃,

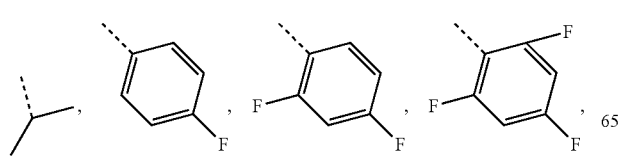

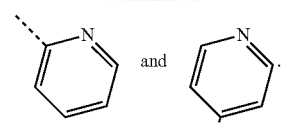

5. The compound, the pharmaceutically acceptable salt or the isomer thereof as defined in claim 3, wherein the structural unit

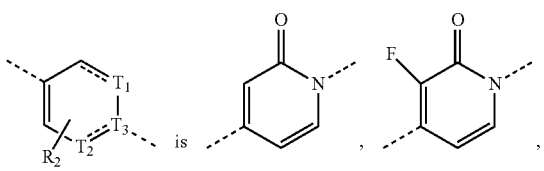

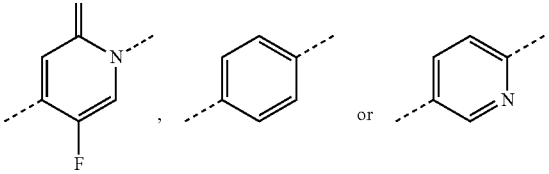

6. The compound, the pharmaceutically acceptable salt or the isomer thereof as defined in claim 1, wherein the structural unit

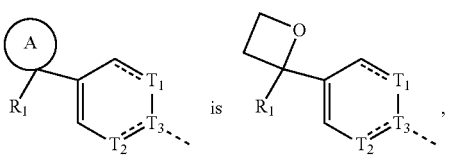

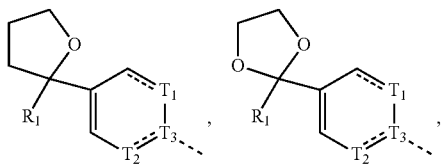

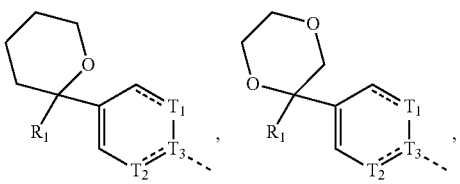

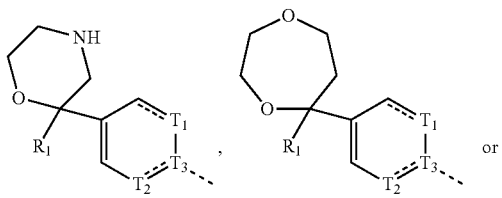

-continued

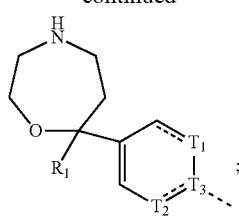

or, the structural unit

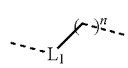

is selected from the group consisting of —CH$_2$—, —NH—, —C(=O)—NH—,

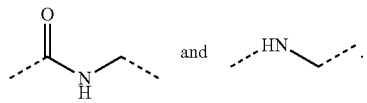

7. The compound, the pharmaceutically acceptable salt or the isomer thereof as defined in claim 6, wherein the structural unit

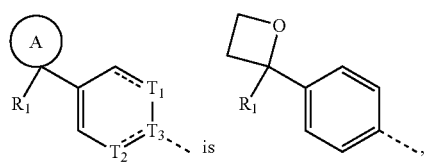 is

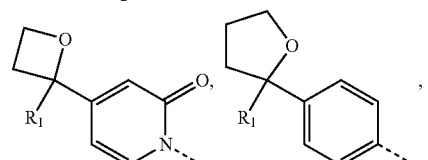

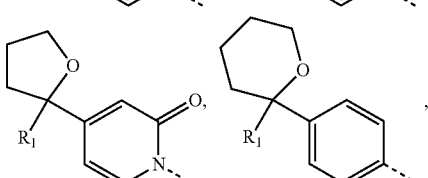

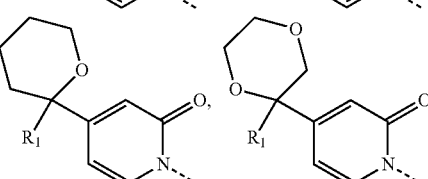

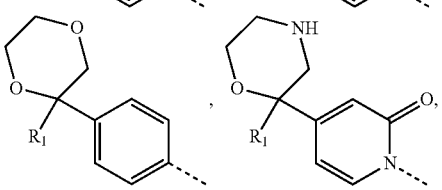

-continued

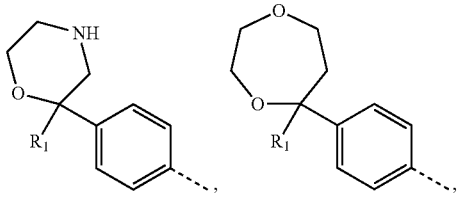

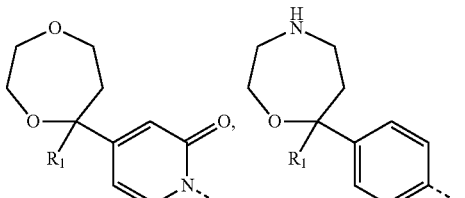

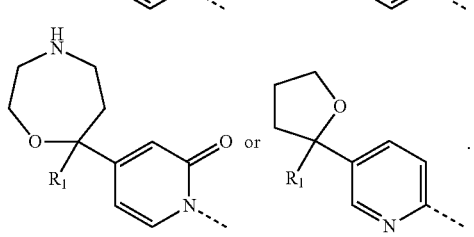

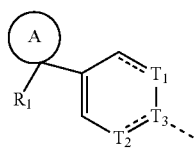 or

8. The compound, the pharmaceutically acceptable salt or the isomer thereof as defined in claim 7, wherein the structural unit

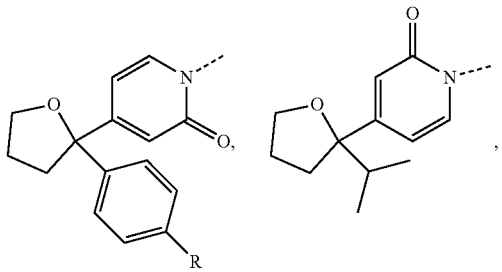

is selected from the group consisting of

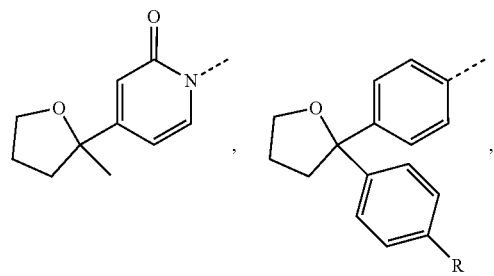

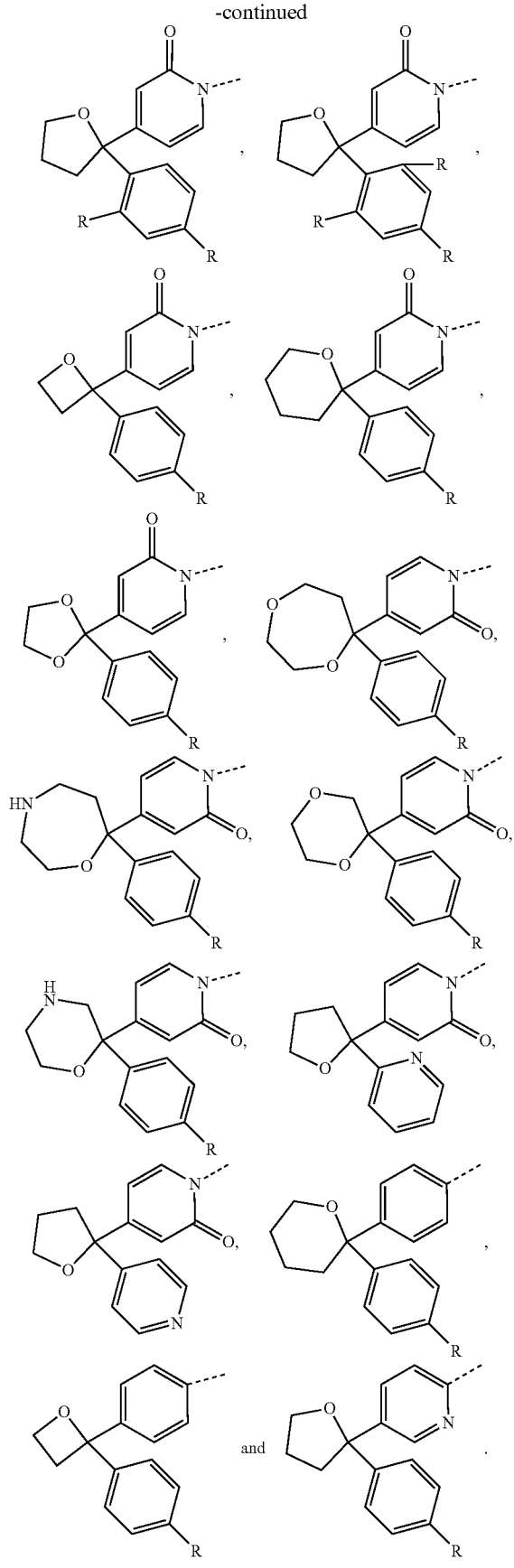
9. The compound, the pharmaceutically acceptable salt or the isomer thereof as defined in claim 8, wherein the structural unit
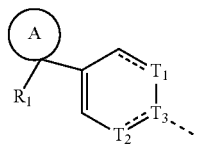
is selected from the group consisting of
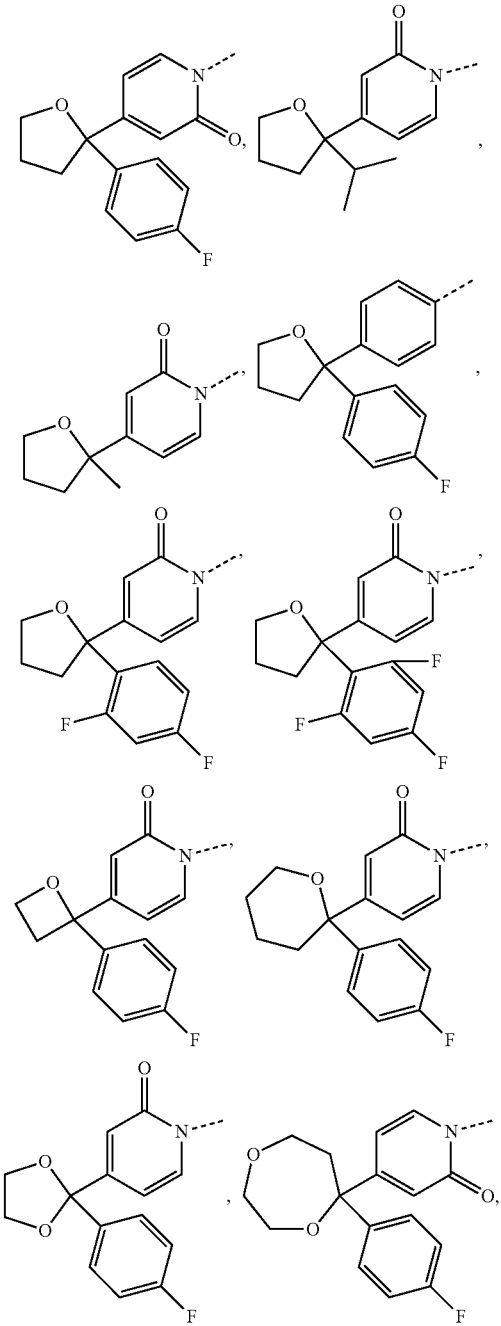

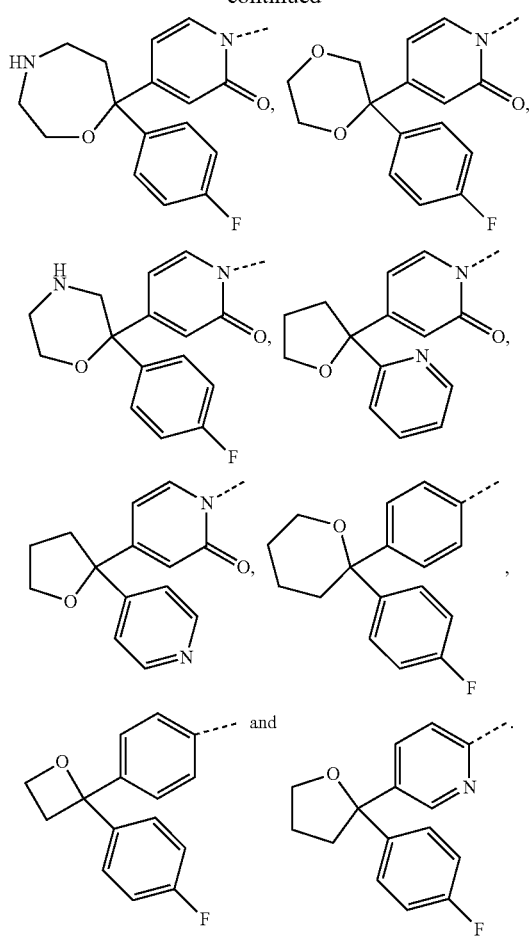
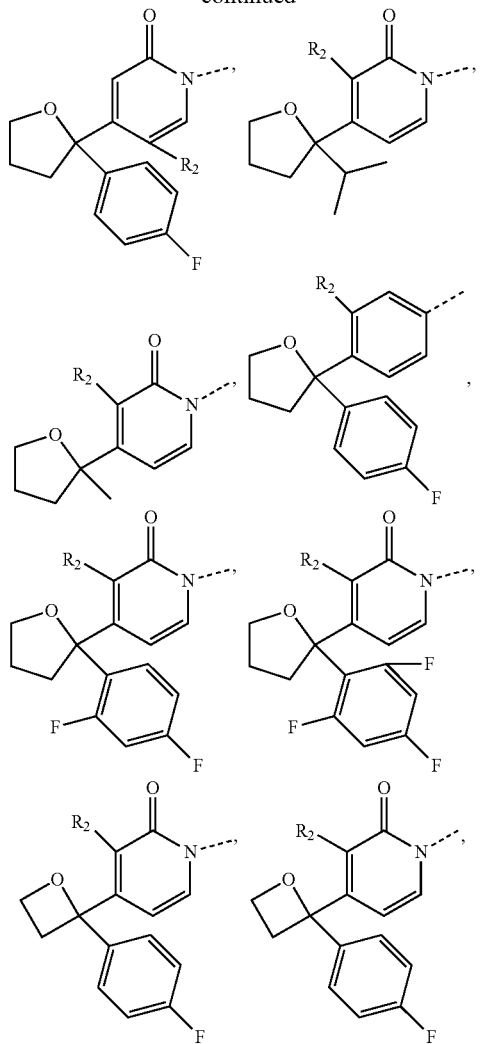
10. The compound, the pharmaceutically acceptable salt or the isomer thereof as defined in claim 1, wherein the structural unit
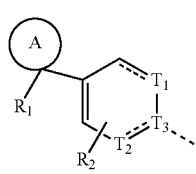
is selected from the group consisting of
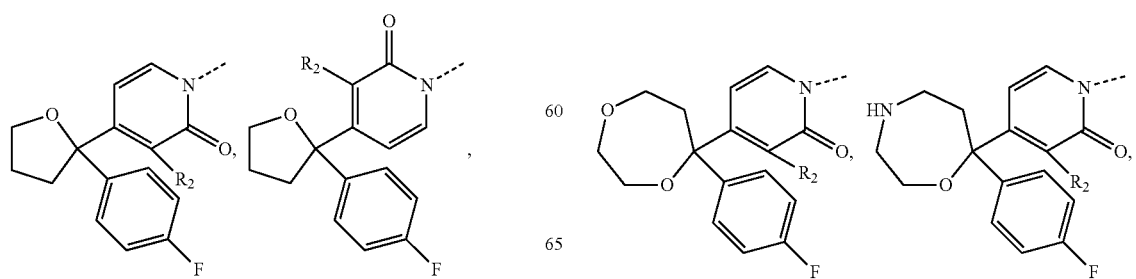

-continued
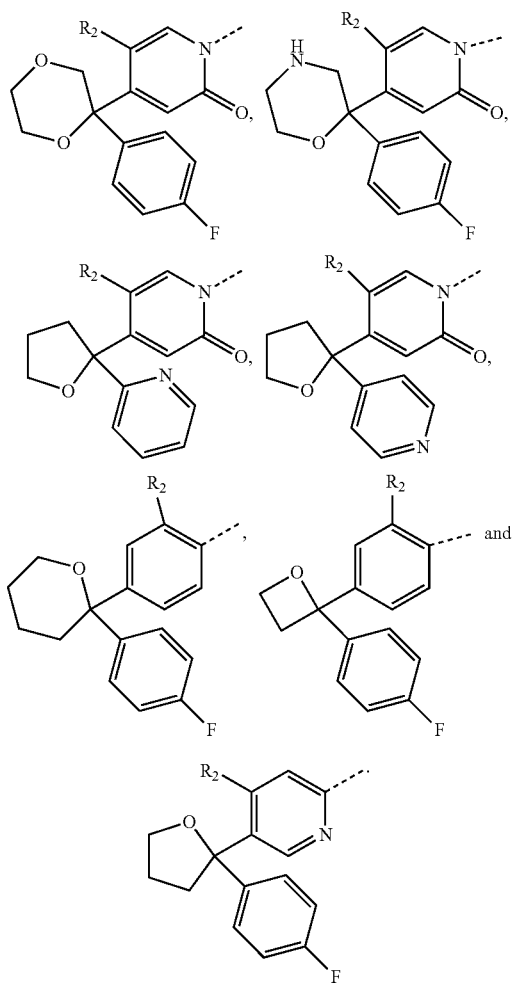
11. The compound, the pharmaceutically acceptable salt or the isomer thereof as defined in claim 10, wherein the structural unit
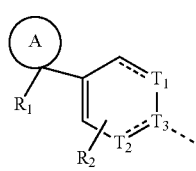
is selected from the group consisting of
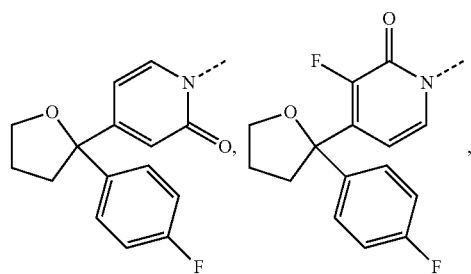
-continued
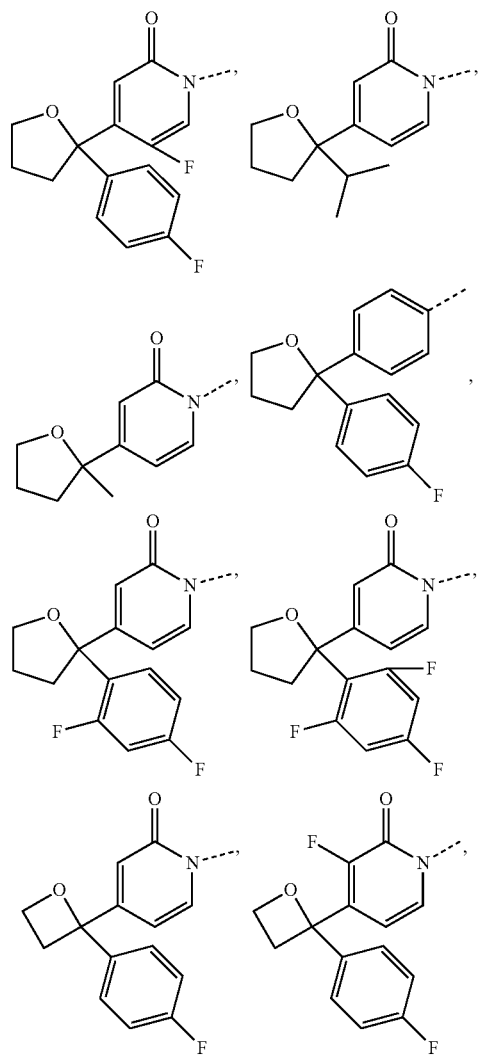
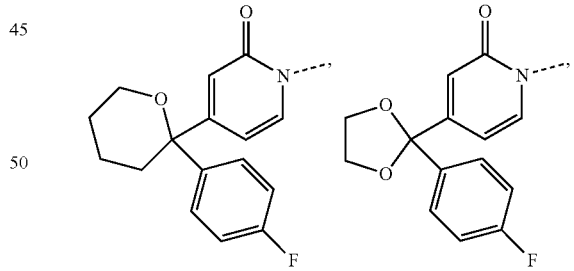
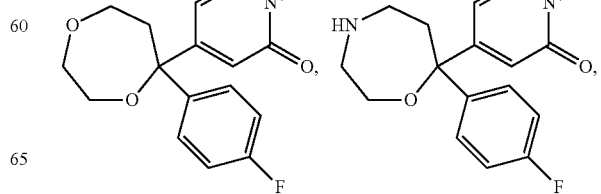

-continued

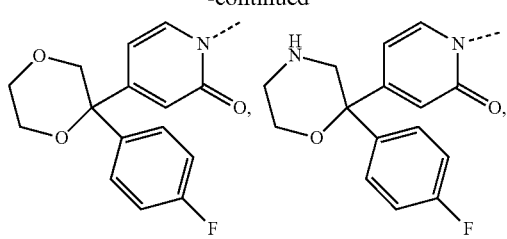

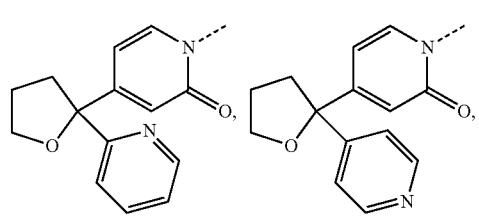

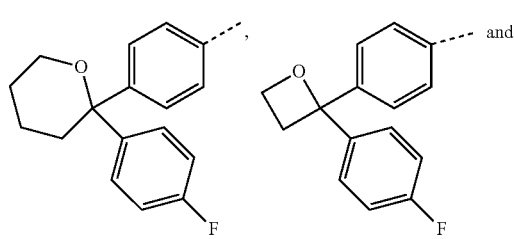

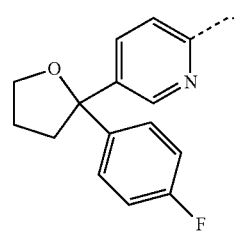

12. The compound, the pharmaceutically acceptable salt or the isomer thereof as defined in claim 1, wherein the structural unit

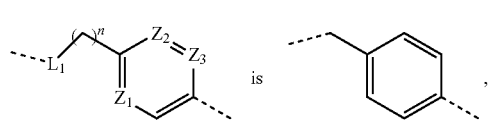 is 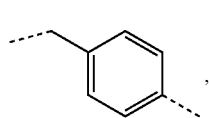,

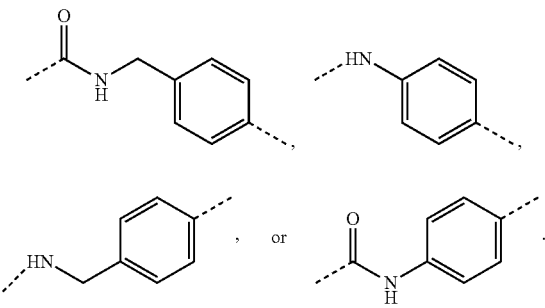

13. The compound, the pharmaceutically acceptable salt or the isomer thereof as defined in claim 1, which is selected from the group consisting of (I-1)

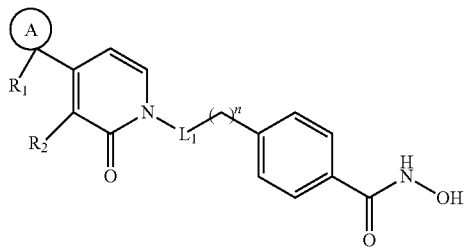

(I-5)

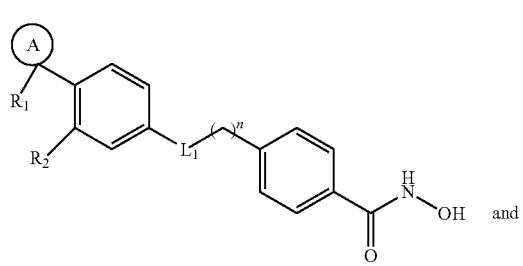 and (I-9)

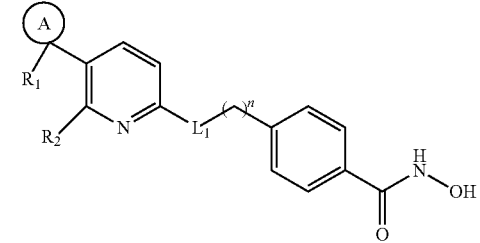

wherein, ring A, R, $R_2$, $L_1$ and n is as defined in claim 1;
$R_1$ is as defined in claim 1.

14. The compound, the pharmaceutically acceptable salt or the isomer thereof as defined in claim 13, which is (I-13)

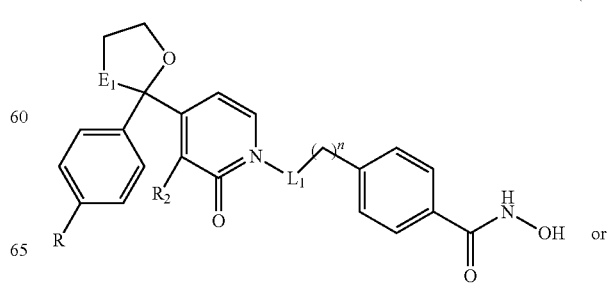 or (I-14)
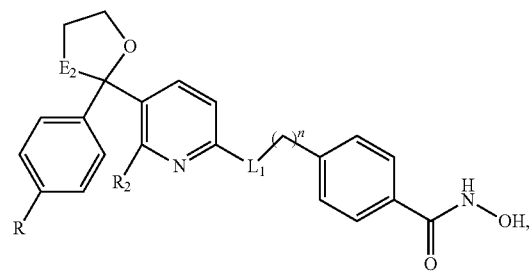
wherein,
each of E$_1$, E$_2$ is independently —O—, —CH$_2$— or —CH$_2$—CH$_2$—;
R, R$_2$, L$_1$ and n is as defined in claim 1.
15. The compounds or the pharmaceutically acceptable salt or the isomer thereof as defined in claim 1, which is selected from the group consisting of
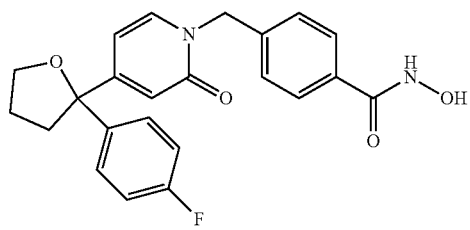
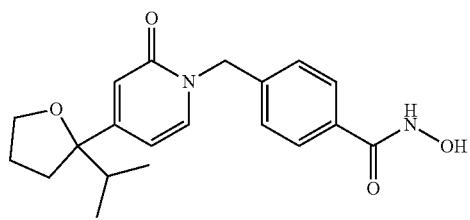
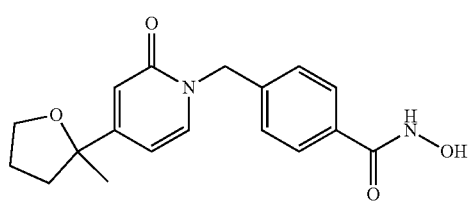
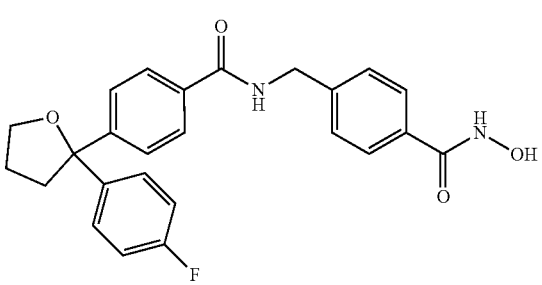
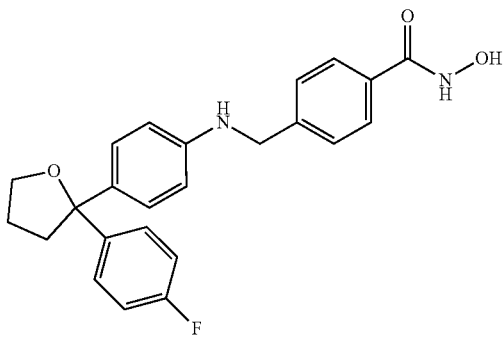
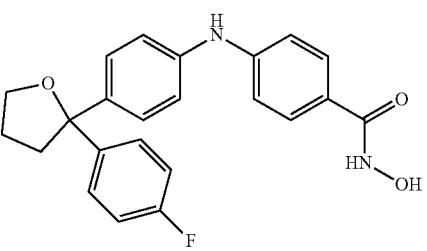
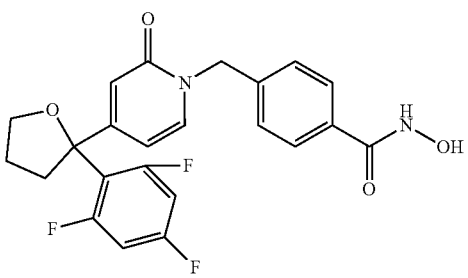
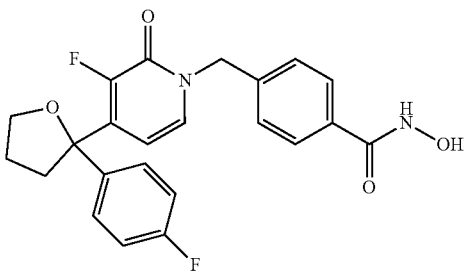
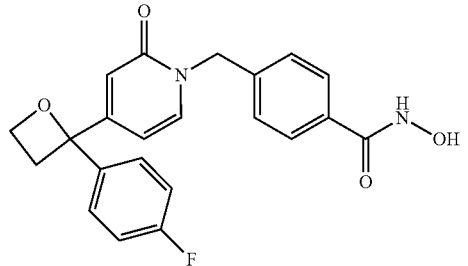
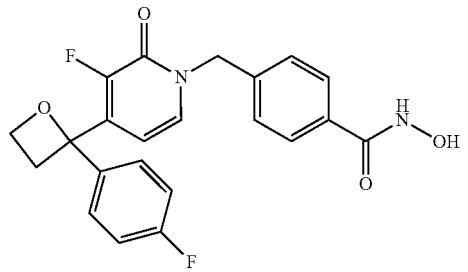

107
-continued

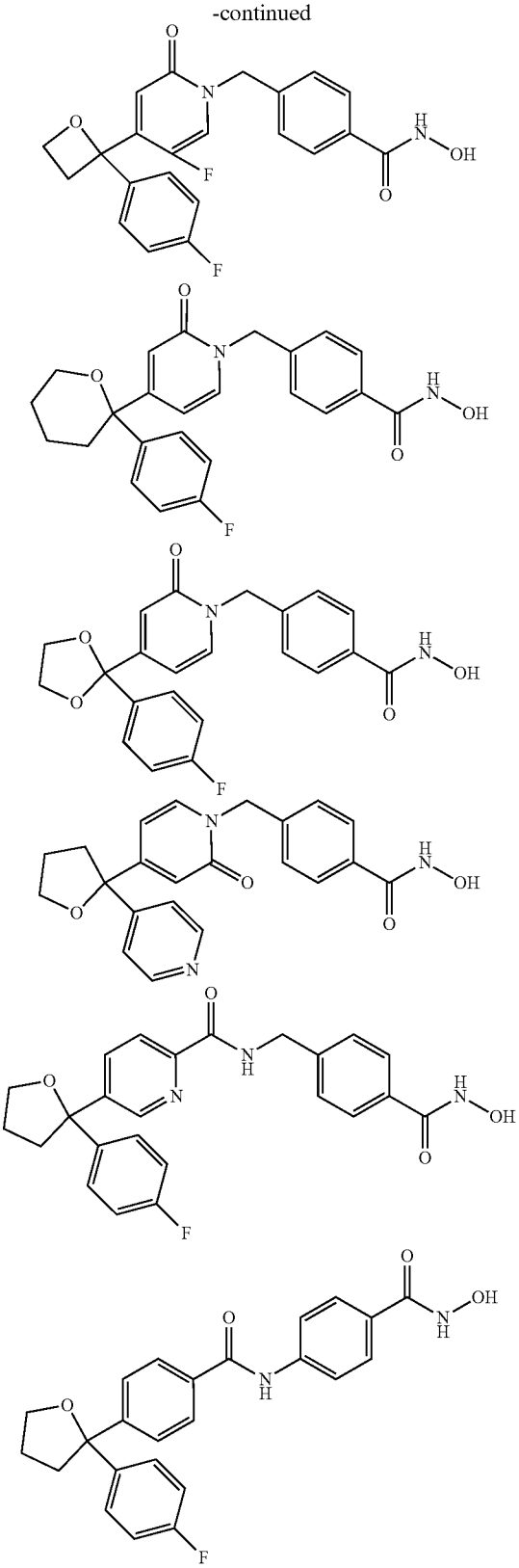

108
-continued

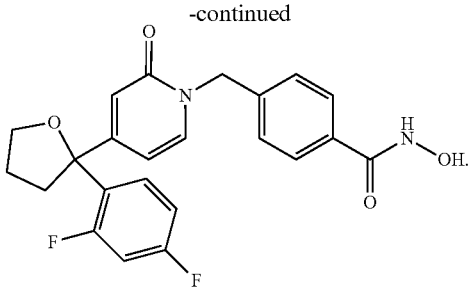

16. The compound, the pharmaceutically acceptable salt or the isomer thereof as defined in claim 15 is selected from the group consisting of

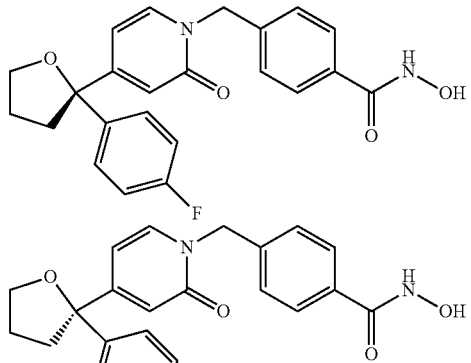

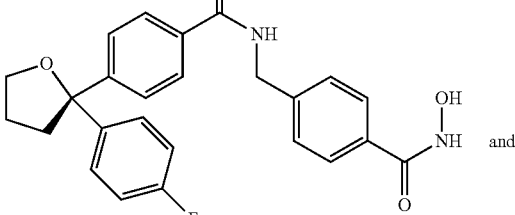 and

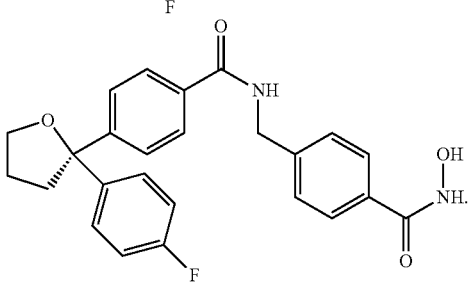

17. A pharmaceutical composition comprising a therapeutically effective amount of the compound or the pharmaceutically acceptable salt thereof as defined in claim 1 as an active ingredient, as well as a pharmaceutically acceptable carrier.

* * * * *

UNITED STATES PATENT AND TRADEMARK OFFICE
CERTIFICATE OF CORRECTION

PATENT NO. : 10,745,389 B2  
APPLICATION NO. : 16/476660  
DATED : August 18, 2020  
INVENTOR(S) : Hao Wu et al.

Page 1 of 1

It is certified that error appears in the above-identified patent and that said Letters Patent is hereby corrected as shown below:

In the Claims

In Column 107, Claim 15, Line 5:

Please delete:

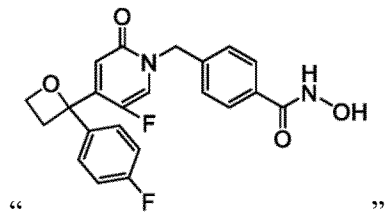

"                                              "

And insert:

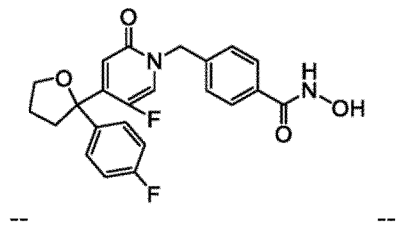

--                                              --

Signed and Sealed this  
Seventh Day of September, 2021

Drew Hirshfeld  
*Performing the Functions and Duties of the*  
*Under Secretary of Commerce for Intellectual Property and*  
*Director of the United States Patent and Trademark Office*